US009347586B2

(12) United States Patent
Williams et al.

(10) Patent No.: US 9,347,586 B2

(45) Date of Patent: May 24, 2016

(54) AUTOMATED PIPETTING APPARATUS HAVING A COMBINED LIQUID PUMP AND PIPETTE HEAD SYSTEM

(71) Applicant: HandyLab, Inc., Franklin Lakes, NJ (US)

(72) Inventors: Jeff Williams, Ypsilanti, MI (US); Kerry Wilson, Elkhart, IN (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

(21) Appl. No.: 13/652,368

(22) Filed: Oct. 15, 2012

(65) Prior Publication Data

US 2013/0037564 A1 Feb. 14, 2013

Related U.S. Application Data

(63) Continuation of application No. 12/212,403, filed on Sep. 17, 2008, now Pat. No. 8,287,820, which is a continuation-in-part of application No. 12/173,023, filed on Jul. 14, 2008, now Pat. No. 8,133,671, and a (Continued)

(51) Int. Cl.

*G01N 35/10* (2006.01)
*G01N 35/00* (2006.01)

(Continued)

(52) U.S. Cl.

CPC ............. *F16K 99/0001* (2013.01); *B01L 3/021* (2013.01); *F16K 99/003* (2013.01);

(Continued)

(58) Field of Classification Search

CPC .............. B01L 13/021; B01L 13/0213; B01L 13/0217; B01L 13/0227; B01L 13/0231; B01L 13/0234; B01L 13/0237

USPC ............ 422/63, 65, 500, 501, 509, 510, 511, 422/521, 522, 560, 561, 562, 564

See application file for complete search history.

(56) References Cited

U.S. PATENT DOCUMENTS 1,434,314 A 10/1922 Raich
1,616,419 A 2/1927 Wilson (Continued)

FOREIGN PATENT DOCUMENTS

CA 2294819 1/1999
CN 103540518 1/2014

(Continued)

OTHER PUBLICATIONS

Bollet et al., "A simple method for the isolation of chromosomal DNA from Gram positive or acid-fast bacteria", Nucleic Acids Research, vol. 19, No. 8 (1991), p. 1955.

(Continued)

*Primary Examiner* — Lyle Alexander
*Assistant Examiner* — Robert Eom
(74) *Attorney, Agent, or Firm* — Knobbe, Martens, Olson & Bear, LLP

(57) ABSTRACT

The technology described herein generally relates to systems for extracting polynucleotides from multiple samples, particularly from biological samples, and additionally to systems that subsequently amplify and detect the extracted polynucleotides. The technology more particularly relates to microfluidic systems that carry out PCR on multiple samples of nucleotides of interest within microfluidic channels, and detect those nucleotides. The technology still more particularly relates to automated devices for carrying out pipetting operations, particularly on samples in parallel, consistent with sample preparation and delivery of PCR-ready nucleotide extracts to a cartridge wherein PCR is run.

21 Claims, 26 Drawing Sheets

Fluid Distribution Head

Related U.S. Application Data continuation-in-part of application No. 12/218,498, filed on Jul. 14, 2008.

(60) Provisional application No. 60/959,437, filed on Jul. 13, 2007.

(51) Int. Cl.
*G01N 35/02* (2006.01)
*F16K 99/00* (2006.01)
*B01L 3/02* (2006.01)
*G01N 35/04* (2006.01)

(52) U.S. Cl.
CPC ........ *F16K 99/0032* (2013.01); *F16K 99/0044* (2013.01); *F16K 99/0061* (2013.01); *G01N 35/1065* (2013.01); *B01L 2200/143* (2013.01); *B01L 2400/0487* (2013.01); *F16K 2099/0084* (2013.01); *G01N 2035/00881* (2013.01); *G01N 2035/0436* (2013.01)

(56) References Cited

U.S. PATENT DOCUMENTS 1,733,401 A 8/1930 Lovekin
D189,404 S 12/1960 Nicolle
3,528,449 A 9/1970 Witte et al.
3,813,316 A 5/1974 Chakrabarty et al.
3,985,649 A 10/1976 Eddelman
4,018,089 A 4/1977 Dzula et al.
4,018,652 A 4/1977 Lanham et al.
4,038,192 A 7/1977 Serur
4,055,395 A 10/1977 Honkawa et al.
D249,706 S 9/1978 Adamski
4,139,005 A 2/1979 Dickey
D252,157 S 6/1979 Kronish et al.
D252,341 S 7/1979 Thomas
D254,687 S 4/1980 Fadler et al.
4,212,744 A 7/1980 Oota
D261,033 S 9/1981 Armbruster
D261,173 S 10/1981 Armbruster
4,301,412 A 11/1981 Hill et al.
4,439,526 A 3/1984 Columbus
4,457,329 A 7/1984 Werley et al.
4,466,740 A 8/1984 Kano et al.
4,504,582 A 3/1985 Swann
4,522,786 A 6/1985 Ebersole
D279,817 S 7/1985 Chen et al.
D282,208 S 1/1986 Lowry
4,599,315 A 7/1986 Terasaki et al.
4,612,873 A 9/1986 Eberle
4,612,959 A 9/1986 Costello
D288,478 S 2/1987 Carlson et al.
4,647,432 A 3/1987 Wakatake
4,654,127 A 3/1987 Baker et al.
4,673,657 A 6/1987 Christian
4,678,752 A 7/1987 Thorne et al.
4,683,195 A 7/1987 Mullis et al.
4,683,202 A 7/1987 Mullis
D292,735 S 11/1987 Lovborg
4,720,374 A 1/1988 Ramachandran
4,724,207 A 2/1988 Hou et al.
4,798,693 A 1/1989 Mase et al.
4,800,022 A 1/1989 Leonard
4,841,786 A 6/1989 Schulz
D302,294 S 7/1989 Hillman
4,871,779 A 10/1989 Killat et al.
4,895,650 A 1/1990 Wang
4,919,829 A 4/1990 Gates et al.
4,921,809 A 5/1990 Schiff et al.
4,935,342 A 6/1990 Seligson et al.
4,946,562 A 8/1990 Guruswamy
4,949,742 A 8/1990 Rando et al.
D310,413 S 9/1990 Bigler et al.
4,963,498 A 10/1990 Hillman
4,967,950 A 11/1990 Legg et al.
D312,692 S 12/1990 Bradley
4,978,502 A 12/1990 Dole et al.
4,978,622 A 12/1990 Mishell et al.
4,989,626 A 2/1991 Takagi et al.
5,001,417 A 3/1991 Pumphrey et al.
5,004,583 A 4/1991 Guruswamy et al.
5,048,554 A 9/1991 Kremer
5,053,199 A 10/1991 Keiser et al.
5,060,823 A 10/1991 Perlman
5,061,336 A 10/1991 Soane
5,064,618 A 11/1991 Baker et al.
5,071,531 A 12/1991 Soane
5,091,328 A 2/1992 Miller
D324,426 S 3/1992 Fan et al.
5,096,669 A 3/1992 Lauks et al.
D325,638 S 4/1992 Sloat et al.
5,126,002 A 6/1992 Iwata et al.
5,126,022 A 6/1992 Soane et al.
D328,135 S 7/1992 Fan et al.
D328,794 S 8/1992 Frenkel et al.
5,135,627 A 8/1992 Soane
5,135,872 A 8/1992 Pouletty et al.
5,147,606 A 9/1992 Charlton et al.
5,169,512 A 12/1992 Wiedenmann et al.
D333,522 S 2/1993 Gianino
5,186,339 A 2/1993 Heissler
5,192,507 A 3/1993 Taylor et al.
5,208,163 A 5/1993 Charlton et al.
5,217,694 A 6/1993 Gibler et al.
5,223,226 A 6/1993 Wittmer et al.
D338,275 S 8/1993 Fischer et al.
5,250,263 A 10/1993 Manz
5,252,743 A 10/1993 Barrett et al.
5,256,376 A 10/1993 Callan et al.
5,275,787 A 1/1994 Yuguchi et al.
5,282,950 A 2/1994 Dietze et al.
5,296,375 A 3/1994 Kricka et al.
5,304,477 A 4/1994 Nagoh et al.
5,304,487 A 4/1994 Wilding et al.
D347,478 S 5/1994 Pinkney
5,311,896 A 5/1994 Kaartinen et al.
5,311,996 A 5/1994 Duffy et al.
5,316,727 A 5/1994 Suzuki et al.
5,327,038 A 7/1994 Culp
5,339,486 A 8/1994 Persic, Jr.
D351,913 S 10/1994 Hieb et al.
5,364,591 A 11/1994 Green et al.
5,372,946 A 12/1994 Cusak et al.
5,374,395 A 12/1994 Robinson
5,389,339 A 2/1995 Petschek et al.
D356,232 S 3/1995 Armstrong et al.
5,397,709 A 3/1995 Berndt
5,401,465 A 3/1995 Smethers et al.
5,411,708 A 5/1995 Moscetta et al.
5,414,245 A 5/1995 Hackleman
5,416,000 A 5/1995 Allen et al.
5,422,271 A 6/1995 Chen et al.
5,422,284 A 6/1995 Lau
5,427,946 A 6/1995 Kricka et al.
5,443,791 A * 8/1995 Cathcart et al. ................. 422/65
5,474,796 A 12/1995 Brennan
D366,116 S 1/1996 Biskupski
5,486,335 A 1/1996 Wilding et al.
5,494,639 A 2/1996 Grzegorzewski
5,498,392 A 3/1996 Wilding et al.
5,503,803 A 4/1996 Brown
5,516,410 A 5/1996 Schneider et al.
5,519,635 A 5/1996 Miyake et al.
5,529,677 A 6/1996 Schneider et al.
5,559,432 A 9/1996 Logue
5,565,171 A 10/1996 Dovichi et al.
5,569,364 A 10/1996 Hooper et al.
5,578,270 A 11/1996 Reichler et al.
5,578,818 A 11/1996 Kain et al.
5,580,523 A 12/1996 Bard
5,582,884 A 12/1996 Ball et al.
5,585,069 A 12/1996 Zanucchi et al.
5,585,089 A 12/1996 Queen et al.

(56) References Cited

U.S. PATENT DOCUMENTS 5,585,242 A 12/1996 Bouma et al.
5,587,128 A 12/1996 Wilding et al.
5,589,136 A 12/1996 Northrup et al.
5,593,838 A 1/1997 Zanzucchi et al.
5,595,708 A 1/1997 Berndt
5,599,432 A 2/1997 Manz et al.
5,599,503 A 2/1997 Manz et al.
5,599,667 A 2/1997 Arnold, Jr. et al.
5,601,727 A 2/1997 Bormann et al.
5,603,351 A 2/1997 Cherukuri et al.
5,605,662 A 2/1997 Heller et al.
D378,782 S 4/1997 LaBarbera et al.
5,628,890 A 5/1997 Carter et al.
5,630,920 A 5/1997 Friese et al.
5,631,337 A 5/1997 Sassi et al.
5,632,876 A 5/1997 Zanzucchi et al.
5,632,957 A 5/1997 Heller et al.
5,635,358 A 6/1997 Wilding et al.
5,637,469 A 6/1997 Wilding et al.
5,639,423 A 6/1997 Northrup et al.
5,643,738 A 7/1997 Zanzucchi et al.
5,646,039 A 7/1997 Northrup et al.
5,646,049 A 7/1997 Tayi
5,647,994 A 7/1997 Tuunanen et al.
5,651,839 A 7/1997 Rauf
5,652,141 A 7/1997 Henco et al.
5,652,149 A 7/1997 Mileaf et al.
D382,346 S 8/1997 Buhler et al.
D382,647 S 8/1997 Staples et al.
5,667,976 A 9/1997 Van Ness et al.
5,671,303 A 9/1997 Shieh et al.
5,674,394 A 10/1997 Whitmore
5,674,742 A 10/1997 Northrup et al.
5,681,484 A 10/1997 Zanzucchi et al.
5,681,529 A 10/1997 Taguchi et al.
5,683,657 A 11/1997 Mian
5,699,157 A 12/1997 Parce
5,700,637 A 12/1997 Southern
5,705,813 A 1/1998 Apffel et al.
5,721,136 A 2/1998 Finney et al.
5,726,026 A 3/1998 Wilding et al.
5,726,404 A 3/1998 Brody
5,726,944 A 3/1998 Pelley et al.
5,731,212 A 3/1998 Gavin et al.
5,744,366 A 4/1998 Kricka et al.
5,747,666 A 5/1998 Willis
5,750,015 A 5/1998 Soane et al.
5,755,942 A 5/1998 Zanzucchi et al.
5,762,874 A 6/1998 Seaton et al.
5,763,262 A 6/1998 Wong et al.
5,770,029 A 6/1998 Nelson et al.
5,770,388 A 6/1998 Vorpahl
5,772,966 A 6/1998 Maracas et al.
5,779,868 A 7/1998 Parce et al.
5,787,032 A 7/1998 Heller et al.
5,788,814 A 8/1998 Sun et al.
5,800,600 A 9/1998 Lima-Marques et al.
5,800,690 A 9/1998 Chow et al.
5,804,436 A 9/1998 Okun et al.
D399,959 S 10/1998 Prokop et al.
5,827,481 A 10/1998 Bente et al.
5,842,106 A 11/1998 Thaler et al.
5,842,787 A 12/1998 Kopf-Sill et al.
5,846,396 A 12/1998 Zanzucchi et al.
5,846,493 A 12/1998 Bankier et al.
5,849,208 A 12/1998 Hayes et al.
5,849,486 A 12/1998 Heller et al.
5,849,489 A 12/1998 Heller
5,849,598 A 12/1998 Wilson et al.
5,852,495 A 12/1998 Parce
5,856,174 A 1/1999 Lipshutz et al.
5,858,187 A 1/1999 Ramsey et al.
5,858,188 A 1/1999 Soane et al.
5,863,502 A 1/1999 Southgate et al.
5,863,708 A 1/1999 Zanzucchi et al.
5,863,801 A 1/1999 Southgate et al.
5,866,345 A 2/1999 Wilding et al.
5,869,004 A 2/1999 Parce et al.
5,869,244 A 2/1999 Martin et al.
5,872,010 A 2/1999 Karger et al.
5,872,623 A 2/1999 Stabile et al.
5,874,046 A 2/1999 Megerle
5,876,675 A 3/1999 Kennedy
5,880,071 A 3/1999 Parce et al.
5,882,465 A 3/1999 McReynolds
5,883,211 A 3/1999 Sassi et al.
5,885,432 A 3/1999 Hooper et al.
5,885,470 A 3/1999 Parce et al.
5,895,762 A 4/1999 Greenfield et al.
5,900,130 A 5/1999 Benregnu et al.
5,912,124 A 6/1999 Kumar
5,912,134 A 6/1999 Shartle
5,916,522 A 6/1999 Boyd et al.
5,916,776 A 6/1999 Kumar
5,919,711 A 7/1999 Boyd et al.
5,922,591 A 7/1999 Anderson et al.
5,927,547 A 7/1999 Papen et al.
5,928,880 A 7/1999 Wilding et al.
5,929,208 A 7/1999 Heller et al.
D413,391 S 8/1999 Lapeus et al.
5,932,799 A 8/1999 Moles
5,935,401 A 8/1999 Amigo
5,939,291 A 8/1999 Loewy et al.
5,942,443 A 8/1999 Parce et al.
D413,677 S 9/1999 Dumitrescu et al.
5,948,227 A 9/1999 Dubrow
5,948,363 A 9/1999 Gaillard
5,955,028 A 9/1999 Chow
5,955,029 A 9/1999 Wilding et al.
5,957,579 A 9/1999 Kopf-Sill et al.
5,958,203 A 9/1999 Parce et al.
5,958,694 A 9/1999 Nikiforov
5,959,221 A 9/1999 Boyd et al.
5,959,291 A 9/1999 Jensen
5,964,995 A 10/1999 Nikiforov et al.
5,964,997 A 10/1999 McBride
5,965,001 A 10/1999 Chow et al.
5,965,410 A 10/1999 Chow et al.
5,965,886 A 10/1999 Sauer et al.
5,968,745 A 10/1999 Thorp et al.
5,972,187 A 10/1999 Parce et al.
5,973,138 A 10/1999 Collis
D417,009 S 11/1999 Boyd
5,976,336 A 11/1999 Dubrow et al.
5,980,704 A 11/1999 Cherukuri et al.
5,980,719 A 11/1999 Cherukuri et al.
5,981,735 A 11/1999 Thatcher et al.
5,989,402 A 11/1999 Chow et al.
5,992,820 A 11/1999 Fare et al.
5,993,611 A 11/1999 Moroney et al.
5,993,750 A 11/1999 Ghosh et al.
5,997,708 A 12/1999 Craig
6,001,229 A 12/1999 Ramsey
6,001,231 A 12/1999 Kopf-Sill
6,001,307 A 12/1999 Naka et al.
6,004,515 A 12/1999 Parce et al.
6,007,690 A 12/1999 Nelson et al.
6,010,607 A 1/2000 Ramsey
6,010,608 A 1/2000 Ramsey
6,010,627 A 1/2000 Hood
6,012,902 A 1/2000 Parce
D420,747 S 2/2000 Dumitrescu et al.
D421,130 S 2/2000 Cohen et al.
6,024,920 A 2/2000 Cunanan
D421,653 S 3/2000 Purcell
6,033,546 A 3/2000 Ramsey
6,043,080 A 3/2000 Lipshutz et al.
6,046,056 A 4/2000 Parce et al.
6,048,734 A 4/2000 Burns et al.
6,054,034 A 4/2000 Soane et al.
6,054,277 A 4/2000 Furcht et al.
6,056,860 A 5/2000 Amigo et al.
6,057,149 A 5/2000 Burns et al.
6,062,261 A 5/2000 Jacobson et al.

(56) References Cited

U.S. PATENT DOCUMENTS

| | | | |
|---|---|---|---|
| 6,063,341 | A | 5/2000 | Fassbind et al. |
| 6,063,589 | A | 5/2000 | Kellogg et al. |
| 6,071,478 | A | 6/2000 | Chow |
| 6,074,725 | A | 6/2000 | Kennedy |
| 6,074,827 | A | 6/2000 | Nelson et al. |
| D428,497 | S | 7/2000 | Lapeus et al. |
| 6,086,740 | A | 7/2000 | Kennedy |
| 6,096,509 | A | 8/2000 | Okun et al. |
| 6,100,541 | A | 8/2000 | Nagle et al. |
| 6,102,897 | A | 8/2000 | Lang |
| 6,103,537 | A | 8/2000 | Ullman et al. |
| 6,106,685 | A | 8/2000 | McBride et al. |
| 6,110,343 | A | 8/2000 | Ramsey et al. |
| 6,123,205 | A | 9/2000 | Dumitrescu et al. |
| 6,123,798 | A | 9/2000 | Gandhi et al. |
| 6,130,098 | A | 10/2000 | Handique et al. |
| 6,132,580 | A | 10/2000 | Mathies et al. |
| 6,132,684 | A | 10/2000 | Marino |
| 6,133,436 | A | 10/2000 | Koster et al. |
| D433,759 | S | 11/2000 | Mathis et al. |
| 6,143,250 | A | 11/2000 | Tajima |
| 6,149,787 | A | 11/2000 | Chow et al. |
| 6,156,199 | A | 12/2000 | Zuk |
| 6,158,269 | A | 12/2000 | Dorenkott et al. |
| 6,167,910 | B1 | 1/2001 | Chow |
| 6,168,948 | B1 | 1/2001 | Anderson et al. |
| 6,171,850 | B1 | 1/2001 | Nagle et al. |
| 6,174,675 | B1 | 1/2001 | Chow et al. |
| 6,180,950 | B1 | 1/2001 | Olsen |
| D438,311 | S | 2/2001 | Yamanishi et al. |
| 6,190,619 | B1 | 2/2001 | Kilcoin et al. |
| D438,632 | S | 3/2001 | Miller |
| D438,633 | S | 3/2001 | Miller |
| D439,673 | S | 3/2001 | Brophy et al. |
| 6,197,595 | B1 | 3/2001 | Anderson et al. |
| 6,211,989 | B1 | 4/2001 | Wulf et al. |
| 6,213,151 | B1 | 4/2001 | Jacobson et al. |
| 6,221,600 | B1 | 4/2001 | MacLeod et al. |
| 6,228,635 | B1 | 5/2001 | Armstrong et al. |
| 6,232,072 | B1 | 5/2001 | Fisher |
| 6,235,175 | B1 | 5/2001 | Dubrow et al. |
| 6,235,313 | B1 | 5/2001 | Mathiowitz et al. |
| 6,235,471 | B1 | 5/2001 | Knapp et al. |
| 6,236,456 | B1 | 5/2001 | Giebeler et al. |
| 6,236,581 | B1 | 5/2001 | Foss et al. |
| 6,238,626 | B1 | 5/2001 | Higuchi et al. |
| 6,251,343 | B1 | 6/2001 | Dubrow et al. |
| 6,254,826 | B1 | 7/2001 | Acosta et al. |
| 6,259,635 | B1 | 7/2001 | Khouri et al. |
| 6,261,431 | B1 | 7/2001 | Mathies et al. |
| 6,267,858 | B1 | 7/2001 | Parce et al. |
| D446,306 | S | 8/2001 | Ochi et al. |
| 6,271,021 | B1 | 8/2001 | Burns et al. |
| 6,274,089 | B1 | 8/2001 | Chow et al. |
| 6,280,967 | B1 | 8/2001 | Ransom et al. |
| 6,281,008 | B1 | 8/2001 | Komai et al. |
| 6,284,113 | B1 | 9/2001 | Bjornson et al. |
| 6,284,470 | B1 | 9/2001 | Bitner et al. |
| 6,287,254 | B1 | 9/2001 | Dodds |
| 6,287,774 | B1 | 9/2001 | Kikiforov |
| 6,291,248 | B1 | 9/2001 | Haj-Ahmad |
| 6,294,063 | B1 | 9/2001 | Becker et al. |
| 6,302,134 | B1 | 10/2001 | Kellogg et al. |
| 6,302,304 | B1 | 10/2001 | Spencer |
| 6,303,343 | B1 | 10/2001 | Kopf-sill |
| 6,306,273 | B1 | 10/2001 | Wainright et al. |
| 6,306,590 | B1 | 10/2001 | Mehta et al. |
| 6,316,774 | B1 | 11/2001 | Giebeler et al. |
| 6,319,469 | B1 | 11/2001 | Mian et al. |
| 6,322,683 | B1 | 11/2001 | Wolk et al. |
| 6,326,083 | B1 | 12/2001 | Yang et al. |
| 6,326,147 | B1 | 12/2001 | Oldham et al. |
| 6,326,211 | B1 | 12/2001 | Anderson et al. |
| 6,334,980 | B1 | 1/2002 | Hayes et al. |
| 6,337,435 | B1 | 1/2002 | Chu et al. |
| 6,353,475 | B1 | 3/2002 | Jensen et al. |
| 6,358,387 | B1 | 3/2002 | Kopf-sill et al. |
| 6,366,924 | B1 | 4/2002 | Parce |
| 6,368,561 | B1 | 4/2002 | Rutishauser et al. |
| 6,368,871 | B1 | 4/2002 | Christel et al. |
| 6,370,206 | B1 | 4/2002 | Schenk |
| 6,375,185 | B1 | 4/2002 | Lin |
| 6,375,901 | B1 | 4/2002 | Robotti et al. |
| 6,379,884 | B2 | 4/2002 | Wada et al. |
| 6,379,929 | B1 | 4/2002 | Burns et al. |
| 6,379,974 | B1 | 4/2002 | Parce et al. |
| 6,382,254 | B1 | 5/2002 | Yang et al. |
| 6,391,541 | B1 | 5/2002 | Petersen et al. |
| 6,391,623 | B1 | 5/2002 | Besemer et al. |
| 6,395,161 | B1 | 5/2002 | Schneider et al. |
| 6,398,956 | B1 | 6/2002 | Coville et al. |
| 6,399,025 | B1 | 6/2002 | Chow |
| 6,399,389 | B1 | 6/2002 | Parce et al. |
| 6,399,952 | B1 | 6/2002 | Maher et al. |
| 6,403,338 | B1 | 6/2002 | Knapp et al. |
| 6,408,878 | B2 | 6/2002 | Unger et al. |
| 6,413,401 | B1 | 7/2002 | Chow et al. |
| 6,416,642 | B1 | 7/2002 | Alajoki et al. |
| 6,420,143 | B1 | 7/2002 | Kopf-sill |
| 6,425,972 | B1 | 7/2002 | McReynolds |
| D461,906 | S | 8/2002 | Pham |
| 6,428,987 | B2 | 8/2002 | Franzen |
| 6,430,512 | B1 | 8/2002 | Gallagher |
| 6,432,366 | B2 | 8/2002 | Ruediger et al. |
| 6,440,725 | B1 | 8/2002 | Pourahmadi et al. |
| D463,031 | S | 9/2002 | Slomski et al. |
| 6,444,461 | B1 | 9/2002 | Knapp et al. |
| 6,447,661 | B1 | 9/2002 | Chow et al. |
| 6,447,727 | B1 | 9/2002 | Parce et al. |
| 6,448,064 | B1 | 9/2002 | Vo-Dinh et al. |
| 6,453,928 | B1 | 9/2002 | Kaplan et al. |
| 6,465,257 | B1 | 10/2002 | Parce et al. |
| 6,468,761 | B2 | 10/2002 | Yang et al. |
| 6,472,141 | B2 | 10/2002 | Nikiforov |
| 6,475,364 | B1 | 11/2002 | Dubrow et al. |
| D467,348 | S | 12/2002 | McMichael et al. |
| D467,349 | S | 12/2002 | Niedbala et al. |
| 6,488,897 | B2 | 12/2002 | Dubrow et al. |
| 6,495,104 | B1 | 12/2002 | Unno et al. |
| 6,498,497 | B1 | 12/2002 | Chow et al. |
| 6,500,323 | B1 | 12/2002 | Chow et al. |
| 6,500,390 | B1 | 12/2002 | Boulton et al. |
| D468,437 | S | 1/2003 | McMenamy et al. |
| 6,506,609 | B1 | 1/2003 | Wada et al. |
| 6,509,193 | B1 | 1/2003 | Tajima |
| 6,511,853 | B1 | 1/2003 | Kopf-sill et al. |
| D470,595 | S | 2/2003 | Crisanti et al. |
| 6,515,753 | B2 | 2/2003 | Maher |
| 6,517,783 | B2 | 2/2003 | Horner et al. |
| 6,520,197 | B2 | 2/2003 | Deshmukh et al. |
| 6,521,188 | B1 | 2/2003 | Webster |
| 6,524,456 | B1 | 2/2003 | Ramsey et al. |
| 6,524,790 | B1 | 2/2003 | Kopf-sill et al. |
| D472,324 | S | 3/2003 | Rumore et al. |
| 6,534,295 | B2 | 3/2003 | Tai et al. |
| 6,537,771 | B1 | 3/2003 | Farinas et al. |
| 6,540,896 | B1 | 4/2003 | Manz et al. |
| 6,544,734 | B1 | 4/2003 | Briscoe et al. |
| 6,547,942 | B1 | 4/2003 | Parce et al. |
| 6,555,389 | B1 | 4/2003 | Ullman et al. |
| 6,556,923 | B2 | 4/2003 | Gallagher et al. |
| D474,279 | S | 5/2003 | Mayer et al. |
| D474,280 | S | 5/2003 | Niedbala et al. |
| 6,558,916 | B2 | 5/2003 | Veerapandian et al. |
| 6,558,945 | B1 | 5/2003 | Kao |
| 6,569,607 | B2 | 5/2003 | McReynolds |
| 6,572,830 | B1 | 6/2003 | Burdon et al. |
| 6,575,188 | B2 | 6/2003 | Parunak |
| 6,576,459 | B2 | 6/2003 | Miles et al. |
| 6,579,453 | B1 | 6/2003 | Bächler et al. |
| 6,589,729 | B2 | 7/2003 | Chan et al. |
| 6,592,821 | B1 | 7/2003 | Wada et al. |
| 6,597,450 | B1 | 7/2003 | Andrews et al. |
| 6,602,474 | B1 | 8/2003 | Tajima |

(56) References Cited

U.S. PATENT DOCUMENTS 6,613,211 B1 9/2003 McCormick et al.
6,613,512 B1 9/2003 Kopf-sill et al.
6,613,580 B1 9/2003 Chow et al.
6,613,581 B1 9/2003 Wada et al.
6,614,030 B2 9/2003 Maher et al.
6,620,625 B2 9/2003 Wolk et al.
6,623,860 B2 9/2003 Hu et al.
6,627,406 B1 9/2003 Singh et al.
D480,814 S 10/2003 Lafferty et al.
6,632,655 B1 10/2003 Mehta et al.
6,633,785 B1 10/2003 Kasahara et al.
D482,796 S 11/2003 Oyama et al.
6,640,981 B2 11/2003 Lafond et al.
6,649,358 B1 11/2003 Parce et al.
6,664,104 B2 12/2003 Pourahmadi et al.
6,669,831 B2 12/2003 Chow et al.
6,670,153 B2 12/2003 Stern
D484,989 S 1/2004 Gebrian
6,672,458 B2 1/2004 Hansen et al.
6,681,616 B2 1/2004 Spaid et al.
6,681,788 B2 1/2004 Parce et al.
6,685,813 B2 2/2004 Williams et al.
6,692,700 B2 2/2004 Handique
6,695,009 B2 2/2004 Chien et al.
6,706,519 B1 3/2004 Kellogg et al.
6,720,148 B1 4/2004 Nikiforov
6,730,206 B2 5/2004 Ricco et al.
6,733,645 B1 5/2004 Chow
6,734,401 B2 5/2004 Bedingham et al.
6,737,026 B1 5/2004 Bergh et al.
6,740,518 B1 5/2004 Duong et al.
D491,272 S 6/2004 Alden et al.
D491,273 S 6/2004 Biegler et al.
D491,276 S 6/2004 Langille
6,750,661 B2 6/2004 Brooks et al.
6,752,966 B1 6/2004 Chazan
6,756,019 B1 6/2004 Dubrow et al.
6,764,859 B1 7/2004 Kreuwel et al.
6,766,817 B2 7/2004 da Silva
6,773,567 B1 8/2004 Wolk
6,777,184 B2 8/2004 Nikiforov et al.
6,783,962 B1 8/2004 Olander et al.
D495,805 S 9/2004 Lea et al.
6,787,015 B2 9/2004 Lackritz et al.
6,787,016 B2 9/2004 Tan et al.
6,787,111 B2 * 9/2004 Roach et al. .................. 422/509
6,790,328 B2 9/2004 Jacobson et al.
6,790,330 B2 9/2004 Gascoyne et al.
6,811,668 B1 11/2004 Berndt et al.
6,818,113 B2 11/2004 Williams et al.
6,819,027 B2 11/2004 Saraf
6,824,663 B1 11/2004 Boone
D499,813 S 12/2004 Wu
D500,142 S 12/2004 Crisanti et al.
D500,363 S 12/2004 Fanning et al.
6,827,831 B1 12/2004 Chow et al.
6,827,906 B1 12/2004 Bjornson et al.
6,838,156 B1 1/2005 Neyer et al.
6,838,680 B2 1/2005 Maher et al.
6,852,287 B2 2/2005 Ganesan
6,858,185 B1 2/2005 Kopf-sill et al.
6,859,698 B2 2/2005 Schmeisser
6,861,035 B2 3/2005 Pham et al.
6,878,540 B2 4/2005 Pourahmadi et al.
6,878,755 B2 4/2005 Singh et al.
6,884,628 B2 4/2005 Hubbell et al.
6,887,693 B2 5/2005 McMillan et al.
6,893,879 B2 5/2005 Petersen et al.
6,900,889 B2 5/2005 Bjornson et al.
6,905,583 B2 6/2005 Wainright et al.
6,905,612 B2 6/2005 Dorian et al.
6,906,797 B1 6/2005 Kao et al.
6,908,594 B1 6/2005 Schaevitz et al.
6,911,183 B1 6/2005 Handique et al.
6,914,137 B2 7/2005 Baker
6,915,679 B2 7/2005 Chien et al.
6,918,404 B2 7/2005 Dias da Silva
D508,999 S 8/2005 Fanning et al.
6,939,451 B2 9/2005 Zhao et al.
6,942,771 B1 9/2005 Kayyem
6,958,392 B2 10/2005 Fomovskaia et al.
D512,155 S 11/2005 Matsumoto
6,964,747 B2 11/2005 Banerjee et al.
6,977,163 B1 12/2005 Mehta
6,984,516 B2 1/2006 Briscoe et al.
D515,707 S 2/2006 Shinohara et al.
D516,221 S 2/2006 Wohlstadter et al.
7,001,853 B1 2/2006 Brown et al.
7,004,184 B2 2/2006 Handique et al.
D517,554 S 3/2006 Yanagisawa et al.
7,010,391 B2 3/2006 Handique et al.
7,023,007 B2 4/2006 Gallagher
7,024,281 B1 4/2006 Unno
7,036,667 B2 5/2006 Greenstein et al.
7,037,416 B2 5/2006 Parce et al.
7,038,472 B1 5/2006 Chien
7,039,527 B2 5/2006 Tripathi et al.
7,040,144 B2 5/2006 Spaid et al.
7,049,558 B2 5/2006 Baer et al.
D523,153 S 6/2006 Akashi et al.
7,055,695 B2 6/2006 Greenstein et al.
7,060,171 B1 6/2006 Nikiforov et al.
7,066,586 B2 6/2006 da Silva
7,069,952 B1 7/2006 McReynolds et al.
7,099,778 B2 8/2006 Chien
D528,215 S 9/2006 Malmsater
7,101,467 B2 9/2006 Spaid
7,105,304 B1 9/2006 Nikiforov et al.
D531,321 S 10/2006 Godfrey et al.
7,118,910 B2 10/2006 Unger et al.
7,138,032 B2 11/2006 Gandhi et al.
D534,280 S 12/2006 Gomm et al.
7,148,043 B2 12/2006 Kordunsky et al.
7,150,814 B1 12/2006 Parce et al.
7,150,999 B1 12/2006 Shuck
D535,403 S 1/2007 Isozaki et al.
7,160,423 B2 1/2007 Chien et al.
7,161,356 B1 1/2007 Chien
7,169,277 B2 1/2007 Ausserer et al.
7,169,618 B2 1/2007 Skould
D537,951 S 3/2007 Okamoto et al.
D538,436 S 3/2007 Patadia et al.
7,192,557 B2 3/2007 Wu et al.
7,195,986 B1 3/2007 Bousse et al.
7,208,125 B1 4/2007 Dong
7,235,406 B1 6/2007 Woudenberg et al.
7,247,274 B1 7/2007 Chow
D548,841 S 8/2007 Brownell et al.
D549,827 S 8/2007 Maeno et al.
7,252,928 B1 8/2007 Hafeman et al.
7,270,786 B2 9/2007 Parunak et al.
D554,069 S 10/2007 Bolotin et al.
D554,070 S 10/2007 Bolotin et al.
7,276,208 B2 10/2007 Sevigny et al.
7,276,330 B2 10/2007 Chow et al.
7,288,228 B2 10/2007 Lefebvre
D556,914 S 12/2007 Okamoto et al.
7,303,727 B1 12/2007 Dubrow et al.
D559,995 S 1/2008 Handique et al.
7,323,140 B2 1/2008 Handique et al.
7,332,130 B2 2/2008 Handique
7,338,760 B2 3/2008 Gong et al.
D566,291 S 4/2008 Parunak et al.
7,351,377 B2 4/2008 Chazan et al.
D569,526 S 5/2008 Duffy et al.
7,374,949 B2 5/2008 Kuriger
7,390,460 B2 6/2008 Osawa et al.
7,419,784 B2 9/2008 Dubrow et al.
7,422,669 B2 9/2008 Jacobson et al.
7,440,684 B2 10/2008 Spaid et al.
7,476,313 B2 1/2009 Siddiqi
7,494,577 B2 2/2009 Williams et al.
7,494,770 B2 2/2009 Wilding et al.
7,514,046 B2 4/2009 Kechagia et al.

(56) References Cited

U.S. PATENT DOCUMENTS

| | | | |
|---|---|---|---|
| 7,518,726 | B2 | 4/2009 | Rulison et al. |
| 7,521,186 | B2 | 4/2009 | Burd Mehta |
| 7,527,769 | B2 | 5/2009 | Bunch et al. |
| 7,553,671 | B2 | 6/2009 | Sinclair et al. |
| D596,312 | S | 7/2009 | Giraud et al. |
| 7,595,197 | B2 | 9/2009 | Brasseur |
| 7,604,938 | B2 | 10/2009 | Takahashi et al. |
| 7,635,588 | B2 | 12/2009 | King et al. |
| 7,645,581 | B2 | 1/2010 | Knapp et al. |
| 7,670,559 | B2 | 3/2010 | Chien et al. |
| 7,674,431 | B2 | 3/2010 | Ganesan |
| 7,704,735 | B2 | 4/2010 | Facer et al. |
| 7,723,123 | B1 | 5/2010 | Murphy et al. |
| D618,820 | S | 6/2010 | Wilson et al. |
| 7,727,371 | B2 | 6/2010 | Kennedy et al. |
| 7,727,477 | B2 | 6/2010 | Boronkay et al. |
| 7,744,817 | B2 | 6/2010 | Bui |
| D621,060 | S | 8/2010 | Handique |
| 7,867,776 | B2 | 1/2011 | Kennedy et al. |
| 7,892,819 | B2 | 2/2011 | Wilding et al. |
| D637,737 | S | 5/2011 | Wilson et al. |
| 7,998,708 | B2 | 8/2011 | Handique et al. |
| 8,088,616 | B2 | 1/2012 | Handique |
| 8,105,783 | B2 | 1/2012 | Handique |
| 8,110,158 | B2 | 2/2012 | Handique |
| 8,133,671 | B2 | 3/2012 | Williams et al. |
| 8,182,763 | B2 | 5/2012 | Duffy et al. |
| 8,273,308 | B2 | 9/2012 | Handique et al. |
| D669,597 | S | 10/2012 | Cavada et al. |
| 8,287,820 | B2 | 10/2012 | Williams et al. |
| 8,323,584 | B2 | 12/2012 | Ganesan |
| 8,323,900 | B2 | 12/2012 | Handique et al. |
| 8,324,372 | B2 | 12/2012 | Brahmasandra et al. |
| 8,415,103 | B2 | 4/2013 | Handique |
| 8,420,015 | B2 | 4/2013 | Ganesan et al. |
| 8,440,149 | B2 | 5/2013 | Handique |
| 8,470,586 | B2 | 6/2013 | Wu et al. |
| 8,473,104 | B2 | 6/2013 | Handique et al. |
| D692,162 | S | 10/2013 | Lentz et al. |
| 8,679,831 | B2 | 3/2014 | Handique et al. |
| 8,685,341 | B2 | 4/2014 | Ganesan |
| 8,703,069 | B2 | 4/2014 | Handique et al. |
| 8,709,787 | B2 | 4/2014 | Handique |
| 8,710,211 | B2 | 4/2014 | Brahmasandra et al. |
| 8,734,733 | B2 | 5/2014 | Handique |
| 8,765,076 | B2 | 7/2014 | Handique et al. |
| 8,852,862 | B2 | 10/2014 | Wu et al. |
| 8,883,490 | B2 | 11/2014 | Handique et al. |
| 8,894,947 | B2 | 11/2014 | Ganesan et al. |
| 8,895,311 | B1 | 11/2014 | Handique et al. |
| 9,028,773 | B2 | 5/2015 | Ganesan |
| 9,040,288 | B2 | 5/2015 | Handique et al. |
| 9,051,604 | B2 | 6/2015 | Handique |
| 9,080,207 | B2 | 7/2015 | Handique et al. |
| D742,027 | S | 10/2015 | Lentz et al. |
| 9,186,677 | B2 | 11/2015 | Williams et al. |
| 2001/0005489 | A1 | 6/2001 | Roach et al. |
| 2001/0012492 | A1 | 8/2001 | Acosta et al. |
| 2001/0016358 | A1* | 8/2001 | Osawa .................. B01L 3/0217 436/180 |
| 2001/0021355 | A1 | 9/2001 | Baugh et al. |
| 2001/0023848 | A1 | 9/2001 | Gjerde et al. |
| 2001/0038450 | A1 | 11/2001 | McCaffrey et al. |
| 2001/0046702 | A1 | 11/2001 | Schmebri |
| 2001/0048899 | A1* | 12/2001 | Marouiss et al. ............. 422/100 |
| 2001/0055765 | A1 | 12/2001 | O'Keefe et al. |
| 2002/0001848 | A1 | 1/2002 | Bedingham et al. |
| 2002/0008053 | A1 | 1/2002 | Hansen et al. |
| 2002/0009015 | A1 | 1/2002 | Laugharn et al. |
| 2002/0014443 | A1 | 2/2002 | Hansen et al. |
| 2002/0015667 | A1 | 2/2002 | Chow |
| 2002/0021983 | A1 | 2/2002 | Comte et al. |
| 2002/0037499 | A1 | 3/2002 | Quake et al. |
| 2002/0039783 | A1 | 4/2002 | McMillan et al. |
| 2002/0053399 | A1 | 5/2002 | Soane et al. |
| 2002/0054835 | A1 | 5/2002 | Robotti et al. |
| 2002/0055167 | A1 | 5/2002 | Pourahmadi et al. |
| 2002/0058332 | A1 | 5/2002 | Quake et al. |
| 2002/0060156 | A1 | 5/2002 | Mathies et al. |
| 2002/0068357 | A1 | 6/2002 | Mathies et al. |
| 2002/0131903 | A1* | 9/2002 | Ingenhoven ............ B01L 3/021 422/510 |
| 2002/0141903 | A1 | 10/2002 | Parunak et al. |
| 2002/0142471 | A1 | 10/2002 | Handique et al. |
| 2002/0143297 | A1 | 10/2002 | Francavilla et al. |
| 2002/0143437 | A1 | 10/2002 | Handique et al. |
| 2002/0155477 | A1 | 10/2002 | Ito |
| 2002/0169518 | A1 | 11/2002 | Luoma et al. |
| 2002/0187557 | A1 | 12/2002 | Hobbs et al. |
| 2002/0192808 | A1 | 12/2002 | Gambini et al. |
| 2003/0019522 | A1 | 1/2003 | Parunak |
| 2003/0022392 | A1 | 1/2003 | Hudak |
| 2003/0049174 | A1 | 3/2003 | Ganesan |
| 2003/0049833 | A1 | 3/2003 | Chen et al. |
| 2003/0059823 | A1 | 3/2003 | Matsunaga et al. |
| 2003/0064507 | A1 | 4/2003 | Gallagher et al. |
| 2003/0070677 | A1 | 4/2003 | Handique et al. |
| 2003/0072683 | A1 | 4/2003 | Stewart et al. |
| 2003/0073106 | A1 | 4/2003 | Johansen et al. |
| 2003/0083686 | A1 | 5/2003 | Freeman et al. |
| 2003/0087300 | A1 | 5/2003 | Knapp et al. |
| 2003/0096310 | A1 | 5/2003 | Hansen et al. |
| 2003/0127327 | A1 | 7/2003 | Kurnik |
| 2003/0136679 | A1 | 7/2003 | Bohn et al. |
| 2003/0186295 | A1 | 10/2003 | Colin et al. |
| 2003/0190608 | A1 | 10/2003 | Blackburn et al. |
| 2003/0199081 | A1 | 10/2003 | Wilding et al. |
| 2003/0211517 | A1 | 11/2003 | Carulli et al. |
| 2004/0014202 | A1 | 1/2004 | King et al. |
| 2004/0014238 | A1 | 1/2004 | Krug et al. |
| 2004/0018119 | A1* | 1/2004 | Massaro ....................... 422/100 |
| 2004/0022689 | A1 | 2/2004 | Wulf et al. |
| 2004/0029258 | A1 | 2/2004 | Heaney et al. |
| 2004/0029260 | A1 | 2/2004 | Hansen et al. |
| 2004/0037739 | A1 | 2/2004 | McNeely et al. |
| 2004/0053290 | A1 | 3/2004 | Terbrueggen et al. |
| 2004/0063217 | A1 | 4/2004 | Webster et al. |
| 2004/0072278 | A1 | 4/2004 | Chou et al. |
| 2004/0072375 | A1 | 4/2004 | Gjerde et al. |
| 2004/0086427 | A1 | 5/2004 | Childers et al. |
| 2004/0086956 | A1 | 5/2004 | Bachur, Jr. |
| 2004/0151629 | A1 | 8/2004 | Pease et al. |
| 2004/0157220 | A1 | 8/2004 | Kurnool et al. |
| 2004/0161788 | A1 | 8/2004 | Chen et al. |
| 2004/0189311 | A1 | 9/2004 | Glezer et al. |
| 2004/0200909 | A1 | 10/2004 | McMillan et al. |
| 2004/0209331 | A1 | 10/2004 | Ririe |
| 2004/0209354 | A1 | 10/2004 | Mathies et al. |
| 2004/0219070 | A1 | 11/2004 | Handique |
| 2004/0224317 | A1 | 11/2004 | Kordunsky et al. |
| 2004/0235154 | A1 | 11/2004 | Oh et al. |
| 2004/0240097 | A1 | 12/2004 | Evans |
| 2005/0009174 | A1 | 1/2005 | Nikiforov et al. |
| 2005/0013737 | A1 | 1/2005 | Chow et al. |
| 2005/0037471 | A1 | 2/2005 | Liu et al. |
| 2005/0041525 | A1 | 2/2005 | Pugia et al. |
| 2005/0042639 | A1 | 2/2005 | Knapp et al. |
| 2005/0048540 | A1 | 3/2005 | Inami et al. |
| 2005/0058574 | A1 | 3/2005 | Bysouth et al. |
| 2005/0058577 | A1 | 3/2005 | Micklash et al. |
| 2005/0064535 | A1 | 3/2005 | Favuzzi et al. |
| 2005/0069898 | A1 | 3/2005 | Moon et al. |
| 2005/0084424 | A1 | 4/2005 | Ganesan et al. |
| 2005/0106066 | A1 | 5/2005 | Saltsman et al. |
| 2005/0121324 | A1 | 6/2005 | Park et al. |
| 2005/0129580 | A1 | 6/2005 | Swinehart et al. |
| 2005/0133370 | A1 | 6/2005 | Park et al. |
| 2005/0135655 | A1 | 6/2005 | Kopf-sill et al. |
| 2005/0142036 | A1 | 6/2005 | Kim et al. |
| 2005/0152808 | A1 | 7/2005 | Ganesan |
| 2005/0170362 | A1 | 8/2005 | Wada et al. |
| 2005/0186585 | A1 | 8/2005 | Juncosa et al. |
| 2005/0202470 | A1 | 9/2005 | Sundberg et al. |
| 2005/0202504 | A1 | 9/2005 | Anderson et al. |

(56) References Cited

U.S. PATENT DOCUMENTS

| | | | |
|---|---|---|---|
| 2005/0208676 | A1 | 9/2005 | Kahatt |
| 2005/0214172 | A1 | 9/2005 | Burgisser |
| 2005/0220675 | A1 | 10/2005 | Reed et al. |
| 2005/0227269 | A1 | 10/2005 | Lloyd et al. |
| 2005/0233370 | A1 | 10/2005 | Ammann et al. |
| 2005/0238545 | A1 | 10/2005 | Parce et al. |
| 2005/0272079 | A1 | 12/2005 | Burns et al. |
| 2006/0041058 | A1 | 2/2006 | Yin et al. |
| 2006/0057039 | A1 | 3/2006 | Morse et al. |
| 2006/0057629 | A1 | 3/2006 | Kim |
| 2006/0062696 | A1 | 3/2006 | Chow et al. |
| 2006/0094108 | A1 | 5/2006 | Yoder et al. |
| 2006/0113190 | A1 | 6/2006 | Kurnik |
| 2006/0133965 | A1 | 6/2006 | Tajima et al. |
| 2006/0134790 | A1 | 6/2006 | Tanaka et al. |
| 2006/0148063 | A1 | 7/2006 | Fauzzi et al. |
| 2006/0165558 | A1 | 7/2006 | Witty et al. |
| 2006/0165559 | A1 | 7/2006 | Greenstein et al. |
| 2006/0166233 | A1 | 7/2006 | Wu et al. |
| 2006/0177376 | A1 | 8/2006 | Tomalia et al. |
| 2006/0177855 | A1 | 8/2006 | Utermohlen et al. |
| 2006/0183216 | A1 | 8/2006 | Handique |
| 2006/0201887 | A1 | 9/2006 | Siddiqi |
| 2006/0205085 | A1 | 9/2006 | Handique et al. |
| 2006/0207944 | A1 | 9/2006 | Siddiqi |
| 2006/0210435 | A1 | 9/2006 | Alavie et al. |
| 2006/0246493 | A1 | 11/2006 | Jensen et al. |
| 2006/0246533 | A1 | 11/2006 | Fathollahi et al. |
| 2006/0269961 | A1 | 11/2006 | Fukushima et al. |
| 2007/0004028 | A1 | 1/2007 | Lair et al. |
| 2007/0009386 | A1 | 1/2007 | Padmanabhan et al. |
| 2007/0020699 | A1 | 1/2007 | Carpenter et al. |
| 2007/0026421 | A1 | 2/2007 | Sundberg et al. |
| 2007/0042441 | A1 | 2/2007 | Masters et al. |
| 2007/0077648 | A1 | 4/2007 | Okamoto et al. |
| 2007/0092901 | A1 | 4/2007 | Ligler et al. |
| 2007/0098600 | A1 | 5/2007 | Kayyem et al. |
| 2007/0099200 | A1 | 5/2007 | Chow et al. |
| 2007/0104617 | A1 | 5/2007 | Coulling et al. |
| 2007/0116613 | A1 | 5/2007 | Elsener |
| 2007/0154895 | A1 | 7/2007 | Spaid et al. |
| 2007/0177147 | A1 | 8/2007 | Parce |
| 2007/0178607 | A1 | 8/2007 | Prober et al. |
| 2007/0184463 | A1 | 8/2007 | Molho et al. |
| 2007/0184547 | A1 | 8/2007 | Handique et al. |
| 2007/0196237 | A1 | 8/2007 | Neuzil et al. |
| 2007/0196238 | A1 | 8/2007 | Kennedy et al. |
| 2007/0199821 | A1 | 8/2007 | Chow |
| 2007/0215554 | A1 | 9/2007 | Kreuwel et al. |
| 2007/0218459 | A1 | 9/2007 | Miller et al. |
| 2007/0231213 | A1 | 10/2007 | Prabhu et al. |
| 2007/0243626 | A1 | 10/2007 | Windeyer et al. |
| 2007/0261479 | A1 | 11/2007 | Spaid et al. |
| 2007/0269861 | A1 | 11/2007 | Williams et al. |
| 2007/0292941 | A1 | 12/2007 | Handique et al. |
| 2008/0000774 | A1 | 1/2008 | Park et al. |
| 2008/0003649 | A1 | 1/2008 | Maltezos et al. |
| 2008/0017306 | A1 | 1/2008 | Liu et al. |
| 2008/0050804 | A1 | 2/2008 | Handique et al. |
| 2008/0069729 | A1 | 3/2008 | McNeely |
| 2008/0075634 | A1 | 3/2008 | Herchenbach et al. |
| 2008/0090244 | A1 | 4/2008 | Knapp et al. |
| 2008/0095673 | A1 | 4/2008 | Xu |
| 2008/0118987 | A1 | 5/2008 | Eastwood et al. |
| 2008/0124723 | A1 | 5/2008 | Dale et al. |
| 2008/0149840 | A1 | 6/2008 | Handique et al. |
| 2008/0160601 | A1 | 7/2008 | Handique |
| 2008/0182301 | A1 | 7/2008 | Handique et al. |
| 2008/0192254 | A1 | 8/2008 | Kim et al. |
| 2008/0226502 | A1 | 9/2008 | Jonsmann et al. |
| 2008/0247914 | A1 | 10/2008 | Edens et al. |
| 2008/0262213 | A1 | 10/2008 | Wu et al. |
| 2009/0047180 | A1 | 2/2009 | Kawahara |
| 2009/0047713 | A1 | 2/2009 | Handique |
| 2009/0129978 | A1 | 5/2009 | Wilson et al. |
| 2009/0130719 | A1 | 5/2009 | Handique |
| 2009/0130745 | A1 | 5/2009 | Williams et al. |
| 2009/0131650 | A1 | 5/2009 | Brahmasandra et al. |
| 2009/0134069 | A1 | 5/2009 | Handique |
| 2009/0136385 | A1 | 5/2009 | Handique et al. |
| 2009/0136386 | A1 | 5/2009 | Duffy et al. |
| 2009/0155123 | A1 | 6/2009 | Williams et al. |
| 2009/0189089 | A1 | 7/2009 | Bedingham et al. |
| 2009/0223925 | A1 | 9/2009 | Morse et al. |
| 2010/0009351 | A1 | 1/2010 | Brahmasandra et al. |
| 2010/0173393 | A1 | 7/2010 | Handique et al. |
| 2010/0284864 | A1 | 11/2010 | Holenstein et al. |
| 2011/0008825 | A1 | 1/2011 | Ingber et al. |
| 2011/0027151 | A1 | 2/2011 | Handique et al. |
| 2011/0158865 | A1 | 6/2011 | Miller et al. |
| 2011/0207140 | A1 | 8/2011 | Handique et al. |
| 2011/0210257 | A9 | 9/2011 | Handique et al. |
| 2012/0022695 | A1 | 1/2012 | Handique et al. |
| 2012/0085416 | A1 | 4/2012 | Ganesan |
| 2012/0122108 | A1 | 5/2012 | Handique |
| 2012/0160826 | A1 | 6/2012 | Handique |
| 2012/0171759 | A1 | 7/2012 | Williams et al. |
| 2012/0183454 | A1 | 7/2012 | Handique |
| 2012/0258463 | A1 | 10/2012 | Duffy et al. |
| 2013/0071851 | A1 | 3/2013 | Handique et al. |
| 2013/0096292 | A1 | 4/2013 | Brahmasandra et al. |
| 2013/0101990 | A1 | 4/2013 | Handique et al. |
| 2013/0164832 | A1 | 6/2013 | Ganesan et al. |
| 2013/0183769 | A1 | 7/2013 | Tajima |
| 2013/0217013 | A1 | 8/2013 | Steel et al. |
| 2013/0217102 | A1 | 8/2013 | Ganesan et al. |
| 2013/0251602 | A1 | 9/2013 | Handique et al. |
| 2013/0280131 | A1 | 10/2013 | Handique et al. |
| 2013/0288358 | A1 | 10/2013 | Handique et al. |
| 2014/0030798 | A1 | 1/2014 | Wu et al. |
| 2014/0045186 | A1 | 2/2014 | Gubatayao et al. |
| 2014/0206088 | A1 | 7/2014 | Lentz et al. |
| 2014/0212882 | A1 | 7/2014 | Handique et al. |
| 2014/0227710 | A1 | 8/2014 | Handique et al. |
| 2014/0297047 | A1 | 10/2014 | Ganesan et al. |
| 2014/0323357 | A1 | 10/2014 | Handique et al. |
| 2014/0323711 | A1 | 10/2014 | Brahmasandra et al. |
| 2014/0329301 | A1 | 11/2014 | Handique et al. |
| 2014/0342352 | A1 | 11/2014 | Handique et al. |
| 2014/0377850 | A1 | 12/2014 | Handique et al. |
| 2015/0064702 | A1 | 3/2015 | Handique et al. |
| 2015/0118684 | A1 | 4/2015 | Wu et al. |
| 2015/0133345 | A1 | 5/2015 | Handique et al. |
| 2015/0142186 | A1 | 5/2015 | Handique et al. |
| 2015/0152477 | A1 | 6/2015 | Ganesan et al. |
| 2015/0315631 | A1 | 11/2015 | Handique et al. |
| 2015/0328638 | A1 | 11/2015 | Handique et al. |

FOREIGN PATENT DOCUMENTS

| | | | |
|---|---|---|---|
| DE | 19929734 | | 12/1999 |
| DE | 19833293 | C1 | 1/2000 |
| EP | 0365828 | A2 | 5/1990 |
| EP | 0483620 | A2 | 5/1992 |
| EP | 0688602 | A2 | 12/1995 |
| EP | 0766256 | | 4/1997 |
| EP | 1077086 | A2 | 2/2001 |
| EP | 1346772 | A2 | 9/2003 |
| EP | 1541237 | A2 | 6/2005 |
| EP | 1574586 | A2 | 9/2005 |
| EP | 1792656 | A1 | 6/2007 |
| EP | 2372367 | A1 | 10/2011 |
| FR | 2672301 | | 8/1992 |
| FR | 2795426 | | 12/2000 |
| GB | 2453432 | A | 4/2009 |
| JP | S50-100881 | | 8/1975 |
| JP | 58212921 | A | 12/1983 |
| JP | S62-119460 | | 5/1987 |
| JP | H01-502319 | | 8/1989 |
| JP | 04-053555 | U | 5/1992 |
| JP | 06-064156 | U | 9/1994 |
| JP | 07-020010 | | 1/1995 |
| JP | H07-290706 | | 11/1995 |
| JP | H08-122336 | | 5/1996 |

(56) References Cited

FOREIGN PATENT DOCUMENTS

| | | | |
|---|---|---|---|
| JP | H08-211071 | | 8/1996 |
| JP | H08-285859 | | 11/1996 |
| JP | H09-325151 | | 12/1997 |
| JP | H11-515106 | | 12/1999 |
| JP | 2000-180455 | | 6/2000 |
| JP | 2000-275255 | | 10/2000 |
| JP | 2001-502319 | | 2/2001 |
| JP | 2001-509437 | | 7/2001 |
| JP | 3191150 | B2 | 7/2001 |
| JP | 2001-515216 | | 9/2001 |
| JP | 2001-527220 | | 12/2001 |
| JP | 2002-503331 | | 1/2002 |
| JP | 2002-085961 | | 3/2002 |
| JP | 2002-517735 | | 6/2002 |
| JP | 2002-215241 | | 7/2002 |
| JP | 2002-544476 | | 12/2002 |
| JP | 2003-500674 | | 1/2003 |
| JP | 2003-047839 | A | 2/2003 |
| JP | 2003-047840 | A | 2/2003 |
| JP | 2003-516125 | | 5/2003 |
| JP | 2003-185584 | | 7/2003 |
| JP | 2003-299485 | | 10/2003 |
| JP | 2003-329693 | | 11/2003 |
| JP | 2004-506179 | A | 2/2004 |
| JP | 2004-150797 | A | 5/2004 |
| JP | 2004-531360 | A | 10/2004 |
| JP | 2004-533838 | | 11/2004 |
| JP | 2004-361421 | | 12/2004 |
| JP | 2004-536291 | | 12/2004 |
| JP | 2005-009870 | | 1/2005 |
| JP | 2005-511264 | | 4/2005 |
| JP | 2005-514718 | | 5/2005 |
| JP | 2005-518825 | | 6/2005 |
| JP | 2005-176613 | A | 7/2005 |
| JP | 2005-192554 | | 7/2005 |
| JP | 2005-204661 | | 8/2005 |
| JP | 2005-525816 | | 9/2005 |
| JP | 2005-291954 | A | 10/2005 |
| JP | 2005-532043 | | 10/2005 |
| JP | 2005-323519 | | 11/2005 |
| JP | 2006-021156 | A | 1/2006 |
| JP | 2006-094866 | A | 4/2006 |
| JP | 2006-167569 | | 6/2006 |
| JP | 2007-074960 | | 3/2007 |
| JP | 2007-097477 | | 4/2007 |
| JP | 2007-510518 | | 4/2007 |
| JP | 2007-514405 | A | 6/2007 |
| JP | 2007-178328 | | 7/2007 |
| WO | WO 88/06633 | | 9/1988 |
| WO | WO 90/12350 | | 10/1990 |
| WO | WO 92/05443 | | 4/1992 |
| WO | WO 94/11103 | | 5/1994 |
| WO | WO 96/04547 | | 2/1996 |
| WO | WO 97/05492 | | 2/1997 |
| WO | WO 97/21090 | | 6/1997 |
| WO | WO 98/00231 | | 1/1998 |
| WO | WO 98/22625 | | 5/1998 |
| WO | WO 98/35013 | A1 | 8/1998 |
| WO | WO 98/49548 | | 11/1998 |
| WO | WO 98/53311 | | 11/1998 |
| WO | WO 99/01688 | | 1/1999 |
| WO | WO 99/09042 | | 2/1999 |
| WO | WO 99/12016 | | 3/1999 |
| WO | WO 99/33559 | | 7/1999 |
| WO | WO 01/05510 | | 1/2001 |
| WO | WO 01/14931 | | 3/2001 |
| WO | WO 01/27614 | | 4/2001 |
| WO | WO 01/28684 | | 4/2001 |
| WO | WO 01/41931 | | 6/2001 |
| WO | WO 01/54813 | | 8/2001 |
| WO | WO 01/89681 | | 11/2001 |
| WO | WO 02/072264 | | 9/2002 |
| WO | WO 02/078845 | | 10/2002 |
| WO | WO 03/007677 | | 1/2003 |
| WO | WO 03/012325 | | 2/2003 |
| WO | WO 03/012406 | | 2/2003 |
| WO | WO 03/048295 | | 6/2003 |
| WO | WO 03/055605 | | 7/2003 |
| WO | WO 03/076661 | | 9/2003 |
| WO | WO 2004/007081 | | 1/2004 |
| WO | WO 2004/048545 | | 6/2004 |
| WO | WO 2004/055522 | | 7/2004 |
| WO | WO 2004/056485 | A1 | 7/2004 |
| WO | WO 2004/074848 | | 9/2004 |
| WO | WO 2004/094986 | | 11/2004 |
| WO | WO 2005/011867 | | 2/2005 |
| WO | WO 2005/030984 | | 4/2005 |
| WO | WO 2005/107947 | | 11/2005 |
| WO | WO 2005/108571 | | 11/2005 |
| WO | WO 2005/108620 | | 11/2005 |
| WO | WO 2005/116202 | | 12/2005 |
| WO | WO 2005/118867 | | 12/2005 |
| WO | WO 2005/120710 | | 12/2005 |
| WO | WO 2006/010584 | | 2/2006 |
| WO | WO 2006/032044 | | 3/2006 |
| WO | WO 2006/035800 | | 4/2006 |
| WO | WO 2006/043642 | | 4/2006 |
| WO | WO 2006/066001 | | 6/2006 |
| WO | WO 2006/079082 | | 7/2006 |
| WO | WO 2006/113198 | | 10/2006 |
| WO | WO 2006/119280 | | 11/2006 |
| WO | WO 2007/044917 | | 4/2007 |
| WO | WO 2007/050327 | | 5/2007 |
| WO | WO 2007/064117 | | 6/2007 |
| WO | WO 2007/091530 | | 8/2007 |
| WO | WO 2007/112114 | | 10/2007 |
| WO | WO 2008/030914 | | 3/2008 |
| WO | WO 2009/012185 | | 1/2009 |
| WO | WO 2009/054870 | | 4/2009 |
| WO | WO 2010/118541 | | 10/2010 |
| WO | WO 2011/101467 | | 8/2011 |

OTHER PUBLICATIONS

Brahmasandra et al., On-chip DNA detection in microfabricated separation systems, SPIE Conference on Microfluidic Devices and Systems, 1998, vol. 3515, pp. 242-251, Santa Clara, CA.

Breadmore et al., "Microchip-Based Purification of DNA from Biological Samples", Anal. Chem., vol. 75 (2003), pp. 1880-1886.

Brody et al., Diffusion-Based Extraction in a Microfabricated Device, Sensors and Actuators Elsevier, 1997, vol. A58, No. 1, pp. 13-18.

Broyles et al., "Sample Filtration, Concentration, and Separation Integrated on Microfluidic Devices" Analytical Chemistry (American Chemical Society), (2003) vol. 75 No. 11: pp. 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung et al., "Microfluidic chip for high efficiency DNA extraction", Miniaturisation for Chemistry, Biology & Bioengineering, vol. 4, No. 2 (Apr. 2004), pp. 141-147.

Handique et al., On-Chip Thermopneumatic Pressure for Discrete Drop Pumping, Analytical Chemistry, American Chemical Society, Apr. 15, 2001, vol. 73, No. 8, 1831-1838.

Handique et al, "Microfluidic flow control using selective hydrophobic patterning", SPIE, vol. 3224, pp. 185-194 (1997).

Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique et al., "Mathematical Modeling of Drop Mixing in a Slit-Type Microchannel", J. Micromech. Microeng., 11:548-554 (2001).

Handique et al., "Nanoliter Liquid Metering in Microchannels Using Hydrophobic Patterns", Anal. Chem., 72:4100-4109 (2000).

He et al., Microfabricated Filters for Microfluidic Analytical Systems, Analytical Chemistry, American Chemical Society, 1999, vol. 71, No. 7, pp. 1464-1468.

Ibrahim et al., Real-Time Microchip PCR for Detecting Single-Base Differences in Viral and Human DNA, Analytical Chemistry, American Chemical Society, 1998, vol. 70, No. 9, pp. 2013-2017.

(56) References Cited

OTHER PUBLICATIONS

Khandurina et al., Microfabricated Porous Membrane Structure for Sample Concentration and Electrophoretic Analysis, Analytical Chemistry American Chemical Society, 1999, vol. 71, No. 9, pp. 1815-1819.
Kopp et al., Chemical Amplification: Continuous-Flow PCR on a Chip, www.sciencemag.org, 1998, vol. 280, pp. 1046-1048.
Kutter et al., Solid Phase Extraction on Microfluidic Devices, J. Microcolumn Separations, John Wiley & Sons, Inc., 2000, vol. 12, No. 2, pp. 93-97.
Lagally et al., Single-Molecule DNA Amplification and Analysis in an Integrated Microfluidic Device, Analytical Chemistry, American Chemical Society, 2001, vol. 73, No. 3 pp. 565-570.
Livache et al., "Polypyrrole DNA chip on a Silicon Device: Example of Hepatitis C Virus Genotyping", Analytical Biochemistry, vol. 255 (1998), pp. 188-194.
Mascini et al., "DNA electrochemical biosensors", Fresenius J. Anal. Chem., 369: 15-22, (2001).
Nakagawa et al., Fabrication of amino silane-coated microchip for DNA extraction from whole blood, J of Biotechnology, Mar. 2, 2005, vol. 116, pp. 105-111.
Northrup et al., A Miniature Analytical Instrument for Nucleic Acids Based on Micromachined Silicon Reaction Chambers, Analytical Chemistry, American Chemical Society, 1998, vol. 70, No. 5, pp. 918-922.
Oleschuk et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.
Plambeck et al., "Electrochemical Studies of Antitumor Antibiotics", J. Electrochem Soc.: Electrochemical Science and Technology (1984), 131(11): 2556-2563.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.
Shoffner et al., Chip PCR.I. Surface Passivation of Microfabricated Silicon-Glass Chips for PCR, Nucleic Acids Research, Oxford University Press, 1996, vol. 24, No. 2, 375-379.
Smith et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Wang, "Survey and Summary, from DNA Biosensors to Gene Chips", Nucleic Acids Research, 28(16):3011-3016, (2000).
Waters et al., Microchip Device for Cell Lysis, Multiplex PCR Amplification, and Electrophoretic Sizing, Analytical Chemistry, American Chemical Society, 1998, vol. 70, No. 1, pp. 158-162.
Weigl et al., Microfluidic Diffusion-Based Separation and Detection, www.sciencemag.org, 1999, vol. 283, pp. 346-347.
Yoza et al., DNA extraction using bacterial magnetic particles modified with hyperbranched polyamidoamine dendrimer, Mar. 20, 2003, vol. 101, No. 3, 219-228.
Yoza et al., "Fully Automated DNA Extraction from Blood Using Magnetic Particles Modified with a Hyperbranched Polyamidomine Dendrimer", Journal of Bioscience and Bioengineering, 95(1):21-26, 2003.
International Search Report and Written Opinion dated Apr. 4, 2008 for PCT/US07/07513.
International Search Report and Written Opinion for PCT/US07/024022 dated Jan. 5, 2009.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Meyers, R.A., Molecular Biology and Biotechnology: A Comprehensive Desk Reference; VCH Publishers, Inc. New York, NY; (1995) pp. 418-419.
Popovic, Marko B. [Ed.] *Biomechanics and Robotics*; Pan Stanford Publishing (2014); Chapter 2 "Actuators," pp. 33-73.
Kuo et al., "Remnant cationic dendrimers block RNA migration in electrophoresis after monophasic lysis", J Biotech. (2007) 129: 383-390.
Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.
Wu et al., "Polycationic dendrimers interact with RNA molecules: polyamine dendrimers inhibit the catalytic activity of Candida ribozymes", Chem Commun. (2005) 3: 313-315.
Zhou et al., "Cooperative binding and self-assembling behavior of cationic low molecular-weight dendrons with RNA molecules", Org Biomol Chem. (2006) 4(3): 581-585.
Zhou et al., "PANAM dendrimers for efficient siRNA delivery and potent gene silencing", Chem Comm.(Camb.) (2006) 22: 2362-2364.
International Search Report dated Jun. 17, 2009 for Application No. PCT/US2008/008640, filed Jul. 14, 2008.
International Preliminary Report on Patentability and Written Opinion dated Jan. 19, 2010 for Application No. PCT/US2008/008640, filed Jul. 14, 2008.

* cited by examiner

AUTOMATED PIPETTING APPARATUS HAVING A COMBINED LIQUID PUMP AND PIPETTE HEAD SYSTEM

RELATED APPLICATIONS

This application is a continuation of U.S. patent application Ser. No. 12/212,403, filed on Sep. 17, 2008, which is a continuation-in-part of U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), and a continuation in part of U.S. patent application Ser. No. 12/218,498, filed on Jul. 14, 2008, both of which applications claim the benefit of priority to U.S. provisional patent application Ser. No. 60/959,437, filed Jul. 13, 2007, all of which are incorporated herein by reference in their entireties.

TECHNICAL FIELD

The technology described herein generally relates to systems and methods for controlling fluid processing operations associated with extracting polynucleotides from samples, particularly multiple biological samples in parallel. The technology more particularly relates to automated pipetting systems that operate in conjunction with reagent containers and carry out various suck and dispense operations on various reagents in the containers, thereby bringing about mixing or disposal of those reagents.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because of the number of reagents required, and the need for multiple liquid transfer (e.g., pipetting) operations. Thus, there is a need for an automated pipetting apparatus, particularly one that can operate on multiple samples in parallel.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The technology herein includes a liquid dispenser, comprising: one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps. The liquid dispenser further has a number of dispense heads, wherein each head is configured to accept a pipette tip.

The technology herein further includes an automated pipetting system that includes a liquid dispenser, the dispenser comprising: one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps.

The technology herein further includes an apparatus for carrying out sample preparation on multiple samples in parallel, the apparatus including an automated pipetting system configured to carry out liquid handling steps associated with sample preparation. The pipetting system includes a liquid dispenser, the dispenser comprising: one or more sensors; a manifold; one or more pumps in fluid communication with the manifold; one or more dispense heads in fluid communication with the manifold; and electrical connections that accept electrical signals from an external controller, wherein the liquid dispenser has no inlet or outlet for fluids, other than through the one or more pumps. The apparatus may further carry out diagnostic analysis on nucleotides put into form ready for amplification after sample preparation, where the automated pipetting system is configured to transfer those samples to a device that can amplify those samples and provide detectable quantities of amplified samples.

The technology herein further includes methods of sample preparation, comprising liquid handling steps that are performed on multiple samples in parallel by an automated pipetting system that includes a liquid dispenser as further described herein.

BRIEF DESCRIPTION OF THE DRAWINGS

Like reference numerals in the various drawings indicate like elements.

DETAILED DESCRIPTION

The automated pipetting apparatus described herein is typically configured for use in a method and apparatus for carrying out sample preparation on biological samples in parallel, with or without PCR and detection on the prepared samples, and preferably with high throughput.

Figure 1:
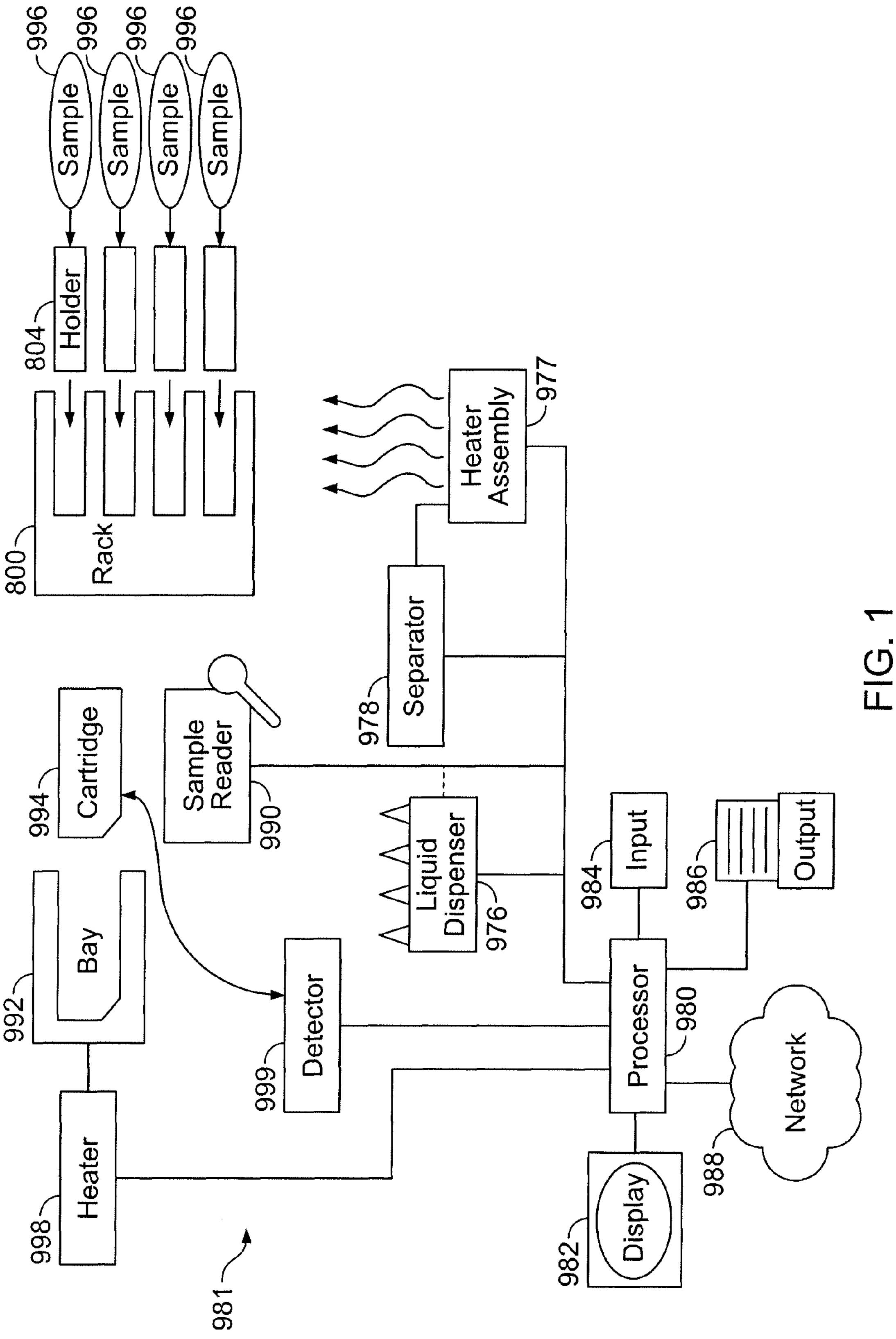
FIG. 1 shows a schematic of an automated apparatus configured to carry out sample preparation using a liquid dispenser as described herein.

Overview of a Preparatory or Diagnostic Apparatus that Incorporates a Liquid Dispenser A schematic overview of an apparatus 981 for carrying out automated sample preparation on multiple samples in parallel, according to steps exemplified elsewhere herein, is shown in FIG. 1. The geometric arrangement of the components of system 981 is exemplary and not intended to be limiting.

A processor 980, such as a microprocessor, is configured to control functions of various components of the system as shown, and is thereby in communication with each such component requiring control, for example via a bus. It is to be understood that many such control functions can optionally be carried out manually, and not under control of the processor. Furthermore, the order in which the various functions are described, in the following, is not limiting upon the order in which the processor executes instructions when the apparatus is operating. A suitable processor 980 can be designed and manufactured according to, respectively, design principles and semiconductor processing methods known in the art.

Processor 980 can be configured to accept user instructions from an input device 984, where such instructions may include instructions to start analyzing the sample, and choices of operating conditions. Processor 980 can be also configured to communicate with a display 982, so that, for example, information about an analysis is transmitted to the display and thereby communicated to a user of the system. Such information includes but is not limited to one or more of: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another.

Processor 980 can be optionally further configured to transmit results of an analysis to an output device 986 such as a printer, a visual display such as display 982 or a second display, a display that utilizes a holographic projection, or a speaker, or a combination thereof. Processor 980 can be still further optionally connected via a communication interface such as a network interface to a computer network 988.

Processor 980 can be further configured to control various aspects of sample preparation and diagnosis, as follows in overview. In FIG. 1, the apparatus 981 is configured to operate in conjunction with a complementary rack 970. Apparatus 981 may be capable of receiving multiple racks, such as 1, 2, 3, 4, or 6 racks.

Embodiments of rack 970 are further described in U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), and Ser. No. 12/178,584, filed on Jul. 23, 2008, and entitled "Rack For Sample Tubes And Reagent Holders", in the name of Duffy, et al., both of which are incorporated herein by reference in their entireties. A rack 970 is itself configured to receive a number of biological samples 996, such as nucleic-acid containing samples, in a form suitable for work-up and subsequent diagnostic analysis, and a number of holders 972—as further described herein, such as in connection with FIG. 2—that are equipped with various reagents, pipette tips and receptacles. The rack is configured so that, during sample work-up, samples are processed in the respective holders, the processing including being subjected, individually, to heating and cooling via heater assembly 977.

The heating functions of the heater assembly 977 can be controlled by the processor 980. Heater assembly 977 operates in conjunction with a separator 978, such as a magnetic separator, that also can be controlled by processor 980 to move into and out of close proximity to one or more processing chambers associated with the holders 972, wherein particles such as magnetic particles are present. Assembly 977 and separator 978 are further described in U.S. patent application Ser. No. 12/178,586, filed on Jul. 23, 2008, and entitled "Integrated Heater and Magnetic Separator", in the name of Handique, which is incorporated herein by reference in its entirety.

Processor 980 can be configured to receive data about a sample to be analyzed, e.g., from a sample reader 990, which may be a barcode reader, an optical character reader, or an RFID scanner (radio frequency tag reader). Thus, sample reader 990 is configured to transmit identifying indicia about the sample, and in some instances the holder, to processor 980. In some embodiments, the sample reader is movable from one sample position to another. In some embodiments a sample reader is attached to the liquid dispenser 976 and can thereby read indicia about a sample above which the liquid dispenser is situated. In other embodiments the sample reader is not attached to the liquid dispenser and is independently movable, under control of the processor.

Liquid dispenser 976, which similarly can be controlled by processor 980 and is further described herein, is configured to automatically carry out various pipetting (e.g., suck and dispense) operations on respective samples in rack 970, and fluids and reagents in the holders 972, to achieve extraction of nucleic acid from the samples. Liquid dispenser 976 can carry out such operations on multiple holders simultaneously, and is further described herein.

Liquid dispenser 976 is also configured to take aliquots of fluid containing nucleic acid extracted from one or more samples and direct them to a storage area (not shown in FIG. 1), which may comprise a cooler or coolers. Such a storage area may contain, for example, a PCR tube corresponding to each sample and which can contain solutions of extracted nucleic acids dispensed by the liquid dispenser.

In the embodiment of a diagnostic apparatus shown in FIG. 1, a cartridge 994 is received in bay 992. The receiving bay is in communication with a heater 998 that itself can be controlled by processor 980 in such a way that specific regions of the cartridge 994 are heated at specific times during analysis. Liquid dispenser 976 is thus configured to take aliquots of fluid containing nucleic acid extracted from one or more samples and direct them to one or more respective inlets in cartridge 994. Cartridge 994 is configured to amplify, such as by providing chambers for carrying out PCR on, the respective nucleic acids. Exemplary cartridges are found described in U.S. patent application Ser. No. 12/173,023, filed Jul. 14, 2008, and incorporated herein by reference. The processor is also configured to control and receive data from a detector 999 that receives an indication of a diagnosis from the cartridge 994. The diagnosis can be transmitted to the output device 986 and/or the display 982, as described hereinabove.

Embodiments of the apparatus shown in outline in FIG. 1, as with other exemplary embodiments described herein, are advantageous because they do not require locations within the apparatus suitably configured for storage of reagents. Therefore, the apparatus in FIG. 1 is self-contained and operates in conjunction with holders 972, wherein the holders are prepackaged with reagents, such as in locations within it dedicated to reagent storage.

The apparatus of FIG. 1 may be configured to carry out operation in a single location, such as a laboratory setting, or may be portable so that they can accompany, e.g., a physician, or other healthcare professional, who may visit patients at different locations. The apparatus is typically provided with a power-cord so that it can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 1 may further be configured, in other embodiments, for multiplexed sample analysis and/or analysis of multiple batches of samples, where, e.g., a single rack holds a single batch of samples. Each component shown in FIG. 1 may therefore be independently present as many times as there are batches of samples (or some fraction thereof), though the various components may be configured in a common housing.

In various embodiments, preparation of a PCR-ready sample for use in subsequent diagnosis using the apparatus as further described herein can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid); in some embodiments, the PCR reagent mixture can be in the form of one or more lyophilized pellets, as stored in a receptacle on a holder, and the method can further include reconstituting the PCR pellet with liquid to create a PCR reagent mixture solution.

The apparatuses as described herein find application to analyzing any nucleic acid containing sample for any purpose, including but not limited to genetic testing, and clinical testing for various infectious diseases in humans.

The apparatus herein can be configured to run on a laboratory benchtop, or similar environment, and can test approximately 45 samples per hour when run continuously throughout a normal working day. Results from individual raw samples are typically available in less than 1 hour.

Figure 2A:
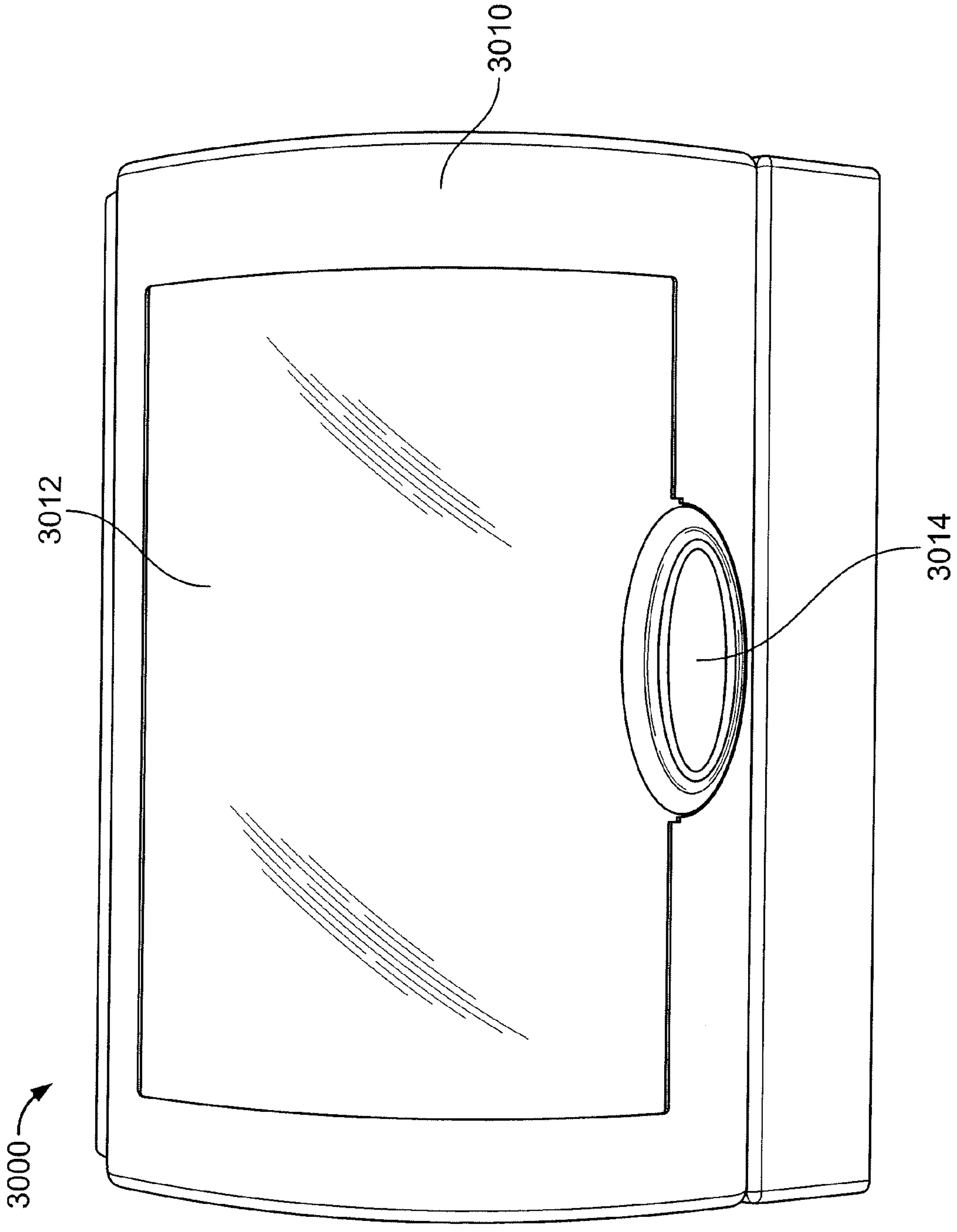
FIGS. 2A and 2B show views of the exterior and interior of an exemplary diagnostic apparatus.
Figure 2B:
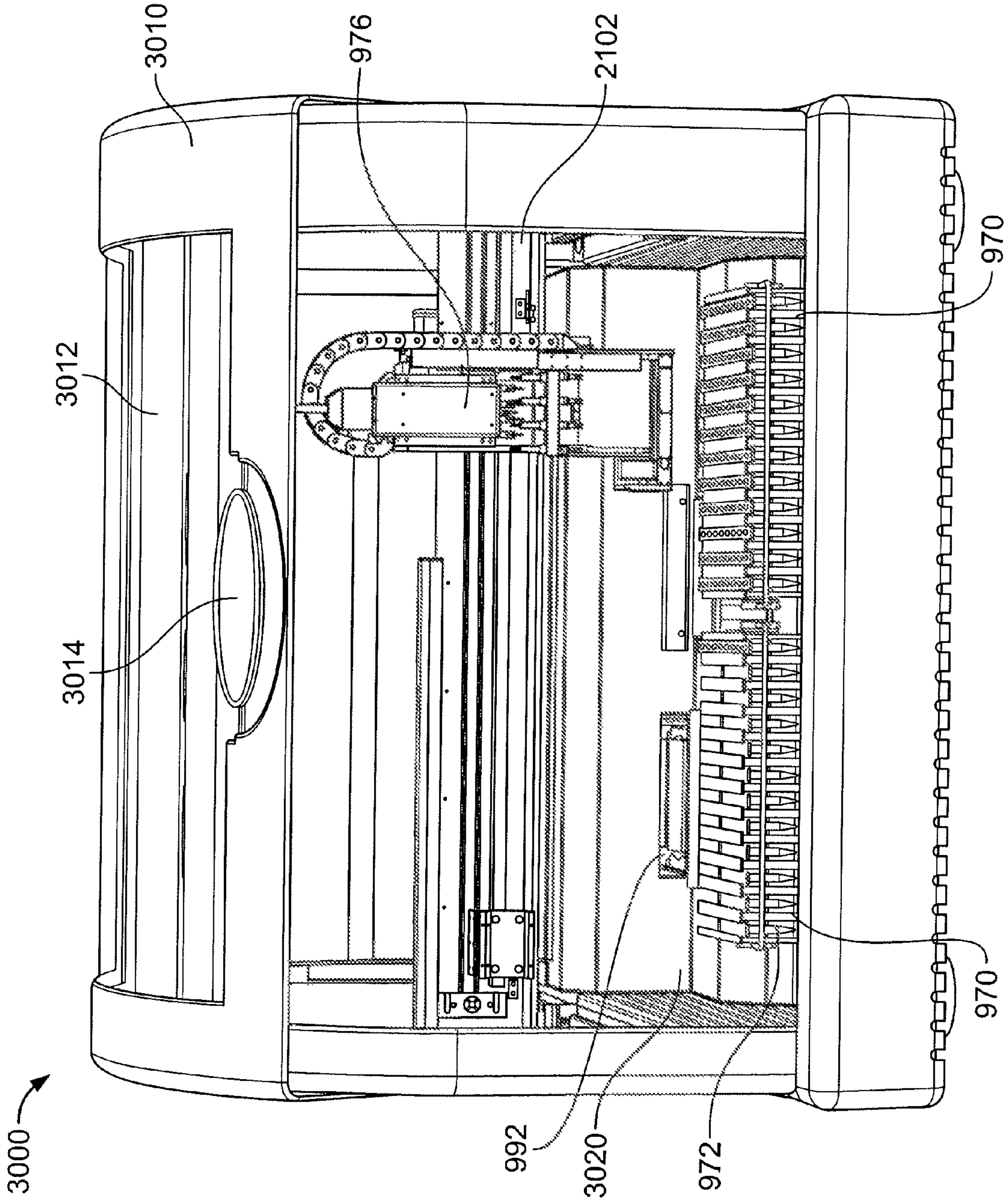

FIGS. 2A and 2B show views of an exemplary diagnostic apparatus 3000 incorporating various elements of FIG. 1. Shown in FIG. 2A, a front plan view of apparatus 3000 has a hinged cover 3010, shown in a closed position, bearing an optional clear window 3012 (that provides a user with an at-a-glance indication of the operational state of the apparatus), and a handle 3014 that facilitates opening and closing of the cover.

Shown in FIG. 2B is a front plan view of apparatus 3000 with cover 3010 moved to an open position revealing certain elements of the interior 3020 of the apparatus. Aspects of the interior of the apparatus that are visible in the view of FIG. 2B include: two removable racks 970, each bearing 12 holders 972, and a liquid dispenser 976, mounted on a gantry that can move along horizontal sliding rails 2102, as further described herein.

Reagent Holders

The automated diagnostic apparatus described herein is configured to carry out sample preparation on multiple samples by accessing more than one sample tube, and more than one reagent holder, simultaneously. Thus, the liquid dispense head, further described herein, is configured to extract and dispense volumes of liquid from various positions in one or more reagent holders, the holders being disposed in a suitably configured rack, as also described elsewhere herein.

Described herein are reagent holders for holding and transporting reagents for various purposes, in particular sample preparation in a clinical context, and configured to be received by a rack as described elsewhere herein. The reagent holders also typically provide a container, such as a process tube, in which various reagents can be mixed one with another and/or with a sample, and subjected to heating.

Exemplary reagent holders are further described in copending application Ser. No. 12/218,416, filed by Express-Mail on Jul. 14, 2008 (and entitled “Reagent Tube, Reagent Holder, and Kits Containing Same”, in the name of Wilson, et al.) and incorporated herein by reference.

Figure 3A:
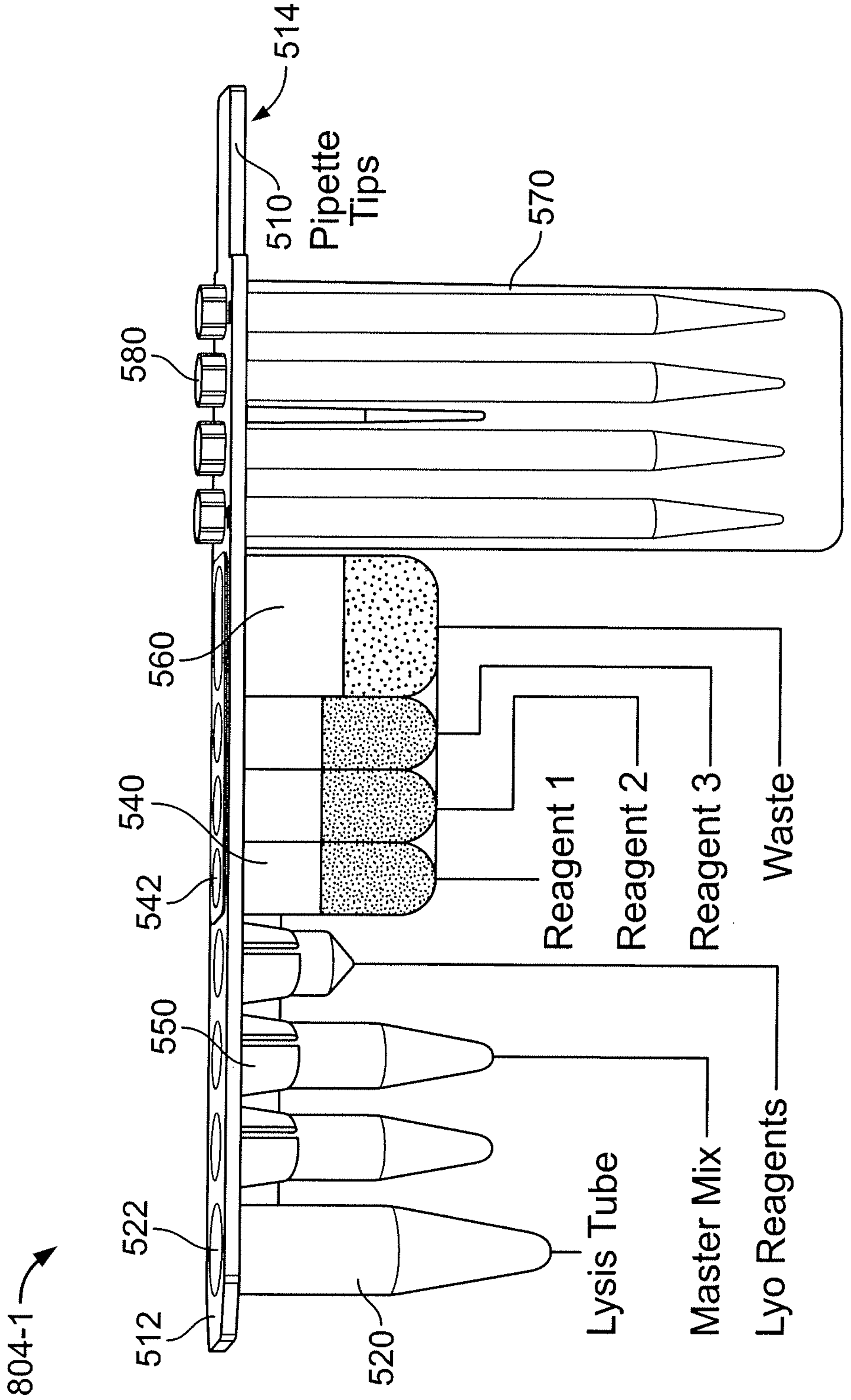
FIGS. 3A and 3B show an exemplary embodiment of a reagent holder, in side plan, and perspective, views.
Figure 3B:
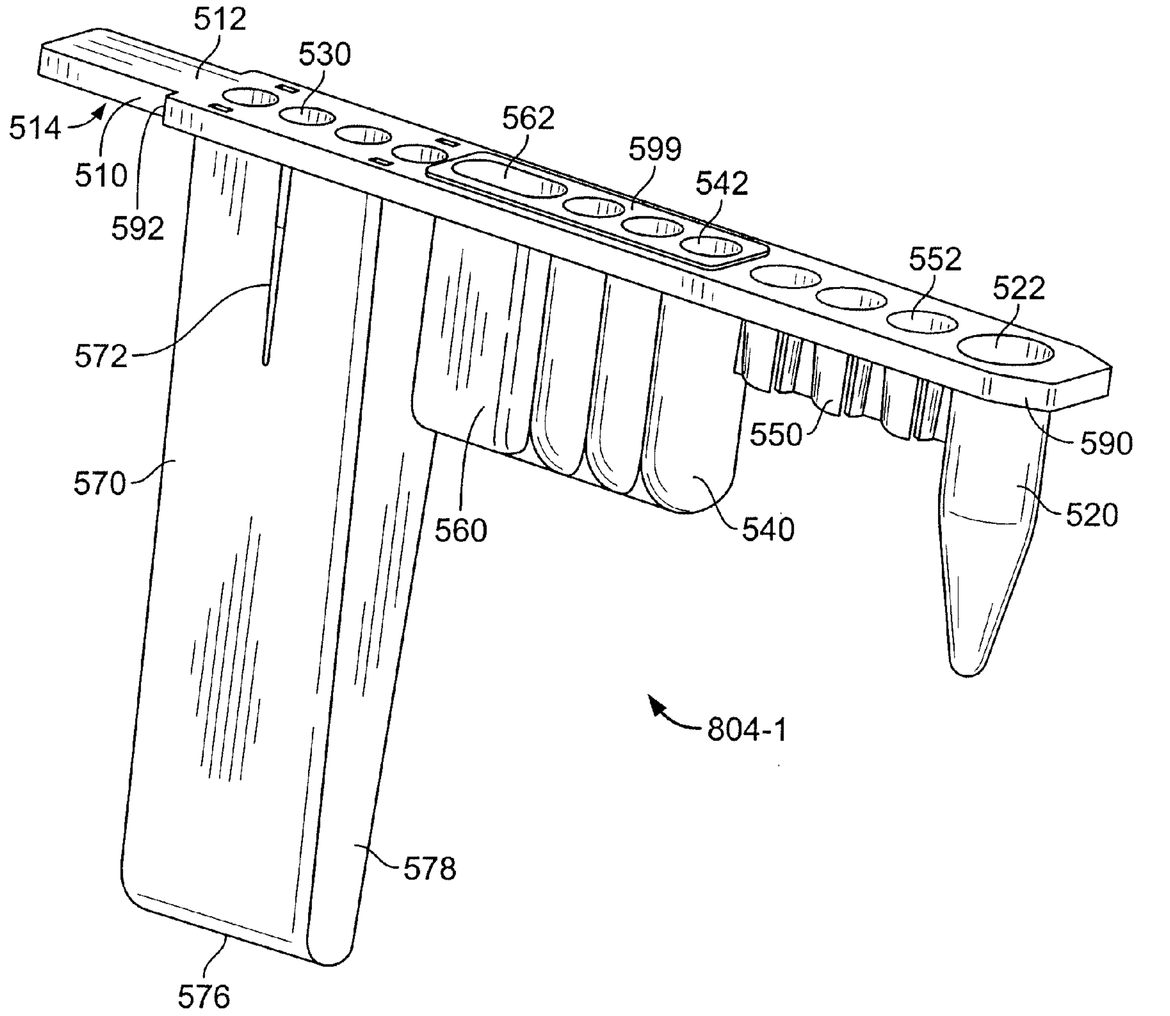
Figure 4:
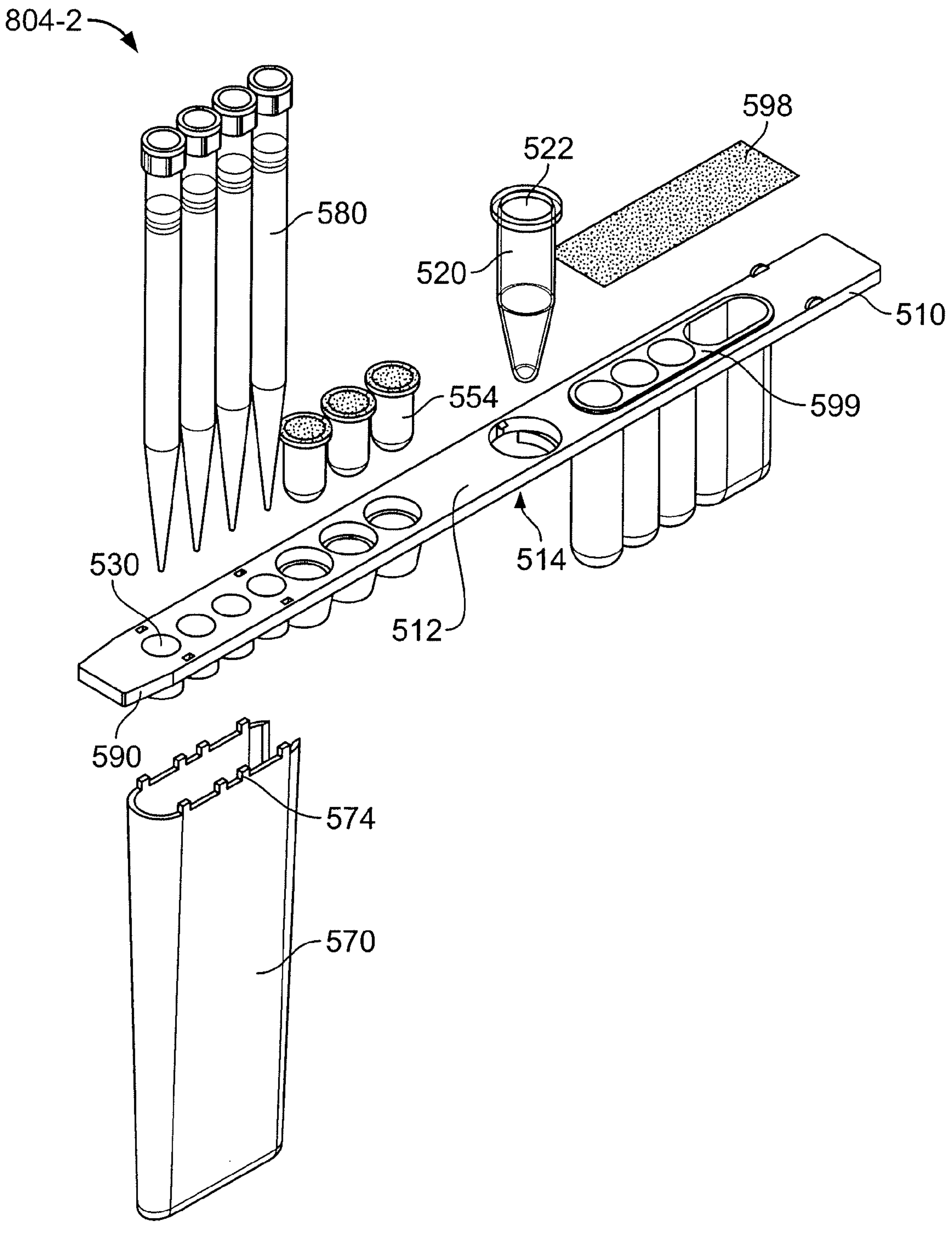
FIG. 4 shows a perspective view of a second exemplary embodiment of a reagent holder, in perspective view.

FIG. 3A shows a side plan view, and FIG. 3B shows a perspective view, of an exemplary holder 804-1 as further described herein. This exemplary holder, as well as others consistent with the written description herein though not shown as specific embodiments, are now described. FIG. 4 shows a second embodiment of a reagent holder 804-2, in perspective view, the holder having a different configuration of containers from that in FIGS. 3A and 3B. Like reference numerals in FIGS. 3A, 3B, and 4 refer to like elements in those respective figures. Holder embodiments 804-1 and 804-2 may be referred to collectively, herein as holder 804.

The exemplary holders of FIGS. 3A, 3B, and 4 comprise a connecting member 510 having one or more characteristics as follows. Connecting member 510 serves to connect various components of the holder together. Connecting member 510 has an upper side 512 and, opposed to the upper side, an underside 514.

The reagent holder of FIGS. 3A, 3B, and 4 are configured to comprise: a process tube 520 affixed to the connecting member and having an aperture 522 located in the connecting member; at least one socket 530, located in the connecting member, the socket configured to accept a disposable pipette tip 580; an optional pipette sheath 570 as further described herein; two or more reagent tubes 540 disposed on the underside of the connecting member, each of the reagent tubes having an inlet aperture 542 located in the connecting member; and one or more receptacles 550, located in the connecting member, wherein the one or more receptacles are each configured to receive a complementary container such as a reagent tube (not shown in FIG. 3B) inserted from the upper side 512 of the connecting member. Each of the apertures, and the corresponding openings of various complementary containers, is configured to accept a pipette tip, such as a standard laboratory pipette tip, during various pipetting operations such as dispensing fluid into, or sucking fluid out of, the one or more containers.

The one or more receptacles 550 are configured to accept container 554 that contain, respectively, sufficient quantities of one or more reagents typically in solid form, such as in lyophilized form, for carrying out extraction of nucleic acids from a sample that is associated with the holder. The receptacles can be all of the same size and shape, or may be of different sizes and shapes from one another. Preferably the receptacles 550 are configured to accept commonly used containers in the field of laboratory analysis, or containers suitably configured for use with the holder herein. The containers may be snap-in reagent tubes that maintain a steady position in the holder during pipetting operations thereon.

The containers that contain solid reagents such as lyophilized reagents, can be sealed across their tops by a metal foil, such as a single layer of an aluminum foil, with no plastic lining layer, as further described herein.

The containers containing different reagents may be of different colors, or color-coded for easy identification by the user. For example they may be made of different color material, such as tinted plastic, or may have some kind of identifying tag on them, such as a color stripe or dot. They may also have a label printed on the side, and/or may have an identifier such as a 1-D or a 2-D barcode on the sealing layer on the top, or on the side of the tube. Such a code is useful for identifying the composition of the reagents stored within, and/or a batch number for the preparation thereof, and/or an expiry date. The code may be printed on with, for example, an inkjet or transfer printer.

In one embodiment, the containers 554 containing lyophilized reagents, disposed in the receptacles 550, are 0.3 ml tubes that have been further configured to have a star-shaped pattern on their respective bottom interior surfaces. This is so that when a fluid has been added to the lyophilized reagents (which are dry in the initial package), a pipette tip can be bottomed out in the tube and still be able to withdraw almost the entire fluid from the tube. The design of the star-pattern is further described elsewhere in U.S. patent application Ser. No. 12/178,557, filed on Jul. 23, 2008, and entitled "Reagent Tube", in the name of Handique et al., which application is incorporated herein by reference. Still other containers used in conjunction with the holder herein may be similarly configured with a start-shaped pattern to increase pipetting efficiency.

The embodiments of reagent holders 804 are shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed.

The embodiments of reagent holders 804 are shown having a pipette sheath 570. This is an optional component of the holders described herein. It may be permanently or removably affixed to connecting member 510, or may be formed, e.g., moulded, as a part of a single piece assembly for the holder. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets. The sheath and sockets are large enough to accommodate a variety of sizes of pipette tips, such as those having volumes as small as 10 μl to as large as 1 ml.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. In embodiments of the reagent holder having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment having no pipette sheath, could utilize, e.g., a drip tray or a drainage outlet, suitably placed beneath pipette tips located in the one or more sockets, for the same purpose and located under or in the bottom of the rack, as described herein.

Process tube 520 (sometimes referred to as a lysis tube) can also be a snap-in tube, rather than being part of an integrated piece. Process tube 520 is typically used for various mixing and reacting processes that occur during sample preparation. For example, cell lysis can occur in process tube 520, as can extraction of nucleic acids, such as DNA or RNA of a patient, or DNA or RNA of a pathogen. Process tube 520 is then advantageously positioned in a location that minimizes, overall, pipette head moving operations involved with transferring liquids to process tube 520. Process tube 520 is also located in the holder in such a position that, when the holder is inserted in a rack as further described herein, the process tube is exposed and accessible to a heater and separator, as further described herein. The process tube is typically configured to accept a pipette tip during multiple pipetting operations.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

Some of the reagents contained in the holder are provided as liquids, and others may be provided as solids from which a solution is re-generated, in situ, by adding liquid from a pipette tip. In some embodiments, a different type of container or tube is used to store liquids from those that store the solids.

Reagent tubes 540 are typically configured to hold liquid reagents, one per tube. For example, in reagent holder embodiment 501, three reagent tubes are shown, containing respectively wash buffer, release buffer, and neutralization buffer, each of which is used in a sample preparation protocol, carried out with multiple pipetting operations controlled by, e.g., a pipette head as further described herein.

Reagent tubes 540 that hold liquids or liquid reagents can be sealed with a laminate structure 598. The laminate structure typically has a heat seal layer, a plastic layer such as a layer of polypropylene, and a layer of metal such as aluminum foil, wherein the heat seal layer is adjacent the one or more reagent tubes. The additional plastic film that is used in a laminate for receptacles that contain liquid reagents is typically to prevent liquid from contacting the aluminum.

Figure 5:
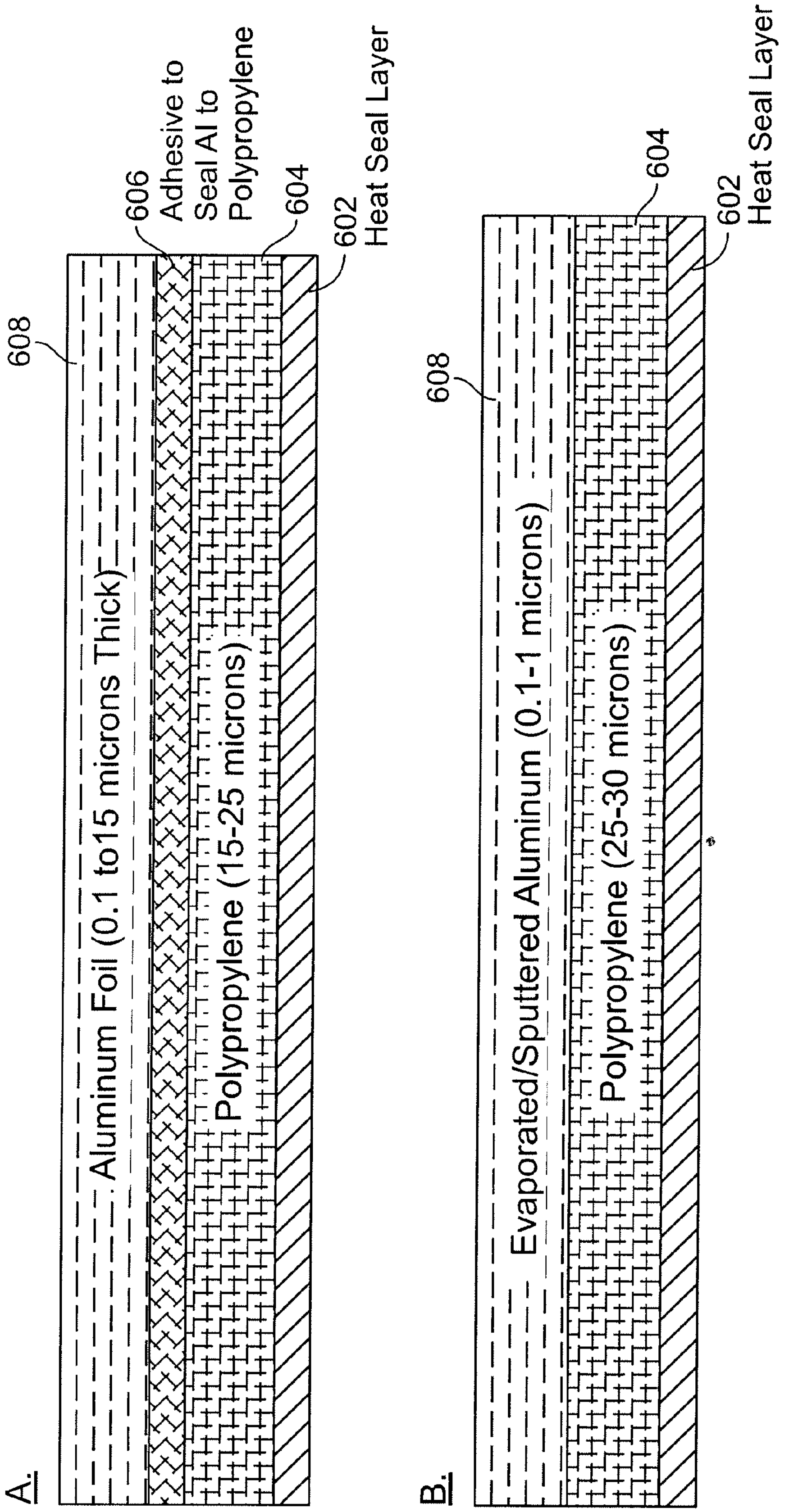
FIG. 5 shows embodiments of a laminated structures used to seal liquid containing tubes.

Two embodiments of a laminate structure, differing in their layer structures, are shown in FIG. 5. In both embodiments, the heat seal layer 602, for example made of a laquer or other such polymer with a low melting point, is at the bottom, adjacent to the top of the holder, when so applied. The plastic layer 604 is typically on top of the heat seal layer, and is typically made of polypropylene, having a thickness in the range 10-50 microns. The metal layer 608 is typically on top of the plastic layer and, in one embodiment, may be a layer of Al foil bonded to the plastic layer with a layer of adhesive 606, as in panel A of FIG. 5, or, in another embodiment, may be a layer of metal that is evaporated or sputtered into place directly on to the plastic layer (panel B of FIG. 5). Exemplary thicknesses for the respective layers are shown in FIG. 5, where it is to be understood that variations of up to a factor of 2 in thickness are consistent with the technology herein. In particular, the aluminum foil is 0.1-15 microns thick, and the polymer layer is 15-25 microns thick in one embodiment. In another embodiment, the aluminum is 0.1-1 microns thick, and the polymer layer is 25-30 microns thick.

The laminates deployed herein make longer term storage of reagents easier because the holder includes both sealed lyophilized reagents and liquids sealed in close proximity, which is normally hard to achieve.

In one embodiment, the tops of the reagent tubes have beveled edges so that when an aluminum foil is heat bonded to the top, the plastic melt does not extend beyond the rim of the tube. This is advantageous because, if the plastic melt reduces the inner diameter of the tube, it will cause interference with the pipette tip during operation. In other embodiments, a raised flat portion 599 on holders 804 facilitates application and removal of laminate 598. Raised surface 599, on the upper side of the connecting member, and surrounding the inlet apertures to the reagent tubes and, optionally, the waste chamber, is an optional feature of the holder.

Figure 6:
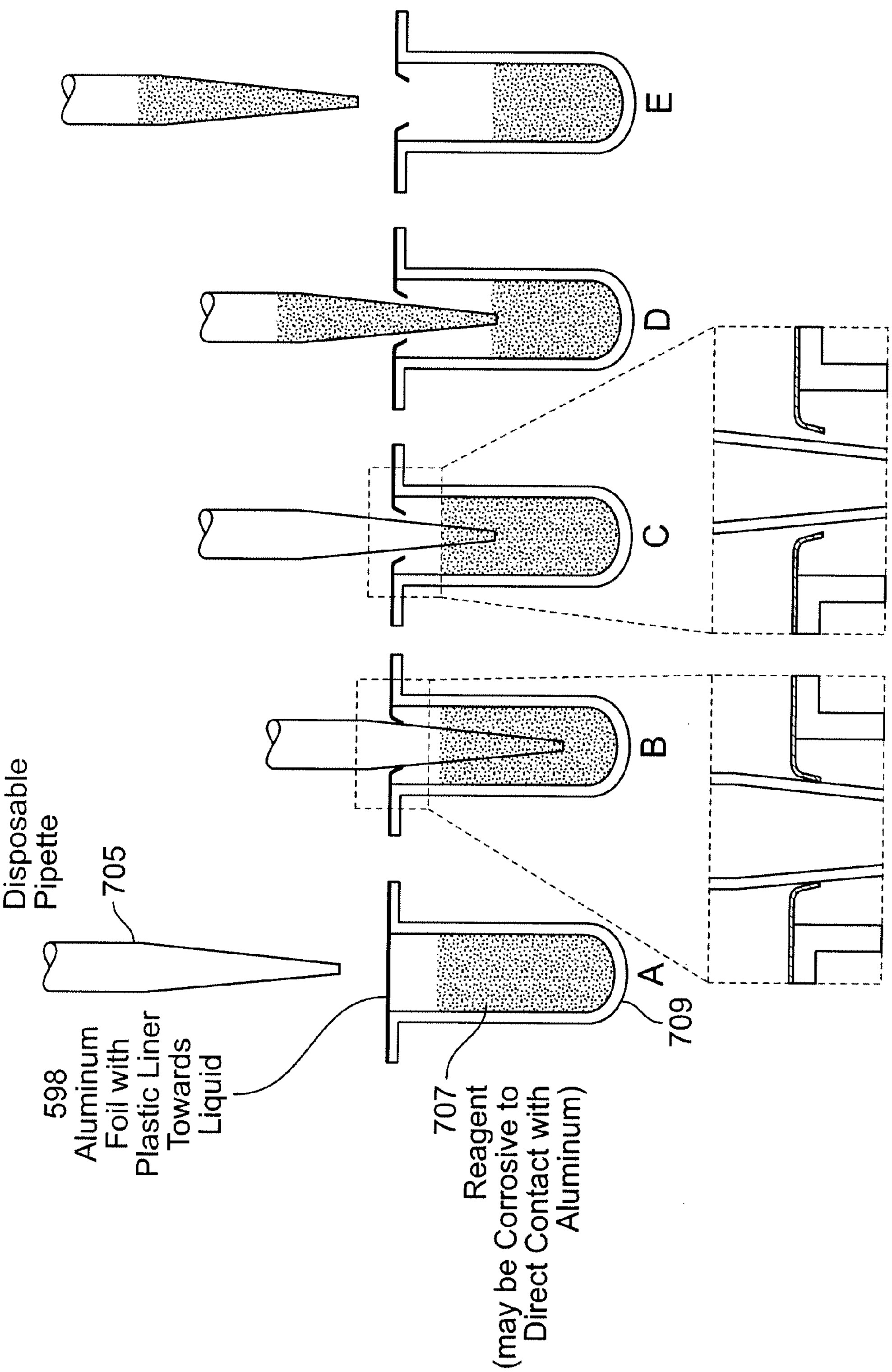
FIG. 6 shows a sequence of pipetting operations in conjunction with a laminated layer, as in FIG. 5.

The manner in which liquid is pipetted out is such that a pipette tip piercing through the foil rips through without creating a seal around the pipette tip, as illustrated in FIG. 6. Such a seal around the tip during pipetting would be disadvantageous because a certain amount of air flow is desirable for the pipetting operation. In this instance, a seal is not created because the laminate structure causes the pierced foil to stay in the position initially adopted when it is pierced. The upper five panels in FIG. 6 illustrate, in sequence, the pipetting of a reagent 707 (which may be corrosive to direct contact with Aluminum) out from a reagent tube 709 sealed with a laminate 598 as further described herein. At A, the pipette tip is positioned approximately centrally above the reagent tube that contains reagent 707. At B, the pipette tip 705 is lowered, usually controllably lowered, into the reagent tube, and in so doing pierces the laminate 598. The exploded view of this area shows the edge of the pierced laminate to be in contact with the pipette tip at the widest portion at which it penetrates the reagent tube. At C, the pipette tip is withdrawn slightly, maintaining the tip within the bulk of the reagent 707. The exploded view shows that the pierced foil has retained the configuration that it adopted when it was pierced and the pipette tip descended to its deepest position within the reagent tube. At D, the pipette tip sucks up reagent 707, possibly altering its height (without bottoming out) as more reagent is removed from the tube. At E, the pipette tip is removed entirely from the reagent tube.

The reagent holder of embodiments 804 has a connecting member 510 that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, process tube, sockets, reagent tubes, and waste chamber if present. For example, a holder may be made shorter, if some apertures are staggered with respect to one another and occupy 'off-axis' positions. The various receptacles, etc., also do not need to occupy positions with respect to one another that are the same as those shown in FIG. 3A, 3B, or 4. Thus, in FIGS. 3A and 3B, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath, and mounting the waste tube adjacent the process tube (see FIG. 4). It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein. Each such configuration of the reagent holder can be accommodated by a corresponding variation in form of the rack described herein that receives one or more such holders.

In some embodiments, the holder comprises a registration member such as a mechanical key. Typically such a key is part of the connecting member 510. A mechanical key ensures that the holder is accepted by a complementary member in, for example, a supporting rack as described herein or a receiving bay of an apparatus that controls pipetting operations on reagents in the holder. Thus, embodiment 501 has a mechanical key 592 that comprises a pair of rectangular-shaped cutouts on one end of the connecting member. This feature as shown additionally provides for a tab by which a user may gain a suitable purchase when inserting and removing the holder into a rack or another apparatus. Embodiment 501 also has a mechanical key 590 at the other end of connecting member 510. Key 590 is an angled cutout that eases insertion of the holder into a rack, as well as ensures a good registration therein when abutting a complementary angled cut out in a recessed area configured to receive the holder.

In some embodiments, not shown in FIG. 3A, 3B, or 4, the holder further comprises an identifier affixed to the connecting member. The identifier may be a label, such as a writable label, a bar-code, a 2-dimensional bar-code, or an RFID tag. The identifier can be, e.g., for the purpose of revealing quickly what combination of reagents is present in the holder and, thus, for what type of sample preparation protocol it is intended. The identifier may also indicate the batch from which the holder was made, for quality control or record-keeping purposes. The identifier may also permit a user to match a particular holder with a particular sample.

It should also be considered consistent with the description herein that a holder additionally can be configured to accept a sample, such as in a sample tube. Thus, in embodiments described elsewhere herein, a rack accepts a number of sample tubes and a number of corresponding holders in such a manner that the sample tubes and holders can be separately and independently loaded from one another. Nevertheless, in other embodiments, a holder can be configured to also accept a sample, for example in a sample tube. And thus, a complementary rack is configured to accept a number of holders, wherein each holder has a sample as well as reagents and other items. In such an embodiment, the holder is configured so that the sample in a suitably marked tube or container is accessible to a sample identification verifier.

A reagent holder for use with a rack as described herein is typically made of a plastic such as polypropylene. The plastic is such that it has some flexibility to facilitate placement into a rack, as further described herein. The plastic is typically sufficiently rigid, however, so that the holder will not significantly sag or flex under its own weight and will not easily deform during routine handling and transport or pipetting operations as further described herein, and thus will not permit reagents to leak out from it.

The holder is typically such that the connecting member, process tube, the two or more reagent tubes, and the waste chamber (if present) are made from a single piece, made from a material such as polypropylene.

The materials of the various tubes and chambers may be configured to have at least an interior surface smoothness and surface coating to reduce binding of DNA and other macromolecules thereto. Binding of DNA is unwanted because of the reduced sensitivity that is likely to result in subsequent detection and analysis of the DNA that is not trapped on the surface of the holder.

Rack

The apparatus outlined herein, and also described in U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), incorporated by reference herein, is configured to carry out various liquid transfer operations on samples and various reagents, in parallel. The samples and various reagents are typically held in one or more removable racks 970, positioned in the apparatus (such as one shown in FIG. 1, 2A, or 2B), while the various liquid transfer operations are carried out. Optionally, the operations can be carried out on the reagents, stored in holders located directly in the apparatus, without use of a removable rack.

The racks for use herein are typically configured to be insertable into, and removable from, a diagnostic or preparatory apparatus as further described herein (e.g., in connection with FIGS. 1, 2A and 2B), each of the racks being further configured to receive a plurality of reagent holders, and to receive a plurality of sample tubes, wherein the reagent holders are in one-to-one correspondence with the sample tubes, and wherein the reagent holders each contain sufficient reagents to extract polynucleotides from a sample and to place the polynucleotides into a PCR-ready form. Exemplary racks are further described in U.S. patent application Ser. No. 12/178,584, filed Jul. 23, 2008, to Duffy et al., incorporated herein by reference in its entirety.

Figure 7:
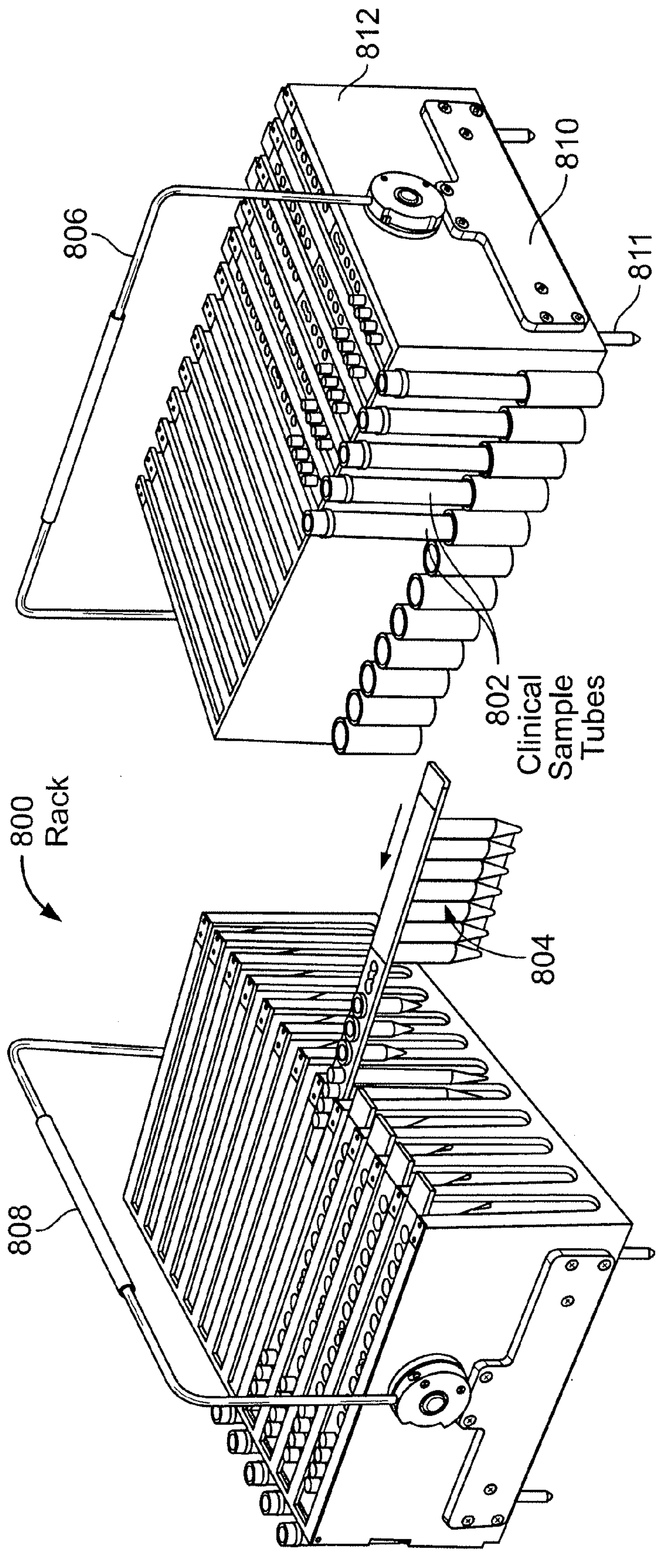
FIG. 7 shows perspective views of an exemplary rack for samples and reagent holders.
Figure 8:
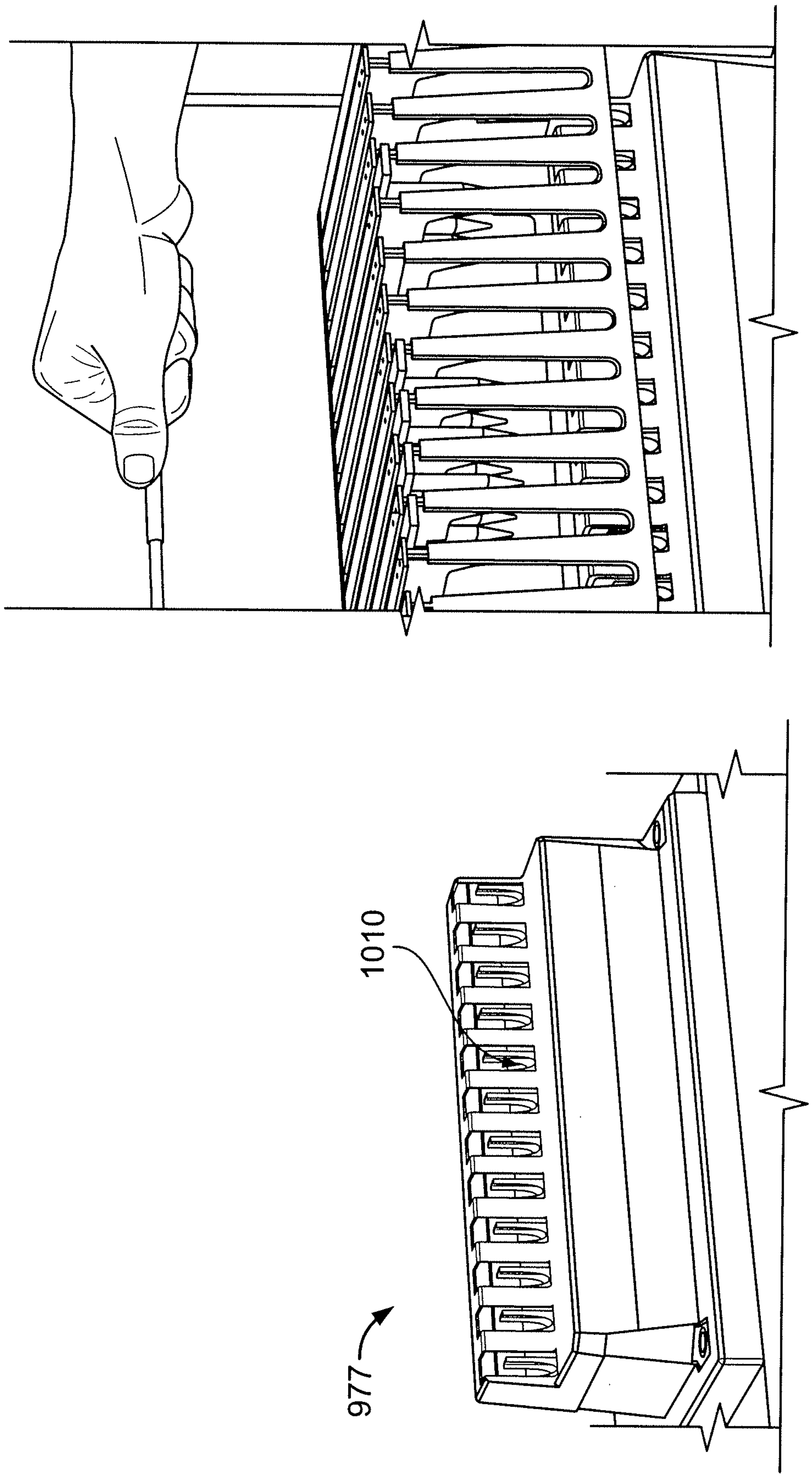
FIG. 8 shows perspective views of the rack of reagent holders and sample tubes of FIG. 7, in conjunction with a heater unit.

Two perspective views of an exemplary rack 800, configured to accept 12 sample tubes and 12 corresponding reagent holders, in 12 lanes, are shown in FIG. 7. A lane, as used herein in the context of a rack, is a dedicated region of the rack designed to receive a sample tube and corresponding reagent holder. A perspective view of the same exemplary rack, in conjunction with a heater unit, as further described herein, is shown in FIG. 8. The lanes of the rack described herein are designed to have sufficient depth and width to accommodate the various reagent tubes, receptacles, process tube, and pipette sheath of a given reagent holder as described elsewhere herein, and to position the process tube in communication with a heater/separator unit.

A rack may accept 2, 4, 6, 8, 10, 12, 16, or 20 samples such as in sample tubes 802, and a corresponding number of reagent holders 804. Thus the embodiment of FIG. 8, configured to receive 12 samples in sample tubes 802, and 12 corresponding reagent holders 804, is exemplary.

Rack 800 is shown with a handle 806, having optionally a hand-grip 808, to facilitate transport, and removal from the apparatus. Rack 800 is also shown with positioning feet 811 that can help stabilize the rack during loading and when resting on, e.g., a bench-top, outside of the apparatus. Rack 800 is also shown as having a structural member 810, typically made of steel, that provides strength and rigidity for the rack, and also ensures that the rack fits tightly into an appropriately configured receiving area of the apparatus. Rack 800 is also shown as having a body 812 configured with a number of slots that accept the reagent holders.

As described elsewhere herein, the holders each comprise a process tube in which reactions, e.g., between reagents and sample, take place, typically with some heating, or cyclical heating and cooling. The location of the reagent holders in the rack typically ensures that the process tubes are effectively located in proximity to the heater units, as shown in FIG. 8.

Heater Assembly & Magnetic Separator

The racks as described herein are configured such that the reagent holders placed in the racks are positioned so that the process tubes in the holders are heated by a dedicated heating assembly 977, as may be situated in an apparatus for carrying out sample preparation and analysis on multiple samples in parallel, such as shown in FIG. 1, 2A or 2B. Typically such a heater assembly comprises one or more independently controllable heater units 1010, each of which comprises a heat block configured to heat a process tube in a reagent holder situated in the rack, as further described herein. In one embodiment, a heat element is a power resistor. The right hand panel of FIG. 8 shows how holders loaded in a rack can be positioned in close proximity to such a dedicated heating unit. The heating unit is configured to heat the process tube in each of one or more reagent holders positioned in the rack, without unduly heating other portions of the rack, or other containers associated with the reagent holders.

Yet additionally, the holders herein are configured so that each process tube is in close enough proximity to a magnetic assembly that separation of magnetic particles from reagents in solution in the process tubes can be accomplished. An exemplary magnetic separator is configured to move one or more magnets relative to the one or more process tubes. Typically, the magnet is mounted in such a way that it can be moved in proximity to the process tubes, either in an automated fashion such as under control of a processor, or manually. The magnet can be made of neodymium (e.g., from K & J Magnetics, Inc.) and can have a magnetic strength of 5,000-15,000 Gauss (Brmax). The poles of the magnets can be arranged such that one pole faces the heat blocks and the other faces away from the heat blocks.

Advantageously, the heater assembly and magnetic separator operate together to permit successive heating and separation operations to be performed on liquid materials in the one or more process tubes without transporting either the liquid materials or the process tubes to different locations to perform either heating or separation. An exemplary heater assembly and magnetic separator are further described in U.S. provisional Patent Application Ser. No. 60/959,437, filed Jul. 13, 2008, and U.S. patent application Ser. No. 12/173,023, filed Jul. 14, 2008, entitled "Integrated Apparatus for Performing Nucleic Acid Extraction and Diagnostic Testing on Multiple Biological Samples", in the name of Williams, et al., and Ser. No. 12/178,586, entitled "Integrated Heater and Magnetic Separator", in the name of Handique, filed on Jul. 23, 2008, all of which are incorporated herein by reference in their entirety.

The heater assembly and magnetic separator are also configured to operate in conjunction with the liquid dispenser further described herein so that, when appropriate quantities of liquid reagents and/or sample have been dispensed into the process tube adjacent the heater and separator, the heater and separator are controllably activated to accomplish the required heating and/or separating.

Pipetting Operations

Figure 9:
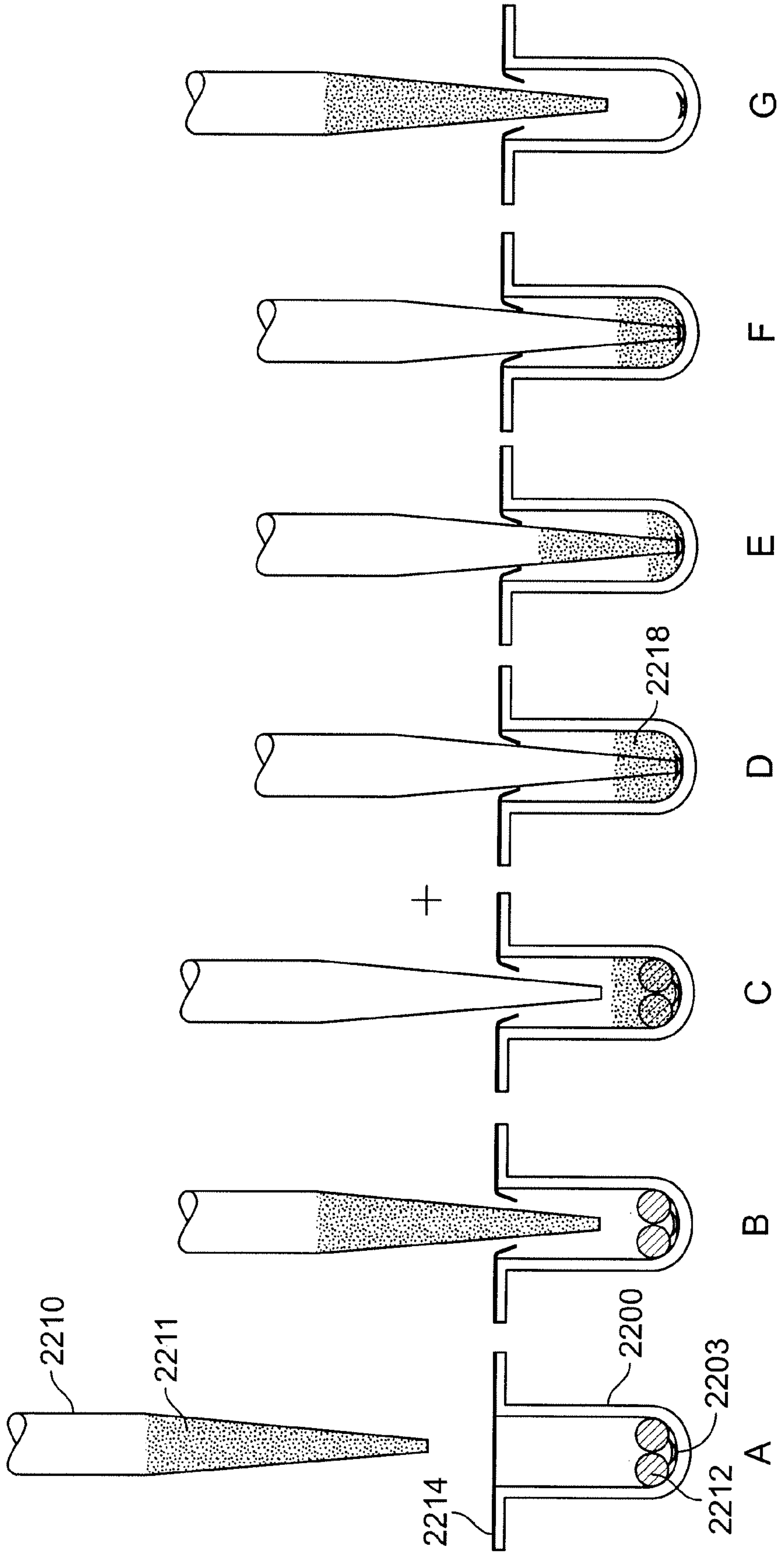
FIG. 9 shows a sequence of pipetting operations in conjunction with a reagent tube.

Basic pipetting operations, such as may be accomplished with the automated pipetting apparatus described herein, are now described, as follows. FIG. 9 has a number of panels, A-G, each representing, in sequence, a stage in an exemplary pipetting operation, such as may be carried out with a pipette head as described further herein and a process tube, as described elsewhere herein. At A, a pipette tip 2210, containing a liquid 2211 (such as a buffer solution), is positioned directly or approximately above the center of reagent tube 2200. The tube contains a number of lyophilized pellets 2212, and is sealed by a layer 2214, such as of foil. The foil may be heat-sealed on to the top of the tube. Although a laminate layer, as further described herein, can be placed on the reagent tube, typically a layer of aluminum foil is adequate, where the tube contents are solid, e.g., lyophilized, reagents. In some embodiments, the top of the reagent tube has chamfer edges to reduce expansion of the top rim of the tube during heat sealing of a foil on the top of the tube.

In various embodiments, preparation of a PCR-ready sample for use in subsequent diagnosis using the apparatus as further described herein, can include one or more of the following steps: contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid); in some embodiments, the PCR reagent mixture can be in the form of one or more lyophilized pellets, as stored in a receptacle on a holder, and the method can further include reconstituting the PCR pellet with liquid to create a PCR reagent mixture solution. Various, such as one or more, of the liquid transfer operations associated with the foregoing steps can be accomplished by one or more pipette heads on an automated pipetting apparatus that comprises a liquid dispenser, as further described herein.

Figure 10:
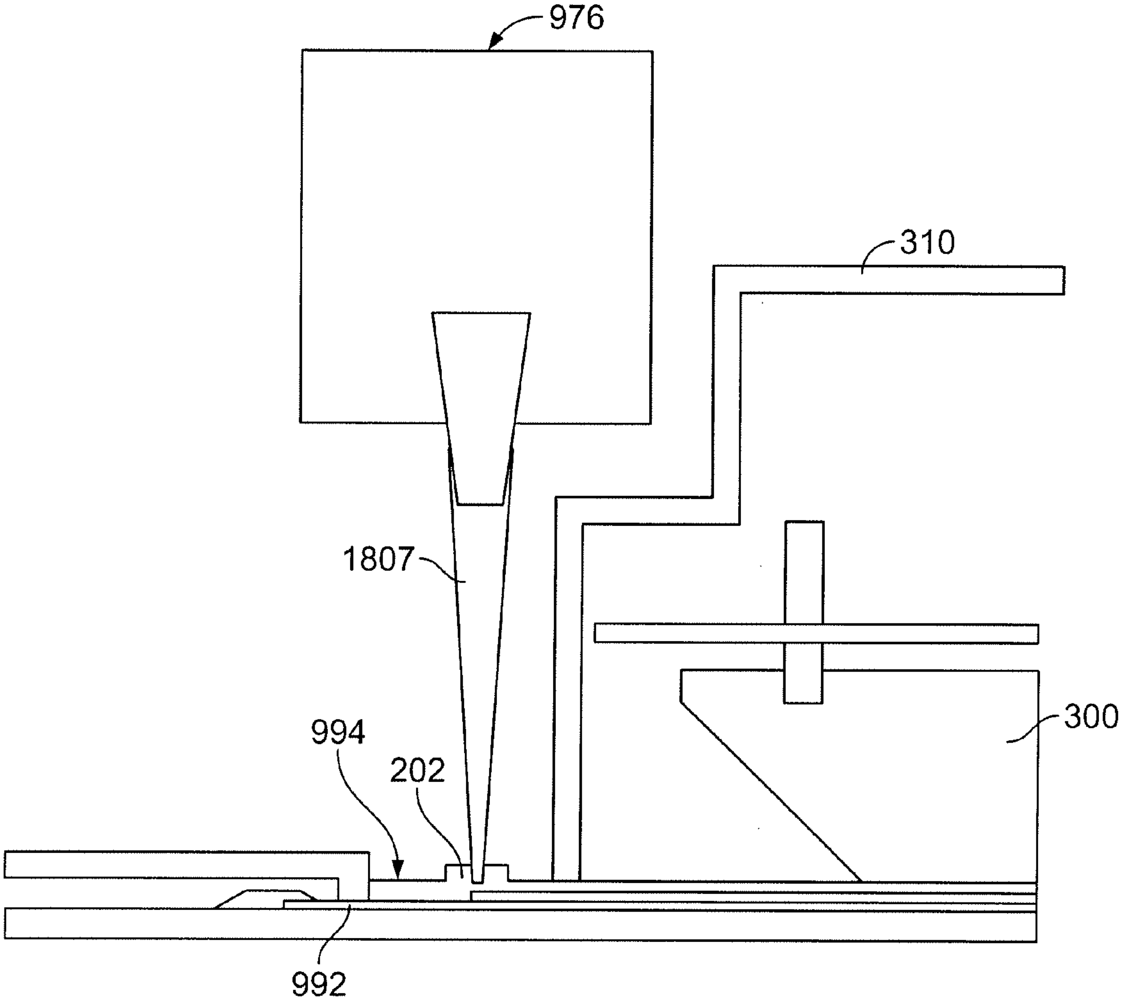
FIG. 10 shows a side schematic view of a pipette head in position to dispense liquid into a microfluidic cartridge.

The automated liquid dispenser can be further configured to dispense a solution (e.g., of a prepared sample, various PCR reagents, and detection tags) into a microfluidic cartridge. Thus, the liquid dispenser is configured to travel from a first set of positions above reagent holders having various containers that hold reagents, etc., to a second set of positions above the inlets of a microfluidic cartridge. The second set of positions is depicted schematically in FIG. 10, in side cross-sectional view. The travel of the liquid dispenser between the first set of positions and the second set of positions can be accomplished by motions in combinations of two orthogonal directions in a horizontal plane, for example, along supporting structures as further described herein, and under control of a microprocessor. Although not apparent from FIG. 10, it is consistent with the depiction that multiple, e.g., 4, pipette tips are dispensing fluid into different inlets of microfluidic cartridge 994 at any time. Liquid dispenser 976 has attached a pipette tip 1807 that is positioned so that its tip is inserted into an inlet 202 of a microfluidic cartridge 994. The cartridge is situated in a receiving bay 992. An optional cover 310 is configured to shut out ambient light from the remainder of cartridge 994, where, e.g., a target polynucleotide is detected after PCR, so that detector 300 can be as effective as possible. Suitable detectors are described in, e.g., U.S. patent application Ser. No. 12/218,498, filed Jul. 14, 2008, and incorporated herein by reference in its entirety. Although it is to be understood that the liquid dispenser herein is typically configured for use with a microfluidic cartridge, it can equally be configured to deliver appropriate quantities of prepared polynucleotide in solution to other locations at which such polynucleotides can be amplified and detected.

Liquid Dispenser

The liquid dispenser, as further described herein, can be configured to carry out pipetting operations in parallel on samples and solutions stored in one or more holders, and in one or more sample tubes, in a rack, as described elsewhere herein. It would be understood, however, that the operation, design, and function of the liquid dispenser is not dependent upon the locations of the samples and various solutions, but that the liquid dispenser could perform similarly in connection with pipetting solutions disposed in other types of receptacles. Thus, a liquid dispenser, as described herein, is an assembly of components that together cooperate to carry out such pipetting operations on solutions. The liquid dispenser thus, typically, can pick up and drop off pipette tips as needed, as well as aspirate quantities of liquid up into, and deposit out those quantities of liquid from, such pipette tips. The motions and operation of the liquid dispenser is typically controlled by a processor such that pipetting operations can be automated.

Advantageously, the liquid dispenser can be configured so that the pumps, sensors (e.g., for pipette tip presence detection, and force sensing during pipetting), sample identification verifier, and other items, move with it, and therefore minimize the number of control lines that move across the instrument during use, and also reduces the likelihood that such control lines will become tangled during motion of the liquid dispenser, as would be the case where pipette dispense heads are the only items undergoing motion, and remain in communication with other components that are fixed at various points within a preparatory or diagnostic apparatus. In such apparatus, where only e.g., dispense heads undergo motion, the need to be able to move freely in three degrees of freedom becomes severely constrained by the need to move a number of cables independently of one another.

Advantageously, as further described herein, also, the dispenser can be configured to align pipette tips, e.g., with cartridge inlet holes, using a motorized alignment plate. Additionally, as also described elsewhere herein, the dispenser can be configured with a scanner that reads information from, e.g., a sample.

Figure 11:
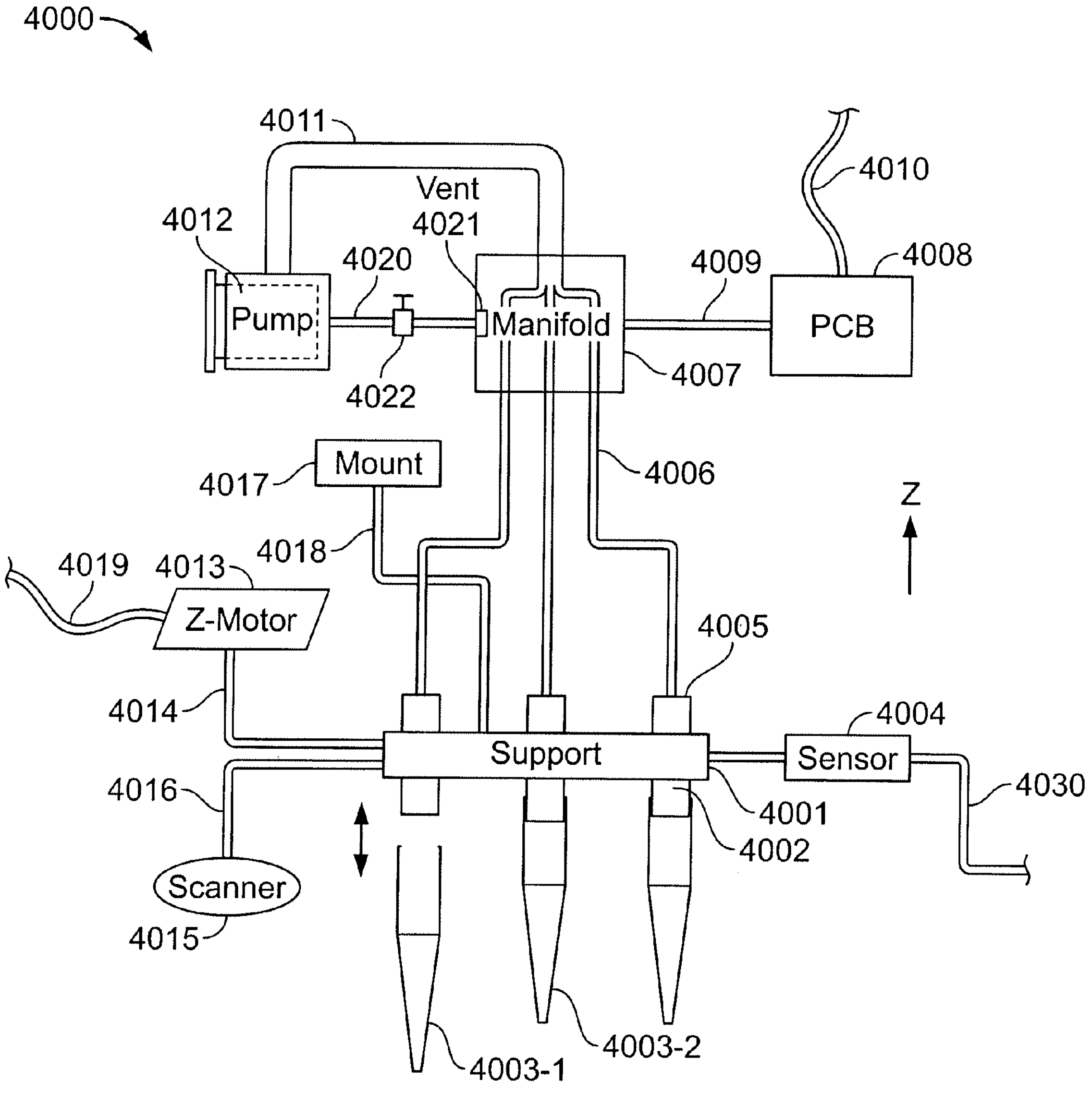
FIG. 11 shows a block diagram of a liquid dispenser, showing communication between various components thereof.

FIG. 11 shows, schematically, components of a liquid dispenser 4000 as further described herein. The layout of the components in FIG. 11 is for convenience only, and one of skill in the art would appreciate that other arrangements are possible, depending upon environment and other factors. A support 4001 has three dispense heads 4002 mounted to it. Other numbers of dispense heads, such as 1, 2, 4, 5, 6, 8, and 10, are consistent therewith. The dispense heads are configured to accept pipette tips 4003-1 (shown detached from its head), and 4003-2, shown mounted on the head. The support 4001 is movably attached via a connecting member to a mount 4017. The relative position of the support and the mount, in the z-direction as shown, can be controlled by Z-motor 4013, which is electrically coupled via connection 4014 to the support 4001. Z-motor receives instructions from a processor (not shown) via a connection 4019. In the embodiment shown, Z-motor is able to control the relative position of support 4001 and mount 4017 by moving support 4001. In other embodiments, Z-motor 4013 is coupled to mount 4017 and achieves similar relative motion of mount and support. Such relative motion can be accomplished by any suitable mechanical movement device, such as gearing, or a rack and pinion assembly, or a lead screw, the details of which are not shown in FIG. 11.

Also included within the liquid dispenser 4000 is a sensor 4004 configured to sense when vertical motion of the support or mount is obstructed, and to provide a suitable signal, e.g., via an electrical connection 4020, directly to a processor (not shown), or indirectly (not shown) via printed circuit board 4008. Thus sensor 4004 can be mounted on support 4001, as shown, or on mount 4017, depending on matters of design choice.

Optionally included within the liquid dispenser 4000 is a scanner 4015, connected to, e.g., support 4001 (or, alternatively, to mount 4017) via a connector, such as a mechanical attachment, 4016. Scanner 4015 can be configured to read, e.g., sample and patient information, from one or more of a sample tube, reagent holder, or microfluidic cartridge, as further described elsewhere herein. Scanner 4015 can be electrically connected directly (not shown) to a processor, or indirectly via printed circuit board 4008.

A valve 4005 is associated with each dispense head 4002, and serve to control operation of each dispense head such as by, for example, controlling when to reduce pressure, thereby causing a sucking operation, or to increase pressure, thereby causing a dispense operation. Each valve 4005 is connected to (including being in fluid communication with) manifold 4007 via a connecting tube 4006.

Manifold 4007 is connected to pump 4012 via an air-line 4011, and to valves 4005 via connecting tubes 4006. Manifold 4007 contains a number of independently controllable valves that selectably divert air from pump 4012 to various of valves 4005, and therefore to corresponding dispense heads 4002. In FIG. 11, a way to accomplish this is shown schematically: line 4011 is split into three separate lines each of which connects to one of lines 4006. In embodiments that service different numbers of dispense heads, such as 4 heads, line 4011 is similarly split into 4 corresponding lines.

Manifold 4007 is also typically connected to pump 4012 via a second line 4020 that is configured to permit equilibriation of air between manifold and pump. Line 4020 connects to a vent 4021 on the manifold, and is also controlled by a valve 4022.

Operation of manifold 4007 is typically controlled by printed circuit board (PCB) 4008 to which it is connected via an electrical connection 4009. PCB 4008 additionally can receive electrical input from connection 4010. Thus, the suck and dispense operations can be precisely controlled, by signals from the PCB, so that accurate volumetric control is achieved. In some embodiments, calibration of the liquid dispenser is required so that the amount of time to force or to suck air that is required to dispense or aspirate a desired volume of liquid is known. Thus, the time between, e.g., a valve opening and valve closing, as controlled by signals, is known and can be incorporated into the control software.

Pump 4012 typically also comprises a motor (not shown) controlling its action, e.g., motion of a plunger, which receives electrical signals as input, and an air supply (not shown).

FIGS. 12-21 (inclusive) show various views of an exemplary liquid dispenser, now various components of which are further described herein. It would be understood by one of ordinary skill in the art that such components, their relative configuration, number, and orientation, are exemplary, and that the degrees of freedom of motion, and accuracy of positioning and dispensing, consistent with the description herein may be achieved by other such configurations. For example, where one or more mounts are shown, other embodiments may have different numbers of mounts.

Figure 12:
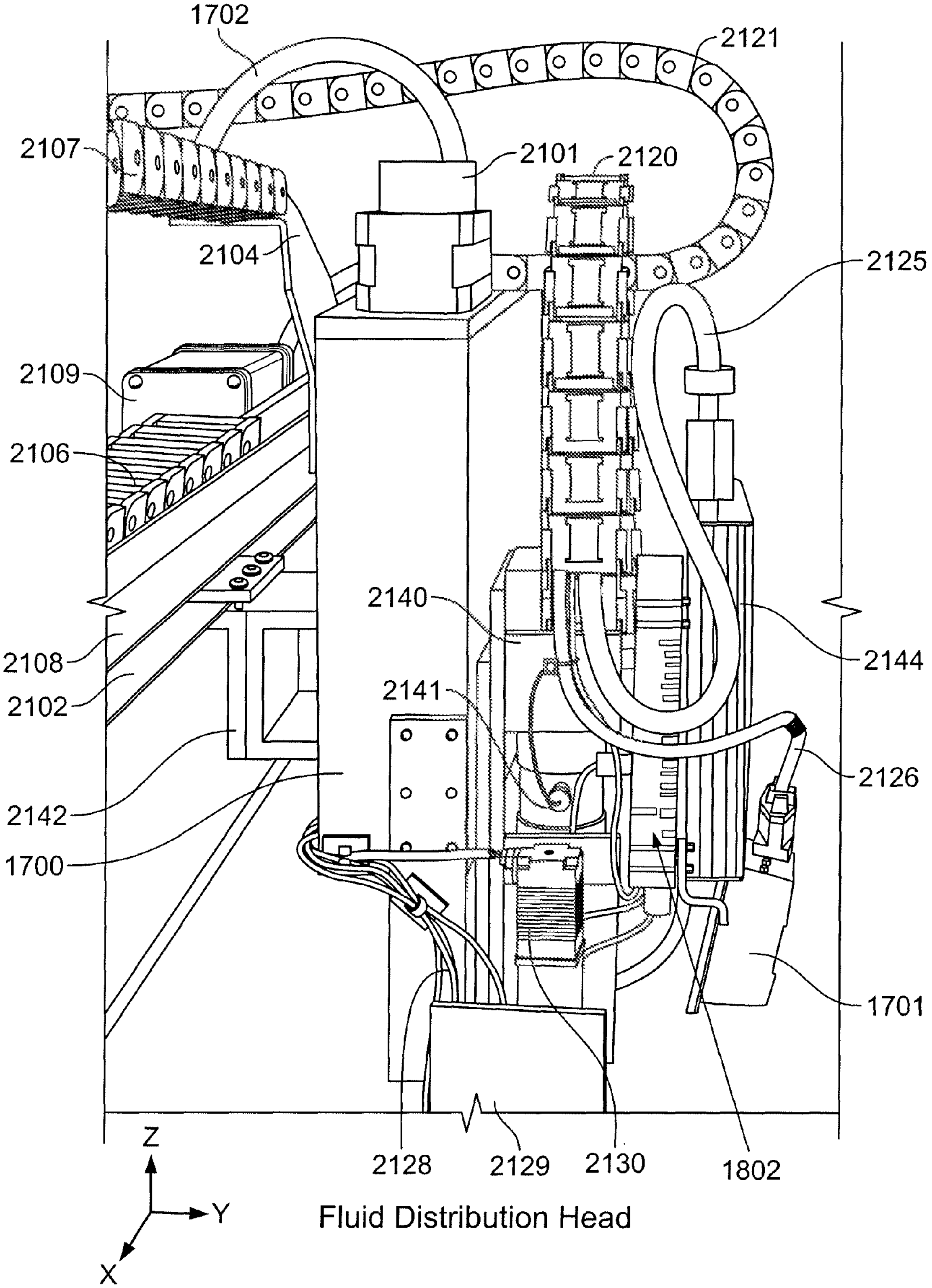
FIG. 12 shows a liquid dispense head.

A perspective side view of an exemplary liquid dispense head is shown in FIG. 12. The following items relate to control of movement of the liquid dispenser, and the housing of the liquid dispenser, are visible. Control belts 2120 and 2121 house electrical cables, are disposed orthogonally to one another, and permit motion of the liquid dispenser in two orthogonal directions: in a horizontal and a vertical plane. Control belts 2106 and 2107 hold further electrical cables, and are disposed to permit motion in a horizontal plane, orthogonal to belt 2121. Belts 2106, 2107, 2120, and 2121 permit easy motion of the liquid dispenser without entangling various electrical cables because the belts guide and house the cables while the dispenser is in motion. Electrical cable 2125 supplies control signals to assembly 2144, which houses electrical circuitry to control operation of manifold 1802 and a pump 2141 of the liquid dispenser. Manifold 1802, attached to pipette heads and other items as described herein, is thereby capable of moving up and down (z-axis), as well as in two horizontal directions. Electrical cable 1702 supplies control signals to assembly 2101, which is coupled to a motor for accomplishing vertical motion, and thereby permits such motion to be controlled. Assembly 1700 is a housing that holds the motor and the sliding head and is attached to one or more mounting plates 2104, 2142, which at least one of which is attached to a gantry 2108. A mounting assembly 2140 connects the liquid dispenser to the assembly 1700 that controls vertical motion. Mounting assembly 2140 can further comprise an air displacement/plunger pump for directing air to the dispense head. A further mounting 2129 serves as a shield for the pipette dispense heads.

The gantry 2108 comprises a horizontal rail 2102 to provide movement in the x-direction, controlled by controller 2109, which receives electrical input from cables (not shown). Also not shown is an orthogonally disposed rail to provide movement in the y-direction of the rail and the attached assemblies. The gantry permits, overall, three degrees of translational freedom of the liquid dispenser. (Further embodiments, not herein described, can comprise a gantry having fewer than three degrees of translational freedom.) A suitable gantry comprises three axes of belt-driven slides actuated by encoded stepper motors. The gantry slides can be mounted on a framework of structural angle aluminum or other equivalent material, particularly a metal or metal alloy. Slides aligned in x- and y-directions (directed out of and in the plane of FIG. 12 respectively) facilitate motion of the dispenser across an array of holders, and in a direction along a given holder, respectively. The z-axis of the gantry can be associated with a variable force sensor which can be configured to control the extent of vertical motion of the head during tip pick-up and fluid dispensing operations, as further described herein.

Figure 13B:
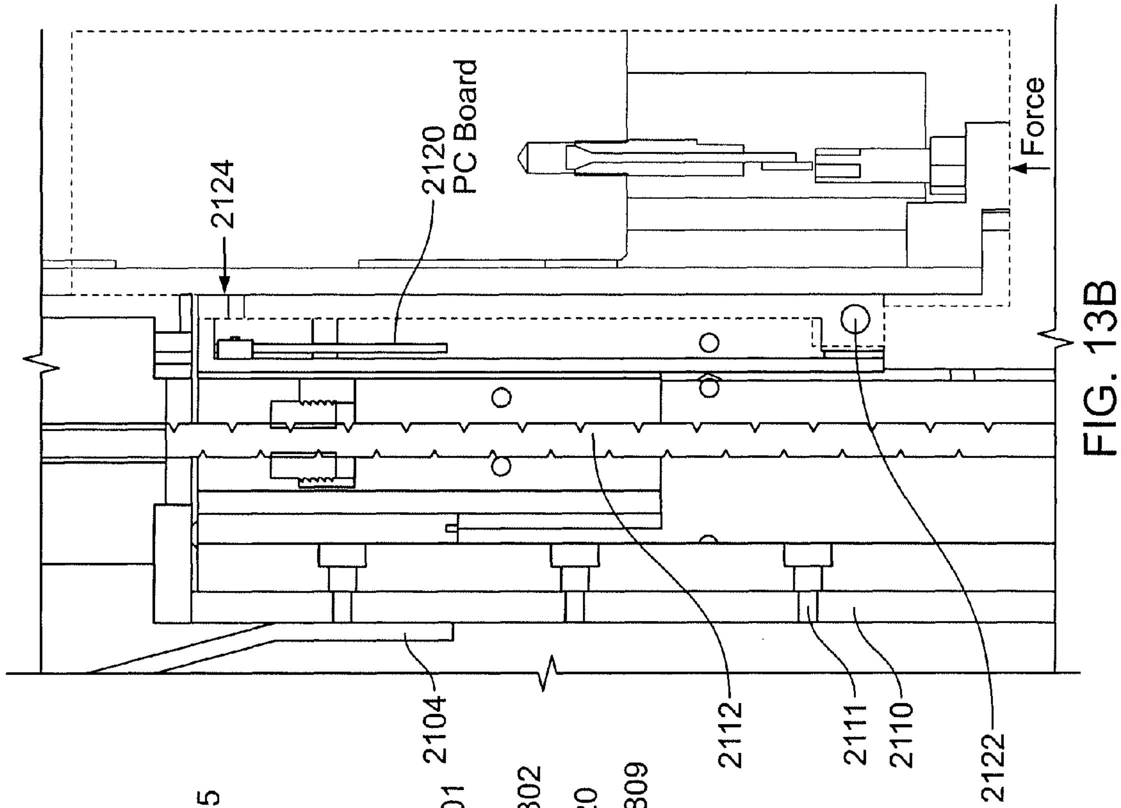
FIGS. 13A and 13B show views of a liquid dispenser.
Figure 13A:
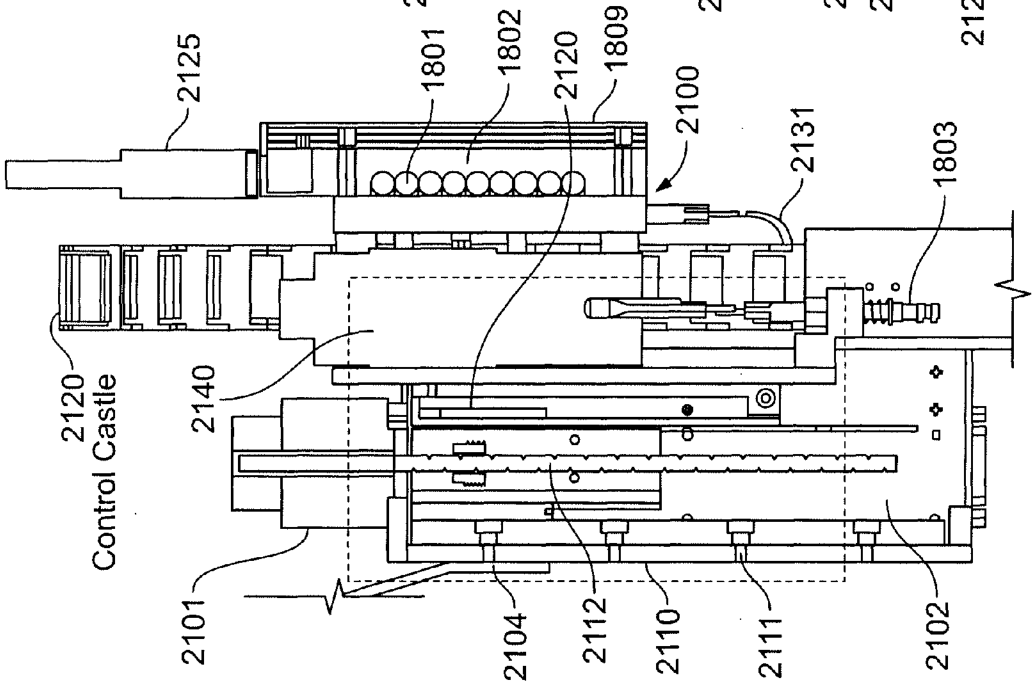

Assembly 1700 is shown only as an outer housing; internal parts are further shown in FIGS. 13A and 13B. A manifold 1802 is attached to an assembly 2140; the manifold controls suck and dispense operations performed by multiple pipette heads (not shown in FIG. 12). Assembly 2140 can undergo vertical movement, under suitable control, and is also further illustrated in FIGS. 13A and 13B. A detector 1701 is mounted indirectly to assembly 2140 and therefore can also move in a vertical direction. Detector 1701 typically permits positive detection of sample tubes, reagent disposables, and microfluidic cartridges. Electrical cable 2126 provides control signals to detector such as a scanner, or read-head 1701. A motor 2130 is a positioned to control motion of a stripper plate for stripping pipette tips, as further described herein. Electrical control of stripper motor 2130 can be provided by various electrical cables such as 2128 as shown in FIG. 12.

As shown in the various figures, the entire liquid dispenser that moves up and down the z-axis is a self-contained unit having only electrical connections to a processor or controller, and mechanical connections to the gantry. The translational motions in three dimensions of the liquid dispenser can be controlled by a microprocessor, such as processor 980. No fluid handling lines are associated with the dispenser. This design enables simplification of assembly of the instrument, minimizes contamination of the instrument and cross-contamination of samples between different instances of operation of the apparatus, increases efficiency of pumping (minimal dead volume) and enables easy maintenance and repair of the device. This arrangement also enables easy upgrading of features in the dispensing device, such as individual and independent pump control for each dispenser, individual pipette attachment or removal, ability to control the pitch of the pipettes, etc.

A suitable liquid dispenser for use with the apparatus herein comprises: one or more sensors (such as for sensing pipette tips, in FIGS. 17A-17C, and as further described herein); a manifold 1802; one or more pumps 2141 in fluid communication with the manifold; one or more dispense heads 1803 in fluid communication with the manifold; and electrical connections that accept electrical signals from an external controller, wherein the liquid dispenser has no inlet or outlet for fluids, other than through the one or more pumps. As described elsewhere herein, the liquid dispenser can be configured to carry out fluid transfer operations on two or more holders simultaneously, such as when operating under instructions received from one or more electrical controllers. Other sensors incorporated into the apparatus include: a sensor to sense when a pipette tip reaches the bottom of a sample tube (also called an encoder/stall sensor, as further described herein); and sensors that restrict motion of the stripper plate so that it moves back and forth between two limit switches.

A cross-sectional view of the exemplary liquid dispenser of FIG. 12 is shown in FIGS. 13A and 13B. FIG. 13B shows in close-up a portion (dashed-line box) of FIG. 13A. (Various items visible in FIG. 12, such as control cables, are omitted from FIGS. 13A and 13B, for clarity.) Liquid dispenser 2100, and ancillary items shown in FIGS. 13A and 13B, are mounted on a gantry (not shown) via a support 2104. The manner of mounting can be by a supporting member 2110, such as a plate, to which the dispenser is attached via a mechanical fastening such as one or more screws 2111. In the embodiment of FIG. 13A, a lead screw 2112 (shown in cross-section) couples the z-motor with the whole z-head and provides a mechanism that permits the z-head to move up and down vertically.

Typically, pipette heads 1803 are individually sprung. Shown in FIGS. 13A, 13B, for example, a pipette head 1803 can be mounted such that a force acting upwardly against the head, such as created when a pipette tip attached to the head meets the bottom of a container from which liquid is being sucked, can be sensed through a relative motion between the head and a force sensor. For example, when a tip attached to pipette head 1803 forces against a disposable holder in a rack below it, an upward force is transmitted causing head 1803 to torque around pivot point 2122, causing set screw 2124 to press against a force sensor. In turn, the force sensor is in communication with a processor or controller on PC board 2120 that controls at least the vertical motion of the liquid dispenser so that, thereby, the processor or controller can send instructions to arrest the vertical motion of the liquid dispenser upon receiving an appropriate signal from the force sensor. An exemplary force sensor suitable for use herein is available from Honeywell. The force sensor mechanism shown in FIGS. 13A and 13B is exemplary and one of many possible mechanisms capable of commanding the head during up pick-up and fluid dispensing operations. For example, as an alternative to a force sensor, a stall sensor that senses interruption in vertical motion of the one or more dispense heads upon contact with a sample tube or reagent holder may be used. In some embodiments, the stall sensing is performed by the encoder of the z-motor. The encoder is a sensor attached to the motor and it senses any angular steps performed by the motor. During stalling of the z-head, the encoder senses that the motor has stopped moving even though the motor was instructed to go beyond the position at which it stalled. Accordingly, as would be understood by one of ordinary skill in the art, the upward motion of the liquid dispenser as described herein is not limited to the specific mechanism shown in FIGS. 13A and 13B. A length of tubing 2131 is attached between the fluidic manifold 1802 and each of the pipette attachment nozzles.

Figure 14B:
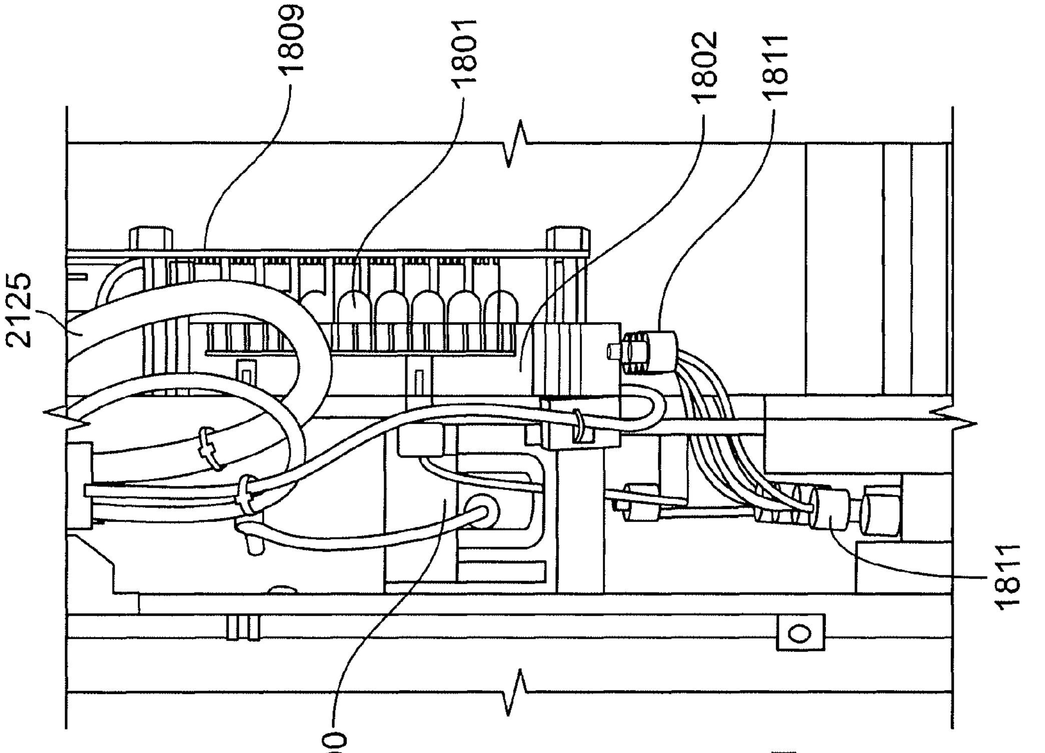
FIGS. 14A-14C show views of a liquid dispense head.
Figure 14A:
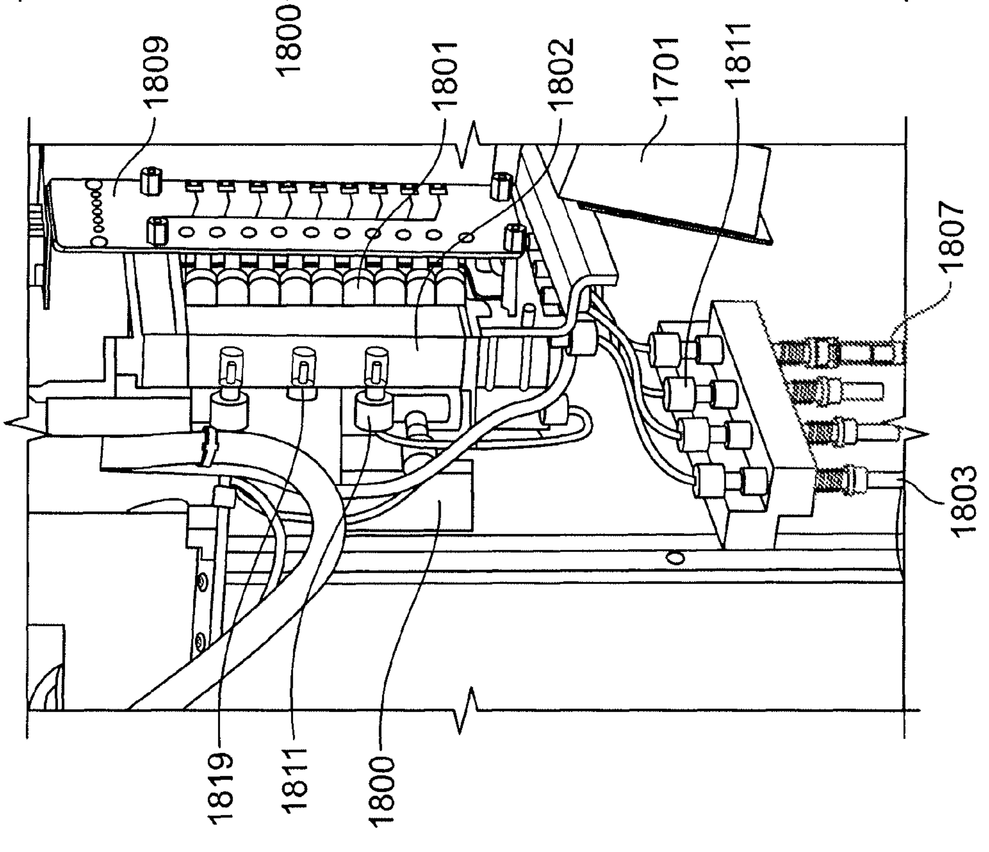
Figure 15:
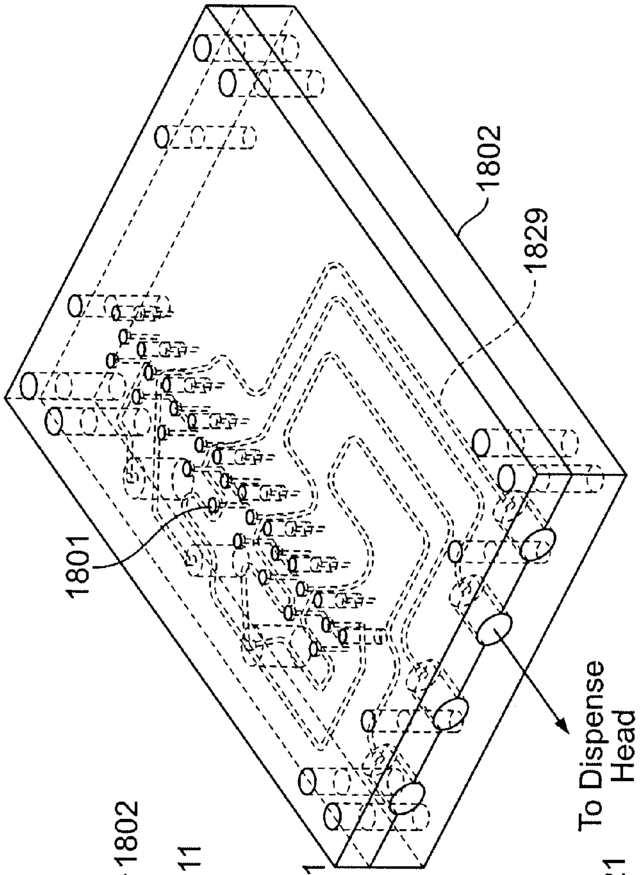
FIG. 15 shows an exemplary distribution manifold.
Figure 14C:
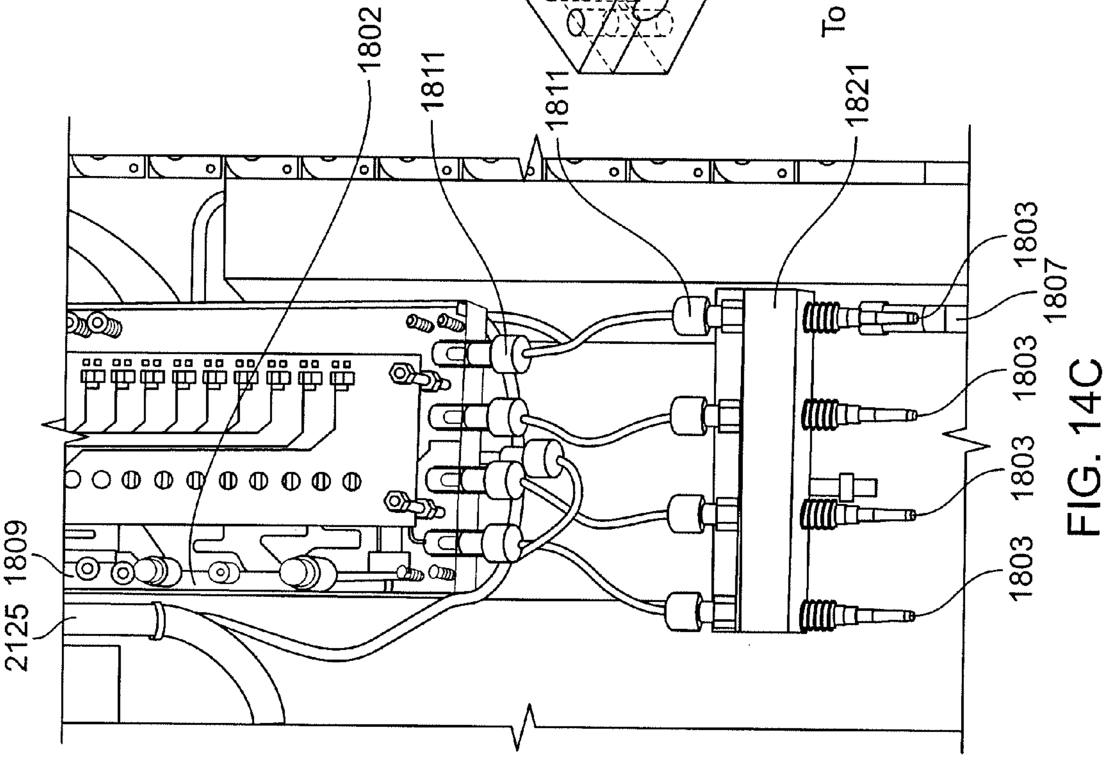

FIGS. 14A-14C show an exemplary liquid dispenser in close-up, in perspective (FIG. 14A), side (FIG. 14B, enlarged to show a portion of what is visible in the view of FIG. 14A), and front (FIG. 14C) views. The liquid dispenser comprises a number of individually sprung heads 1803, wherein each head is configured to accept a pipette tip, such as from the one or more pipette tips in a holder as elsewhere described herein. Thus the spacing of the heads is calculated to be the same as the spacing of the holders in a rack, as further described herein. The rightmost head is shown with a pipette tip 1807 attached to it, visible in FIGS. 14A and 14C. The liquid dispenser can be further configured such that no two heads accept pipette tips from the same holder. The liquid dispenser can be used with, or be adapted to be used with pipette tips that have volumes as small as 10 μl to as large as 1 ml.

FIGS. 14A-C depict, for example, a "4-up" automated pipetting apparatus having four individually sprung heads 1803, but it is to be understood that the dispenser is not limited to this number. For example, other numbers include 2, 3, 5, 6, 8, 10, or 12. Furthermore, the individually sprung heads 1803 are shown arranged in a line in FIG. 14A, but may be configured in other arrangements, such as an array, or a circle.

The liquid dispenser can further comprise computer-controlled, motorized, pump 1800 connected to distribution manifold 1802 with related computer-controlled valving. The distribution manifold typically travels with the dispense head, rather than being positioned at a fixed location away from the dispense head while the dispense head moves from one pipetting location to another. Computer-control can be accomplished via a control board 1809, shown in the embodiment of FIGS. 14A-14C mounted on the front of the liquid dispenser. It would be understood that, in other embodiments, the control board could be mounted elsewhere, including at locations other than on the liquid dispenser if it is desired to run electric cables to the dispenser.

Also shown in FIGS. 14A-14C are a number of connectors 1811 for tubing that extends from the pump to the fluidic manifold. A mechanical structure 1821 maintains the four pipette nozzles at a fixed distance and location relative to the z-head.

The liquid dispenser is typically configured to aspirate or dispense fluid in connection with analysis or preparation of solutions of two or more samples. However, that is not to say that any of the features described herein could not also be applied in a device that operates on a single sample. The liquid dispenser is also configured to dispense liquid into a microfluidic cartridge. Typically, the liquid dispenser is configured to accept or dispense, in a single operation, an amount of 1.0 ml of fluid or less, such as an amount of fluid in the range 10 nl-1 ml.

The liquid dispenser is configured such that pump 1800 pumps air in and out of the distribution manifold. The pump can have an air supply and can be as simple in construction as having a plunger that moves back and forward compresses/expands air volume, under control of a motor, whose operation is in turn controlled by electrical signals from a processor. Air can be supplied to pump 1800 and is typically under pressure, such as at 0.1-10 psi. Thus the air supply may ultimately be provided by a compressed air cylinder, located outside of the apparatus. Typically the pump communicates with the manifold via two airways. A first airway, directs pressurized air from the pump to the manifold. A second airway can be for the purpose of equilibriating, where required, between various pipette operations, and connects with a vent on the manifold. When the pump draws air in, it is typical to close off the vents and valves in the manifold.

Further shown in FIG. 14A is a vent 1819, usually equipped with a filter (so that any airborne particles are trapped). Vent 1819 is usually closed unless it is necessary to prime the pump (such as when equilibriating the airways).

Fluid distribution manifold 1802, of which an exemplary embodiment is shown in FIG. 13, can comprise a number of valves, such as solenoid valves 1801, as are available from, e.g., the Lee Co., configured to control the flow of air through the pipette tips. Construction and design of such a manifold is within the capability of one skilled in the art. In an exemplary embodiment, there are two valves for each pipette, and one additional valve to vent the pump. Thus, for a liquid dispenser having four pipette heads, there are nine valves. In another embodiment there is only one valve for each pipette, and one additional valve to vent the pump. However, the distribution manifold is not limited to comprising exactly nine or exactly five solenoid valves.

The distribution manifold comprises a microfluidic network 1829 that distributes air evenly amongst the one or more valves that individually regulate air flow to the dispense heads. Thus, by controlling flow of air through the manifold and various valves, pressure above the pipette heads 1803 can be varied so that liquid is drawn up into or expelled from a pipette tip attached to the respective pipette heads. In this way it is not necessary to supply compressed air via an air hose to the liquid dispenser. Neither is it necessary to provide liquid lines to the dispense head. Furthermore, no liquid reagents or liquid samples from the holders enter any part of the liquid dispenser, including the manifold. The volume of liquid drawn into the pipette is less than the maximum volume of the pipette, and therefore overflows are avoided. This aspect reduces complications that would arise if air bubbles are introduced into samples or liquid reagents. An exemplary configuration of a microfluidic network in a distribution manifold is shown in dashed lines in FIG. 15. A microfluidic network is advantageous because it is lightweight and compact, and easy to manufacture.

Pipette Tip Stripper

The liquid dispenser can also operate in conjunction with a motorized plate configured to strip the pipettes and align the pipettes during dispensing of fluid from multiple pipette tips simultaneously, e.g., into a microfluidic cartridge, as further described herein. Such a device is found to be important because the tolerances for incorrect positioning of a pipette tip are very fine.

Figures 16A, 16B:
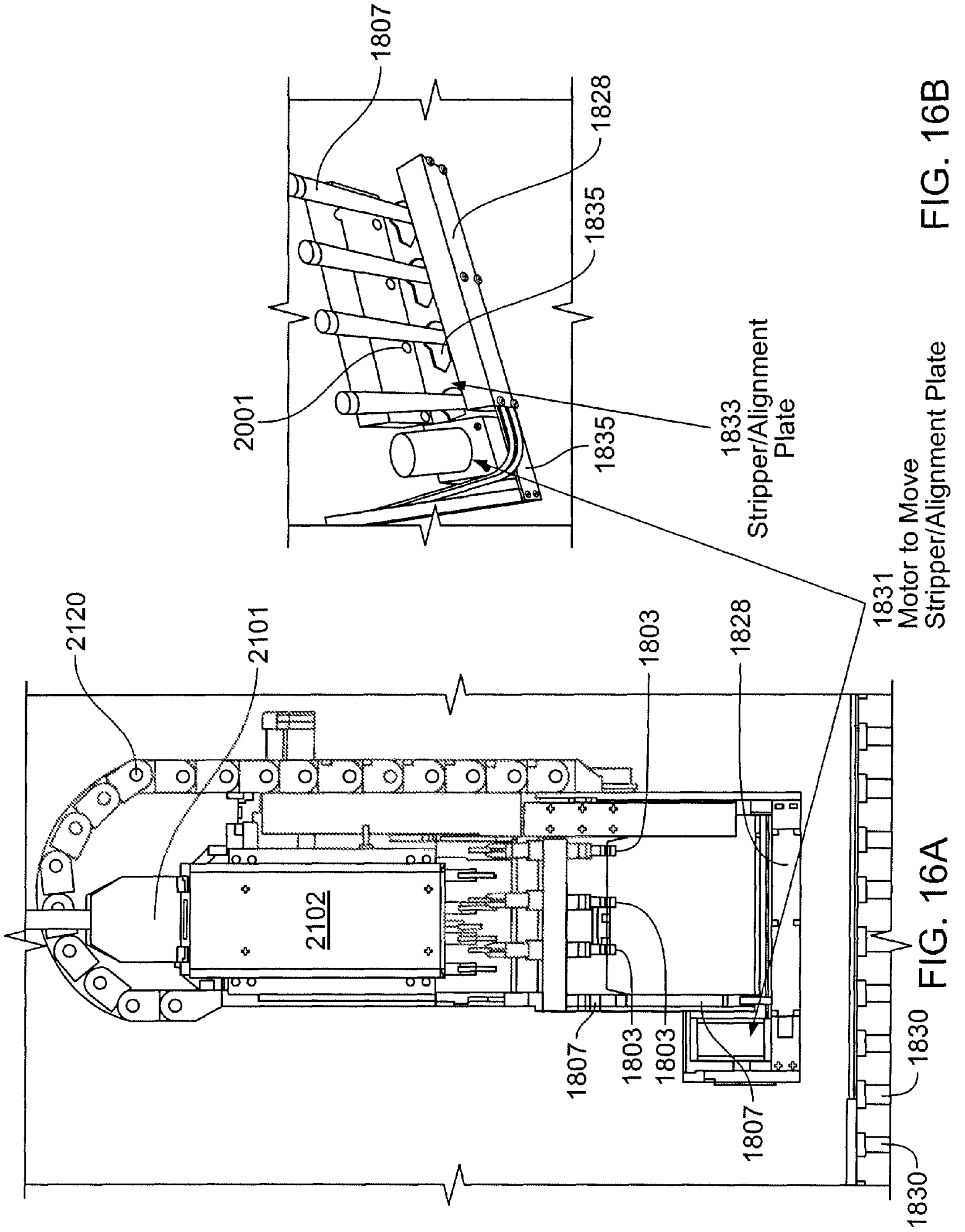
FIGS. 16A and 16B show an exemplary device for stripping pipette tips.

FIGS. 16A and 16B show operation of an exemplary device for stripping pipette tips from a liquid dispenser as further described herein. FIG. 16A is a front plan view of an embodiment of a dispense head, mounted on a gantry, as also shown in FIG. 12. A structure 1828 that holds 4 infra-red detectors for pipette sensing is shown. On the opposite side of structure 1828 (not shown) there are a number of infra-red LED's that send infra-red light towards the infra-red detectors. Typically the number of such LED's is the same as the number of detectors, in this case four. In the presence of pipette tips, an infra-red detector sees a loss of infra-red signal intensity. Also shown in FIG. 16A are sample tubes 1830, configured to accept pipette tips during various pipetting operations.

FIG. 16B shows a perspective view of a pipette stripper. The pipette tips 1807 are aligned, all at the same pitch, above respective sockets (e.g., over a pipette tip sheath) in a holder. A metal plate 1833 having one elongated hole 1835 per pipette tip lies over the sockets. Metal plate 1833 serves to play both alignment and stripping roles. Hole 1835 is configured so that it is wide enough to accommodate a pipette tip, but also has an angled elongated portion that can grip a pipette tip. Electrical connections 1839 to motor 1831, that controls sideways movement of plate 1833, are shown.

Figure 17A:
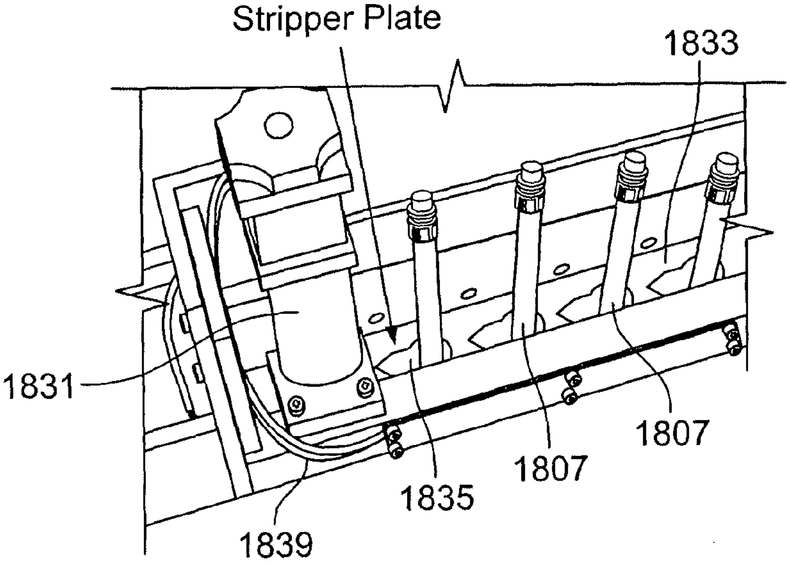
FIGS. 17A-17C show three positions of a stripper/alignment plate during operation of a pipette tip stripper.
Figure 17B:
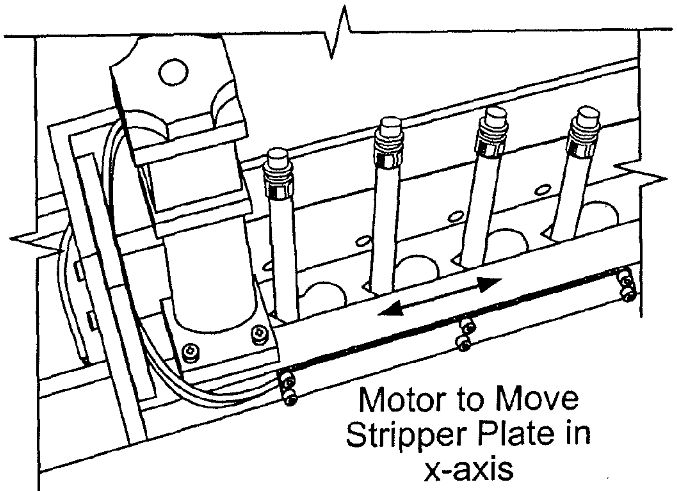

In a stripping role, as illustrated in FIGS. 17A-17B, the pipette tips (attached to the dispense head) are inserted part way down into the sheath through the elongated holes, for example under control of the liquid dispenser herein, and the metal plate is moved sideways, such as under control of a motor 1831, in such a manner that the pipette tips are clamped by the elongated portion of the holes. When the liquid dispenser is moved up, the pipette tips become detached from their respective heads. When the metal plate is subsequently moved back to its initial position, the pipette tips remain in place in their respective sockets.

Figure 17C:
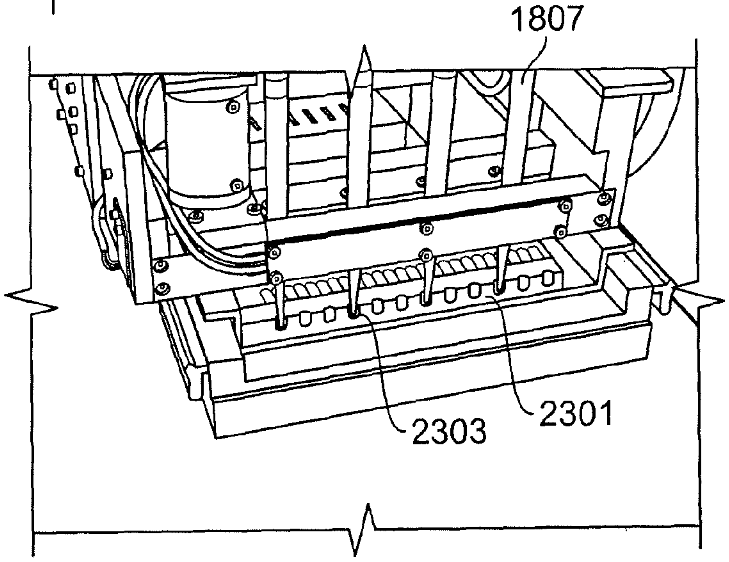

In an aligning role, shown in FIGS. 17A-17B, similar operations are performed except that the metal plate is moved sideways sufficiently to contact each pipette tip but not so far as to clamp any tip. The motion of the plate is such that the tips become aligned with respect to one another. FIG. 17C shows an outcome of aligning four pipette tips; the tips are positioned over four respective inlets 2303 of a microfluidic cartridge 2301, so that liquid can be loaded into the cartridge by interfacing the pipette tips with dedicated inlet holes, such as conical inlet holes, on the cartridge.

In certain embodiments, the liquid dispenser can also comprise one or more sensors 2001 (e.g., infra-red sensors) each of which detects the presence of a pipette tip 2005 in position beneath the dispense heads, such as in one or more holders in a rack as further described herein. This is important to ensure that the processor knows affirmatively that a pipette tip is present or missing. Since a pipette tip is picked up by application of mechanical force of a head against the pipette, and is also dispensed using mechanical motion of a stripper plate, sensing a pipette tip helps prevent mechanical errors such as having a head descend too far and become damaged. The embodiment in FIG. 18 shows 4 infrared sensors 2001 for detecting the presence of pipettes attached to the 4 pipette heads.

Such sensors can be mounted in close proximity to the pipette tip stripper described elsewhere herein. In FIG. 18, for example, an infra-red sensor 2001 can have an infra-red emitter 2003 (not shown, but on the reverse side of plate 2000) placed opposed to it, so that the presence of disposable pipette tip 1807 obstructs the line of sight between the emitter and the detector, thus enabling determination of the presence or absence of the pipette tip. The disposal pipettes are configured perpendicular to pipette stripper-alignment plate 1833 as further described herein.

Figure 18:
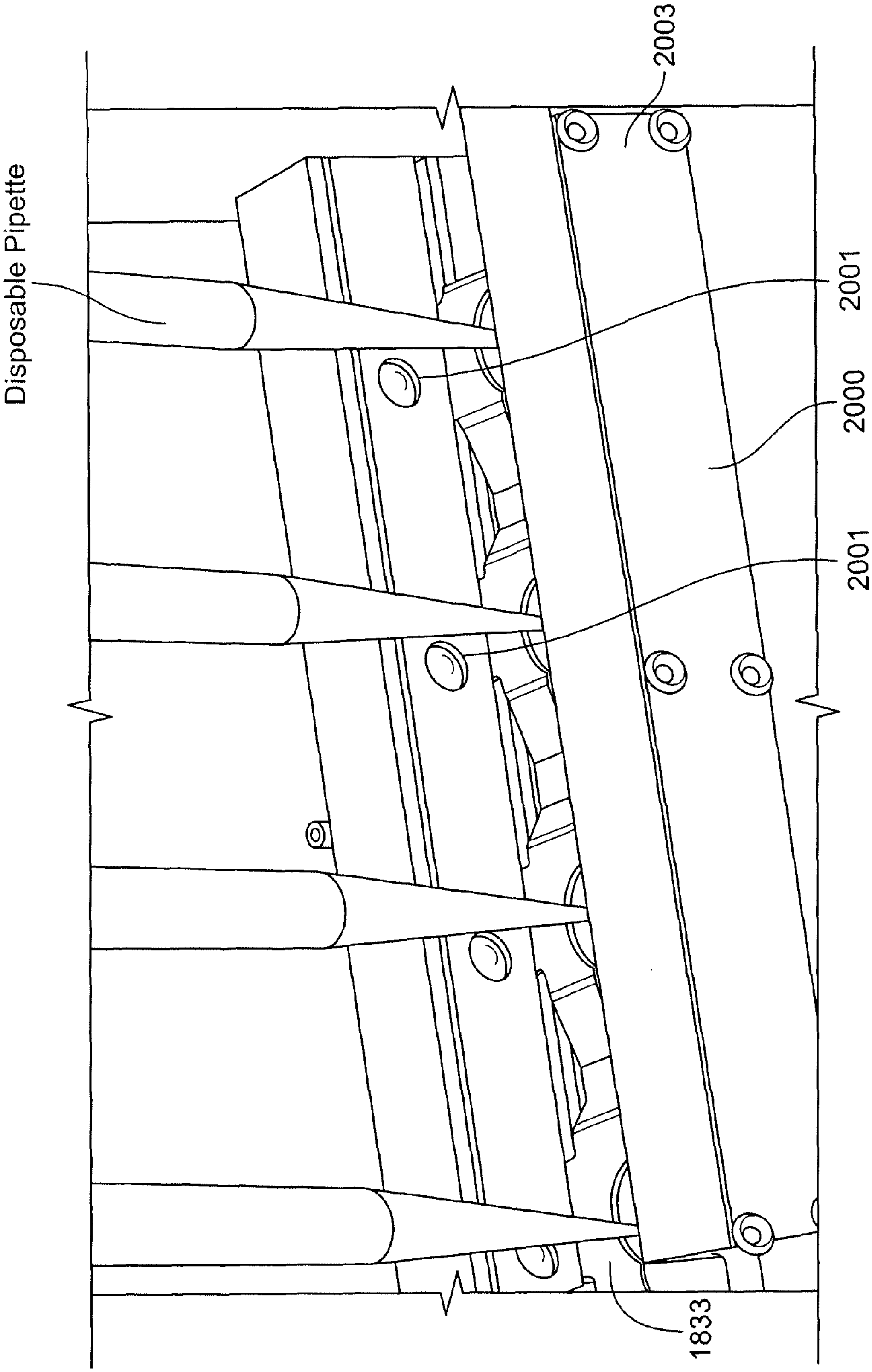
FIG. 18 shows a pipette tip stripper, and pipette tip sensors.

The embodiment shown in FIG. 18 has a stripper/alignment plate 1833 that is not flat but undulating. In other embodiments, the stripper plate can be flat, grooved, or have other shapes, such as having a wedge-shaped cross-section.

Sample Identification Verifier

Another aspect of the apparatus relates to a sample identification verifier configured to check the identity of each of the number of samples, and typically mounted on one face of the liquid dispenser, the face and location on the face being determined by other geometric features of the apparatus and its various components, as may be routinely optimized by those of skill in the art. Such sample identification verifiers can be optical character readers, bar code readers, or radio frequency tag readers, or other suitable readers, as available to one of ordinary skill in the art. A sample identification verifier can be mounted on the gantry to which the liquid dispenser is mounted, or attached to the liquid dispenser so that it moves in concert with the liquid dispenser. Alternatively, the sample identification verifier can be separately mounted and can move independently of the liquid dispenser.

Figure 19:
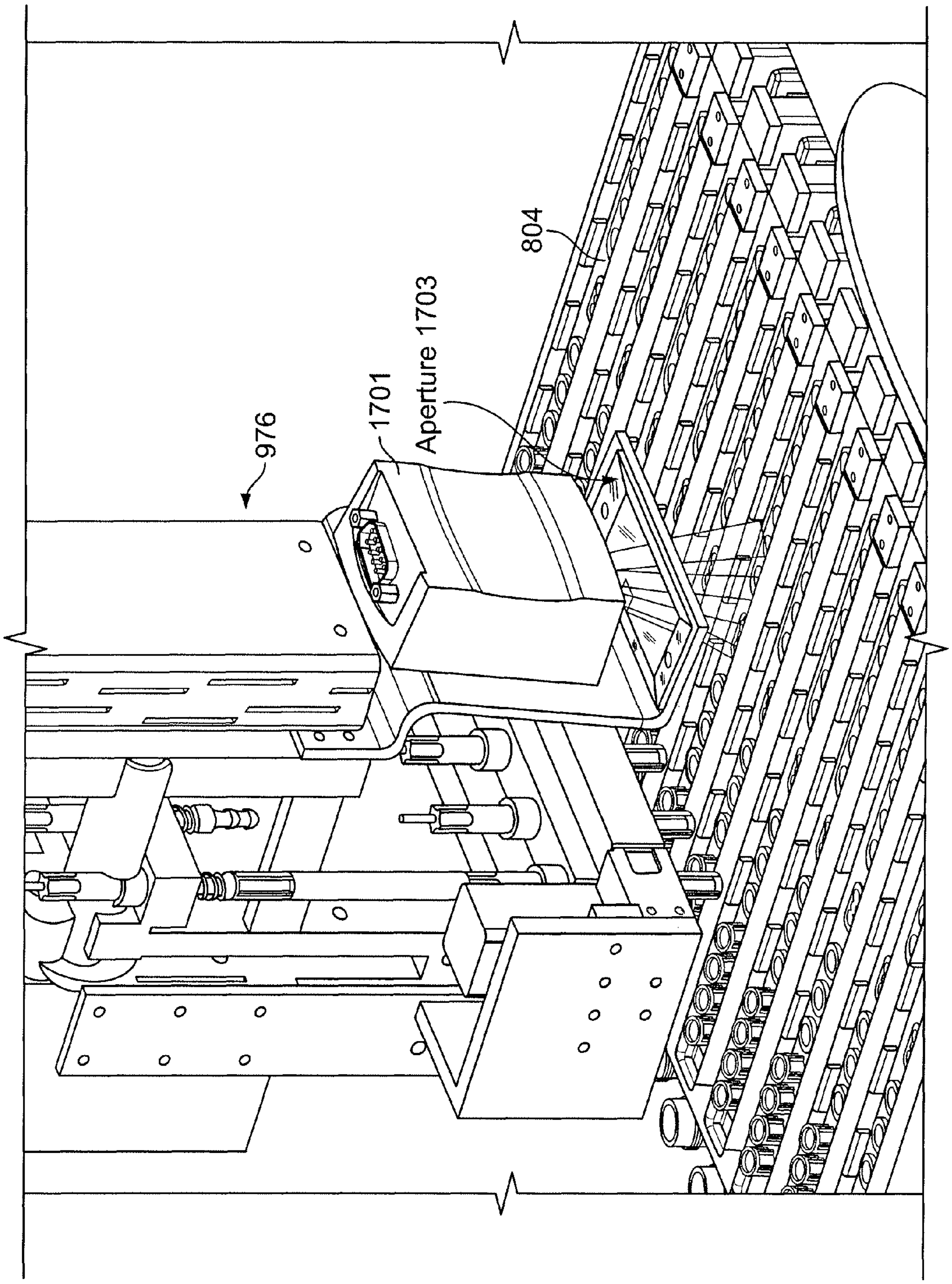
FIG. 19 shows a scanning read-head attached to a liquid dispense head, positioned over a number of reagent holders.
Figure 20:
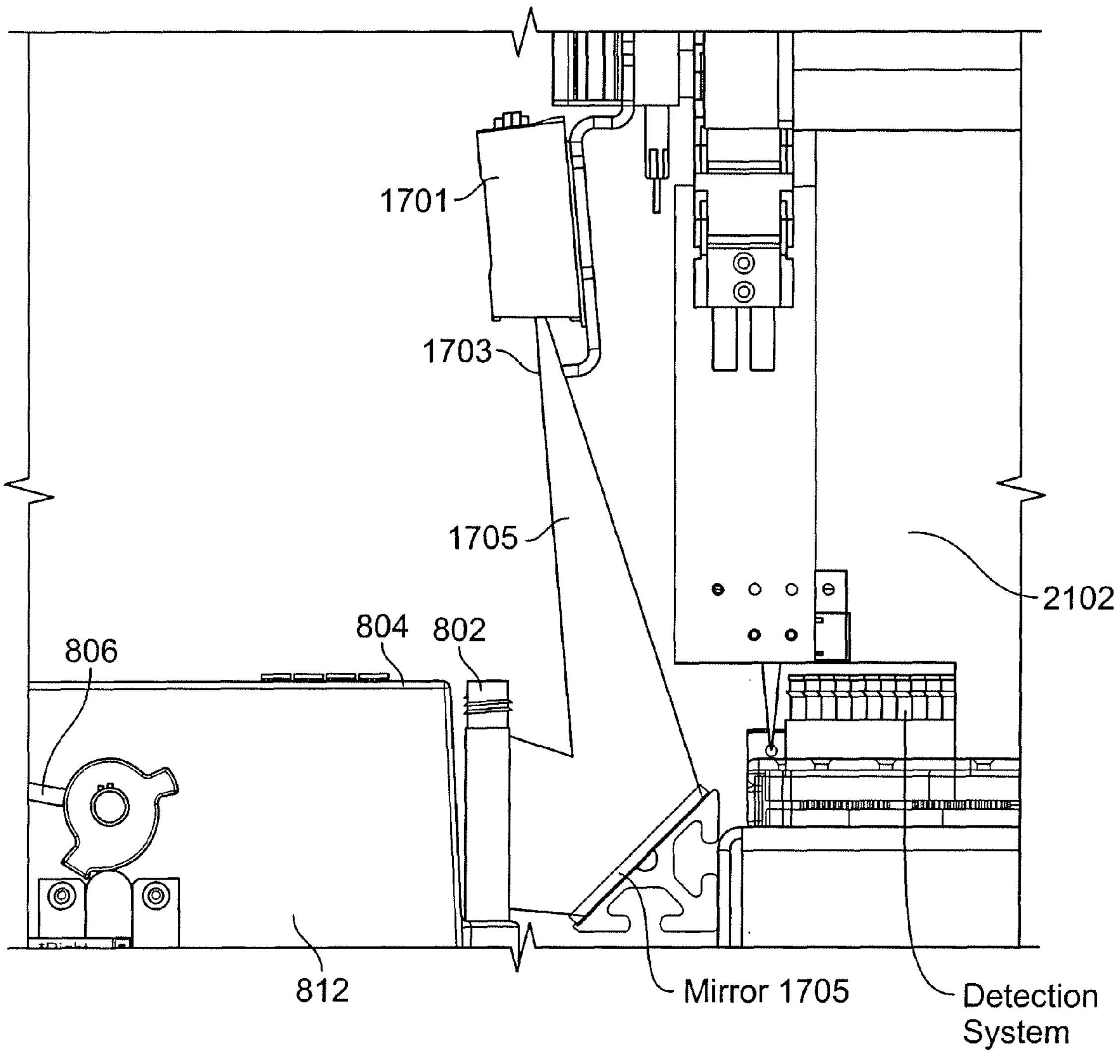
FIG. 20 shows a scanner in side view, positioned to read identifiers on one or more sample tubes.

In FIGS. 19 and 20, for example, sample identification verifier 1701 is a bar-code reader attached to the liquid dispenser. In FIG. 19, the dispense head is positioned over several reagent holders 804, mounted in a rack in a diagnostic apparatus. The sample identification verifier is similarly positioned, such that it can read labels situated on the tops of the various holders 804. Aperture 1703 determines the field of view of the verifier.

In the view of FIG. 20, the verifier is positioned to read identifying marks on sample tubes 802. The field of view 1705 of barcode scanner 1701 is non-linear, enabling it to detect light reflected by mirror 1705 from, e.g., a the barcoded clinical sample tube 802, in disposable rack 812. The barcode scanner reads the barcode on the clinical sample tube thus identifying the presence and specifics of the sample tube. Because of use of a mirror, the scanner is configured either to read a bar-code, or a 2-D barcode, printed in mirror image form (that is thus reflected into normal form by the mirror), or to read a mirror image of a normal bar-code and to convert the mirror image to unreflected form via a computer algorithm.

Figure 21:
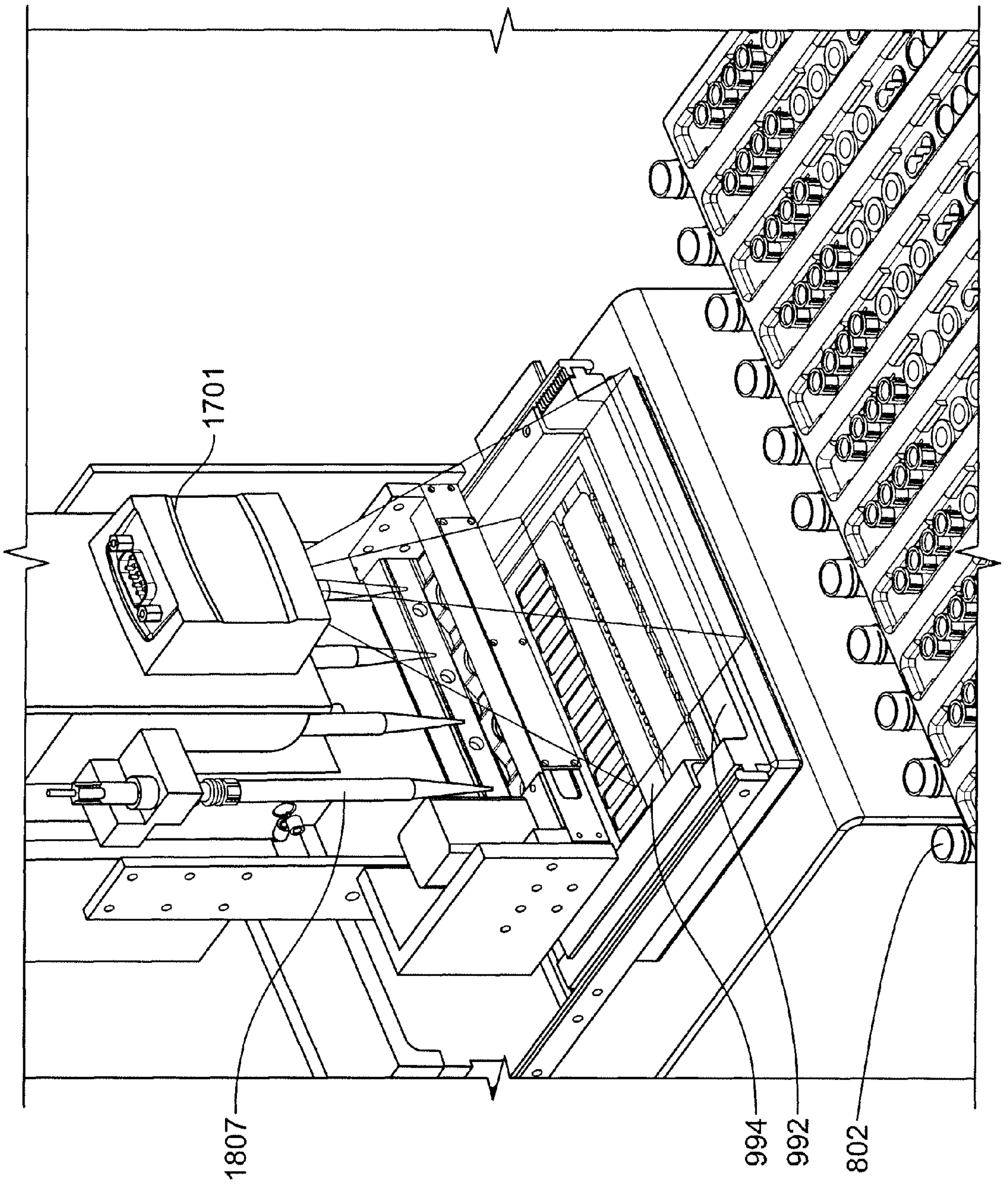
FIG. 21 shows a scanner positioned above a microfluidic cartridge.

In FIG. 21, the sample identification verifier is positioned to read indicia from a microfluidic cartridge 994, located in a receiving bay 992.

The verifier is typically mounted so that freedom of motion along the z-axis permits it to be readily positioned to read the sample tube, holder, and cartridge barcodes.

Sample identification verifier is configured to communicate details of labels that it has detected or read to a processor 980 or controller in the apparatus, thereby permitting sample identifying information to be associated with diagnostic results and other information relating to sample preparation, and extraction and amplification of nucleic acid therein.

Processor and Control

Control of automated motions of the liquid dispenser of the automated pipetting apparatus is via a suitably configured processor. The processor has been configured to execute instructions that deliver control signals to the various motors, and to receive signals from the various sensors, within the automated pipetting apparatus. Design and manufacture of such a processor is within the capability of one of ordinary skill in the art of laboratory automation systems, or apparatus control systems. The instructions executed by the processor can, similarly, be designed and implemented by one of ordinary skill in the art of computer programming. The instructions can take into account desired protocols of varying natures, depending on numbers of samples, locations of samples, and nature of target nucleotides, and cause motions of the liquid dispense head. The instructions can also take into account signals received from one or more sensors, in order to determine which of one or more next steps to execute, or whether to execute such steps at all or to instead, issue an error notification. The instructions may provide to a user a menu of pre-determined protocols to choose from and to execute, or may permit a user to design a new protocol, or modify an existing one.

Microfluidic Cartridge

As described elsewhere herein, the liquid dispenser can be configured to deliver quantities of solution containing one or more polynucleotide(s) in a form suitable for amplification to a microfluidic cartridge. Typically, such delivery occurs for multiple quantities of solution in parallel. A microfluidic cartridge compatible with such a process typically has a number of inlets, corresponding to a practical number of samples that are to be processed in parallel, for example, 2, 4, 6, 8, 10, 12, 16, or 24. Each inlet is situated in a lane of the cartridge, each lane further having channels that divert the respective samples to respective chambers within which an amplification such as PCR can be performed. The chambers typically can be isolated by one or more valves, during amplification. The chambers are also typically situated so that the progress of amplification can be monitored by one or more detectors. Exemplary configurations and manufactures of cartridges are described elsewhere, including but not limited to U.S. patent application Ser. Nos. 12/173,023, filed on Jul. 14, 2008, and Ser. No. 11/985,577, filed Nov. 14, 2007, both of which are incorporated herein by reference.

Typically, the inlet separation on the cartridge, or other receiving area, is chosen to correspond to the separation between adjacent pipette tips on the dispense heads of the liquid dispenser, or some convenient fraction or multiple thereof. Thus, for example, for a cartridge having an 8 mm separation between adjacent inlets, used in conjunction with a liquid dispenser having a 24 mm separation between the centers of the tips of adjacent pipette tips, the liquid dispenser can dispense samples into cartridge inlets that are separated by two inlets (e.g., a first and fourth inlets, numbering from a particular end of the cartridge). It would be understood that these dimensions and multiples are not limiting.

The apparatus having been described, it is illustrated by way of the following non-limiting examples.

EXAMPLES

Example 1

Exemplary Chemistry and Processes of Use

Chemistry Overview

The chemistry processes typically carried out with the apparatus described herein center around the detection and identification of organisms in a clinical specimen, by virtue of detecting nucleic acids from the organism in question. This involves isolation of nucleic acids from target organisms that are contained in a clinical specimen, followed by a process that will detect the presence of specific nucleic acid sequences. In addition to target detection, an internal positive control nucleic acid can be added to the collection buffer, and can thereby be taken through the entire extraction and detection process along with target nucleic acids. This control will monitor the effectiveness of the entire process and will minimize the risk of having false negative results.

Nucleic Acid Extraction and Purification

Nucleic acid extraction procedures begin with the addition of a clinical specimen to a prepared specimen collection solution. This can be done either at a specimen collection site, or at the testing site. Two collection solution formats can be available: one for body fluids, and one for swab specimens. Collection solutions used at collection sites will serve as specimen transport solutions, and therefore, this solution must maintain specimen and analyte integrity.

The extraction and purification procedure, which is entirely automated using a liquid dispenser as described herein, in conjunction with a suitable heater and separator, proceeds as follows:

Target organisms are lysed by heating the detergent-containing collection solution.

Magnetic beads, added to the specimen/collection solution mix, non-specifically bind all DNA that is released into the solution.

Magnetic beads are isolated and are washed to eliminate contaminants

DNA is released from the beads using high pH and heat.

DNA containing solution is removed and neutralized with a buffer

Nucleic Acid Amplification

Nucleic acids that have been captured by magnetic beads, washed, released in high pH, and neutralized with buffer, are added to a mixture of buffers, salts, and enzymes that have been lyophilized in a tube. The mixture is rapidly rehydrated, and then a portion of the solution is loaded onto a microfluidic cartridge. The cartridge is then loaded into the amplification instrument module, which consists of a heating unit capable of thermal cycling, and an optical detection system. Detection of target nucleic acids proceeds as follows:

The liquid is sealed in a reaction chamber.

Rapid thermal cycling is used to potentiate the Polymerase Chain Reaction (PCR), which is used to amplify specific target DNA.

Amplified DNA fluoresces, and can be detected by optical sensors.

A fluorescent probe "tail" is incorporated into each amplified piece of DNA

At a specific temperature, the probe adopts a conformation that produces fluorescence (this is termed a "scorpion" reaction).

Fluorescence is detected and monitored throughout the reaction.

Extraction and Amplification/Detection Process

Extensive bench-scale testing has been performed to optimize the nucleic acid extraction chemistry, including the collection buffer, the wash buffer formulation, the release solution formulation, and the PCR reagent mixes. The fully automated method of extraction, followed by 12-up PCR, was able to provide very high sensitivity consistently at 150 copies/sample.

Examplary target/sample combinations include: Chlamydia in Urine (50/50); Gonrorrhoea in Urine; GBS in Plasma.

Various detection chemistries such as Taqman, Scorpion, and SYBRg Green work reliably in the microfluidic cartridge.

Example 2

Exemplary Chemistry Processes Performed by an Automated Instrument

Sample Pre-Processing

For Urine Sample: Take 0.5 ml of urine and mix it with 0.5 ml of collection buffer. Filter the sample through a pre-filter (containing two membranes of 10 micron and 3 micron pore size).

For Plasma Sample: Take 0.5 ml of plasma and mix it with 0.5 ml of collection buffer.

For GBS swab samples: Take the swab sample and dip it in 1 ml of collection buffer.

For each type of sample, after it is mixed with the appropriate collection buffer (and filtered if applicable), the solution is placed in the external sample tube in the position specified for it in the rack.

The sample collection buffer contains 50 mM Tris pH 7, 1% Triton X-100, 20 mM Citrate, 20 mM Borate, 100 mM EDTA, plus 1,000 copies of positive control DNA.

Loading the Instrument and Starting Sample Processing

The following steps may be performed to initiate an analysis on samples in batch.

1. Load PCR tube containing PCR master mix in one of the specified snap-in location of the reagent holder.
2. Load PCR tube containing PCR probes and primers for the target analyte under consideration in the specified location of the reagent holder.
3. In case of two analyte test, load PCR tube containing probes and primers for second analyte in the specified location of the reagent holder.
4. Insert the reagent holder in a rack, typically a 12-holder rack, in the same lane as the sample tube under consideration.
5. Prepare and insert reagent holders for other samples in consideration.
6. Load the rack in one of the locations in the instrument.
7. Load a cartridge in the cartridge tray loading position. Typically the cartridge has the same number of lanes as the rack; thus a 12-sample cartridge is used in conjunction with a 12-holder rack.
8. Start operation.

Liquid Processing Steps

The following steps may be performed to carry out sample preparation. Herein the numbering of the pipette tips refers to those pipette tips that are stored in a reagent holder, for example, in a pipette sheath of such a holder. It would be understood that such operations could be performed multiply in parallel by a liquid dispenser as described elsewhere herein. References to a 'robot' herein are intended to mean an automated pipetting apparatus, such as embodiments further described herein.

1. Using Pipette tip #1, the robot transfers the clinical sample from the external sample tube to the process tube of the reagent holder.
2. Using the same pipette tip, the robot takes about 100 μl of sample, mixes the lyophilized enzyme and affinity beads, transfers the reagents to the process tube. Mixing is performed in the process tube by 5 suck and dispense operations.
3. The robot places pipette tip #1 at its designated location in the reagent holder.
4. Heat the process tube to 60° C. and maintain it for 10 minutes.

5. After 5 minute of lysis, the robot picks up pipette tip #1 and mixes the contents by 3 suck and dispense operations.
6. The robot places pipette tip #1 at its designated location in the reagent holder.
7. After 10 minutes of lysis, a magnet is moved up the side of the process tube to a middle height of the sample and held at that position for a minute to capture all the magnetic beads against the wall the tube.
8. The magnet is brought down slowly to slide the captured beads close to the bottom (but not the bottom) of the tube.
9. Using pipette tip #2, aspirate all the liquid and dump it into the waste tube.
10. Aspirate a second time to remove as much liquid as possible from the process tube.
11. Using the same pipette tip #2, withdraw 100 μl of wash buffer and dispense it in the process tube. During this dispense, the magnet is moved downwards, away from the process tube.
12. Perform 15 mix steps to thoroughly mix the magnetic beads with the wash buffer.
13. Wait for 30 seconds.
14. Move magnet up to capture the beads to the side and hold for 15 seconds.
15. Using pipette tip #2, aspirate wash buffer twice to remove as much liquid as possible and dump it back in the wash tube.
16. Move magnet down away from the process tube.
17. Place pipette tip #2 in its specified location of the reagent holder.
18. Pick up a new pipette tip (tip #3) and withdraw 8-10 μl of release buffer and dispense it over the beads in the process tube.
19. Wait for 1 minute and then perform 45 mixes.
20. Heat the release solution to 85° C. and maintain temperature for 5 minutes.
21. Place pipette tip #3 in its specified location of the reagent holder.
22. Bring magnet up the tube, capture all the beads against the tube wall and move it up and away from the bottom of the tube.
23. Pick up a new pipette tip (tip #4) and withdraw all the release buffer from the process tube and then withdraw 3-10 μl of neutralization buffer, mix it in the pipette tip and dispense it in the PCR tube. (In case of two analyte detections, dispense half of the neutralized DNA solution into first PCR tube and the rest of the solution in the second PCR tube.)
24. Using pipette tip #4, mix the neutralized DNA with the lyophilized reagents by 4-5 suck and dispense operations and withdraw the entire solution in the pipette tip.
25. Using pipette tip #4, load 6 μl of the final PCR solution in a lane of the 12-up cartridge.

Real-Time PCR

After all the appropriate PCR lanes of the PCR cartridge are loaded with final PCR solution, the tray containing the cartridge moves the cartridge into the PCR Analyzer. The cartridge is pressed by an optical detection read-head against the PCR heater. Heaters activate valves to close either ends of the PCR reactor and the real-time thermocycling process starts. After completing appropriate PCR cycles (~45 cycles), the analyzer decides whether the sample has the target DNA based on the output fluorescence data, and issues an indication of the same.

Example 3

Reagent Holder

An exemplary reagent holder consistent with the description herein has the following dimensions and capacities:

180 mm long×22 mm wide×100 mm tall;

Made from Polypropylene.

One snapped-in low binding 1.7 ml tube that functions as a process tube.

3 built-in tubes that function as receptacles for reagents, as follows:
- One tube containing 200-1000 μl of wash buffer (0.1 mM Tris, pH 8).
- One tube containing 200-1000 μl of release solution (40 mM NaOH).
- One tube containing 200-1000 ml of neutralization solution (330 mM Tris, pH 8.0).

One built-in tube that functions as a waste chamber (will hold ~4 ml of liquid waste).

3 receptacles to accept containers for solid reagents. Snap-in 0.3 ml or 0.65 ml PCR tubes (which are typically stored separately from the reagent holder) are placed in each of these locations, and contain, respectively:
- lyophilized sample preparation reagents (lysis enzyme mix and magnetic affinity beads).
- First lyophilized PCR master mix, probes and primers for a first target analyte detection.
- Second lyophilized PCR master mix, probes and primers for a second target analyte detection (only offered in select cases, such as detection of Chlamydia and Gonorrhea from urine).

4 pipette tips located in 4 respective sockets.

Pipette tip Sheath: The pipette tips have a sheath/drip tray underneath to help capture any drip from the pipette tips after being used, and also to prevent unwanted contamination of the instrument.

Handle and Flex-Lock allows easy insertion, removal, and positive location of strip in rack.

One or more labels: positioned upward facing to facilitate ease of reading by eye and/or, e.g., a bar-code reader, the one or more labels containing human and machine readable information pertaining to the analysis to be performed.

It is to be understood that these dimensions are exemplary. However, it is particularly desirable to ensure that a holder does not exceed these dimensions so that a rack and an apparatus that accommodates the reagent holder(s) does not become inconveniently large, and can be suitably situated in a laboratory, e.g., on a bench-top.

Example 4

Exemplary Foil-Sealing of Buffer Containing Reagent Tubes

Tubes containing buffers have to be sealed with high moisture vapor barrier materials in order to retain the liquid over a long period of time. Reagent holders may need to have a shelf life of 1-2 years, and as such, they should not lose more than say 10-15% of the liquid volume over the time period, to maintain required volume of liquid, and to maintain the concentration of various molecules present in the solution. Moreover, the materials used for construction of the tube as well as the sealing laminate should not react with the liquid buffer. Special plastic laminates may provide the moisture barrier but they may have to be very thick (more than 300 μm thick), causing the piercing force to go up tremendously, or of special, expensive polymer (such as Aclar). Aluminum foils, even a thin foil of a few hundred angstrom provides an effective moisture barrier but bare aluminum reacts with some liquid buffers, such as sodium hydroxide, even an aluminum foil with a sprayed coating of a non-reactive polymer may not be able to withstand the corrosive vapors over a long time. They may react through tiny pin holes present in the coating and may fail as a barrier over time.

For these reasons, aluminum foils with a laminate structure have been identified as a suitable barrier, exemplary properties of which are described below:

1. Sealing

Heat seals to unitized polypropylene strip (sealing temp ~170-180° C.)

No wrinkling, cracking and crazing of the foil after sealing

2. Moisture Vapor Transmission Rate (MVTR)

Loss of less than 10% liquid (20 microliters from a volume of 200 microliter) for a period of 1 year stored at ambient temperature and pressure. (effective area of transport is ~63 $mm^2$); Approximate MVTR ~0.8 $cc/m^2/day$ 3. Chemistry Ability to not react with 40 mM Sodium Hydroxide (pH<12.6): foil should have a plastic laminate at least 15 microns thick closer to the sealed fluid. Ability to not react with other buffers containing mild detergents 4. Puncture Ability to puncture using a p1000 pipette with a force less than 3 lb Before puncturing, a fully supported membrane 8 mm in diameter will not stretch more than 5 mm in the orthogonal direction After puncturing, the foil should not seal the pipette tip around the circumference of the pipette.

5. Other Features

Pin-hole free

No bubbles in case of multi-laminate structures.

Example 5

Illustrative Mechanism of Piercing Through a Plasticized Laminate and Withdrawing Liquid Buffer The aluminum laminate containing a plastic film described elsewhere herein serves well for not reacting with corrosive reagents such as buffers containing NaOH, and having the favorable properties of pierceability and acting as a moisture barrier. However, it presents some additional difficulties during piercing. The aluminum foil tends to burst into an irregular polygonal pattern bigger than the diameter of the pipette, whereas the plastic film tends to wrap around the pipette tip with minimal gap between the pipette and the plastic film. The diameter of the hole in the plastic film is similar to the maximum diameter of the pipette that had crossed through the laminate. This wrapping of the pipette causes difficulty in dispensing and pipetting operations unless there is a vent hole allowing pressures to equilibrate between outside of the tube and the air inside of the tube.

A strategy for successful pipetting of fluid is as follows:

1. Pierce through the laminate structure and have the pipette go close to the bottom of the reagent tube so that the hole created in the laminate is almost as big as the maximum diameter of the pipette (e.g., ~6 mm for a p1000 pipette)
2. Withdraw the pipette up a short distance so that a small annular vent hole is left between the pipette and the laminate. The p1000 pipette has a smallest outer diameter of 1 mm and maximum outer diameter of 6 mm and the conical section of the pipette is about 28 mm long. A vent hole thickness of a hundred microns is enough to create a reliable vent hole. This corresponds to the pipette inserted to a diameter of 5.8 mm, leaving an annulus of 0.1 mm around it.
3. Withdraw fluid from the tube. Note that the tube is designed to hold more fluid than is necessary to withdraw from it for a typical sample preparation procedure.

Example 6

Exemplary Foil Piercing and Dissolution of Lyophilized Reagents

The containers of lyophilized reagents provided in conjunction with a holder as described herein are typically sealed by a non-plasticized aluminum foil (i.e., not a laminate as is used to seal the reagent tubes). Aluminum foil bursts into an irregular polygonal pattern when pierced through a pipette and leaves an air vent even though the pipette is moved to the bottom of the tube. In order to save on reagents, it is desirable to dissolve the reagents and maximize the amount withdrawn from the tube. To accomplish this, a star-ridged (stellated) pattern is placed at the bottom of the container to maximize liquid volume withdrawn, and flow velocity in between the ridges.

Exemplary steps for dissolving and withdrawing fluid are as follows:

1. Pierce through the pipette and dispense the fluid away from the lyophilized material. If the pipette goes below the level of the lyophilized material, it will go into the pipette and may cause jamming of the liquid flow out of the pipette.
2. Let the lyophilized material dissolve for a few seconds.
3. Move pipette down touching the ridged-bottom of the tube. The pipette stops moving when it senses an opposition to its motion, such as by a force sensor described elsewhere herein.
4. Perform an adequate number of suck and spit operations (such as 4-10) to thoroughly mix the reagents with the liquid buffer.
5. Withdraw all the reagents and move pipette to dispense it into the next processing tube.

Example 7

Exemplary Force Sensing of the Pipette Head

Travel of the liquid dispenser along the z-axis is regulated by a force-sensor. A force sensor is interfaced with the pipette heads in such a way that any time the pipette head seats against the disposable pipette tip(s) or the picked pipettes are forced through a laminate cover of the reagent holder, or the pipette tip is forced against the bottom of the tubes in the reagent disposable, an upward force acts on the pipette head through the pipette holding nozzle or the pipette tip itself. The entire head is pivoted at a lower point, and any force acting on the head causes a set-screw on the upper part of the head to press against a force sensor. This force sensor is calibrated for vertical displacement of the head against a non-moving surface. Using this calibration, it can be determined when to stop moving the head in the z-direction by detecting whether, for example, a pipette is properly seated or if a pipette tip has hit a tube bottom.

Example 8

Exemplary Alignment of Pipette Tips while Loading PCR Reagent Solutions into a Microfluidic Cartridge The liquid dispenser is configured so that, when multiple pipette tips are attached simultaneously, the tips can dispense in parallel to multiple inlets on a microfluidic cartridge. In particular, this means that the spacing between the tips is exactly the same as, or the same as to within an acceptable tolerance, the spacing between the inlets on the cartridge. Larger volume pipette tips can be as long as 95 mm (for, e.g., a p1000 pipette). When 4 long pipette tips are sprung from the head, even a 1° misalignment during seating can cause the tip to be off-center by ~1.7 mm, which is sufficient for that tip to miss the desired inlet on the cartridge. As it is difficult to have perfect alignment all the time during pipetting of the tip both at its top where it is interfaced with the tip holder and its bottom, it becomes necessary to mechanically constrain all the tips at another location closer to the bottom. As described elsewhere herein, a stripper plate having a defined hole structure, can be used to align all the tips. The stripper plate holes clear all the 4 pipette tips when they are picked up. After the tips are properly seated, the stripper plate is moved horizontally, such as in the x-axis direction, using a motor to move all the pipettes against the notches provided in the stripper plate. Now all the pipettes land on the cartridge inlet holes with ease.

Example 9

Exemplary Apparatus Including an Automated Pipetting System

Described herein are exemplary specifications for the mechanical design of a system for carrying out PCR on multiple samples. In some embodiments, the system can be about 28.5 inches deep, or less, and about 43 inches wide, or less, and weight about 250 pounds or less. The system can be designed with a useful life of about 5 years (e.g., assuming 16,000 tests per year) and can be designed such that the sound level for this instrument (during operation) does not exceed 50 dB as measured 12 inches from the instrument in all ordinate directions. In some embodiments, the exterior of the system can be white with texture.

Referring to the overall system, in some embodiments, critical components of the system can remain orthogonal or parallel (as appropriate) to within 0.04 degrees. Exemplary critical components can include motion rails, pipettes, nozzles (e.g., axially as individual nozzles, linearly as an array of four nozzle centroids, or the like), lysis heaters, major edges of the installed cartridge holder in the reader drawer, the front face of the separation magnets, and the like.

In the following descriptions as with elsewhere herein, the X-axis (or X direction) refers to the axis extending from left to right when facing the front of the system, the Y-axis (or Y direction) refers to the axis extending from back to front when facing the front of the system, and the Z-axis (or Z direction) refers to the axis extending up from the bottom when facing the front of the system. As viewed from the top of the instrument, the centroid of the leftmost pipette nozzle on the Z-payload (as viewed from the front of the instrument) can be capable of unobstructed travel in the X direction from a point 80 mm from the outermost left baseplate edge to a point 608 mm from the outermost left baseplate edge and can be capable of unobstructed travel in the Y direction from a point 60 mm from the outermost front baseplate edge to a point 410 mm from the outermost front baseplate edge.

Still referring to the system, as viewed from the front of the instrument, the bottom-most face of the pipette nozzles on the Z-payload can be capable of unobstructed travel in the Y direction from a point 156 mm above the top surface of the baseplate to a point 256 mm above the top surface of the baseplate. The 1 ml pipette tips can be capable of penetrating the foil covers included on disposable reagent strips. This penetration may not create contamination, affect the associated chemistries, or damage the pipette tips. Motions can be executed in such a manner as to eliminate mechanical hysteresis, as needed. Gantry motions can be optimized to prevent cross lane contamination and carryover. The rack can align the reagent strips to a tolerance of +/−0.010 inches in the X and Y directions.

Referring now to the gantry, in some embodiments, the gantry can consist of a stepper-motor actuated, belt/screw-driven cartesian robotic system. The gantry can be free to move, with or without attachments, above the modules that are forward of the rear facade and below the bottom-most horizontal face on the Z head, so long as the Z-payload is fully retracted. The gantry can be capable of travel speeds up to about 500 mm/sec in the X and Y directions and up to about 100 mm/sec in the Z direction. The accuracy and precision of the axis motions (e.g., with respect to the X, Y, and Z home sensors) can be 25 mm or better for each axis, and can be retained throughout the maintenance period. The axis drive belts may not leave residue in areas where PCR and samples are processed. The gantry can contain provisions for routing its own and all Z-payload wire harnesses back to the instrument. Belt tension on the X and Y axes can be set at 41.5+/−3.5 pounds.

Referring now to the Z-payload, the fluid head can have 4 pipette attachment nozzles located at 24 mm distances between adjacent centers. Such a distance is chosen to facilitate interfacing the pipette tips and inlets on a microfluidic cartridge, as well as between sample tubes, or reagent tubes, on adjacent holders. Exemplary pipette tips that the pipette nozzles can capture without leakage include Biorobotix tips PN23500048 (50 μL), PN23500049 (1.75 μL), and PN23500046 (1 ml). The Z payload can incorporate a stepper actuated stripper plate capable of removing pipette tips (e.g., the pipette tips described hereinabove). The system can include a pump and manifold system that includes software controlled aspiration, dispensing, and venting of individual fluid volumes within each of the four individual tips and simultaneous dispensing and venting on all tips. The pump and manifold system can have an accuracy and precision of about +/−2 μL per tip for volumes that are less than 20 μL and about +/−10% for volumes greater than or equal to 20 μL (e.g., when aspirating or dispensing in individual tips). The total pump stroke volume can be greater than about 8 μl, and less than about 1250 μL. The minimum aspirate and dispense speed can be about 10 μL/sec to about 300 μL/sec. The centroid of the bottom-most face of each pipette tip can be axially aligned with the nozzle centroid of the pipette nozzles within 0.2 mm. The bottom-most pipette tip faces can be co-planar within 0.2 mm. The Z-payload can incorporate a Z axis force sensor capable of feedback to software for applied forces of between about 0 and 4 lbs. The Z-payload can incorporate a downward facing barcode reader capable of reading the system barcodes as described elsewhere herein.

Referring now to racks included in the system, disposable reagent strips (e.g., oriented orthogonally to the front of the instrument) can be contained in 2, 12-lane racks. The 12 reagent strips in a given rack can register and lock into the rack upon insertion by a user. The rack can contain an area for 12 sample lysis tubes and hold the tube bottoms co-planar, allowing the user to orient the bar code to face the rear of the instrument. Certain features, including those listed above, can allow the racks to be inserted and oriented in the instrument by a minimally trained user. Proper rack placement can be confirmed by feedback to the software. In some embodiments, the racks can be black and color fast (e.g, the color may not appreciably degrade with use or washing with a 10% bleach solution) and the rack material can be dimensionally stable within 0.1 mm over the operating temperature range of the system. The rack can be designed with provisions to allow the rack to be carried to and from the instrument and to minimize or eliminate the likelihood that the tubes held by the rack will spill when placed on a flat surface.

Example 10

Exemplary Pipette Tip Usage

Figure 22A:
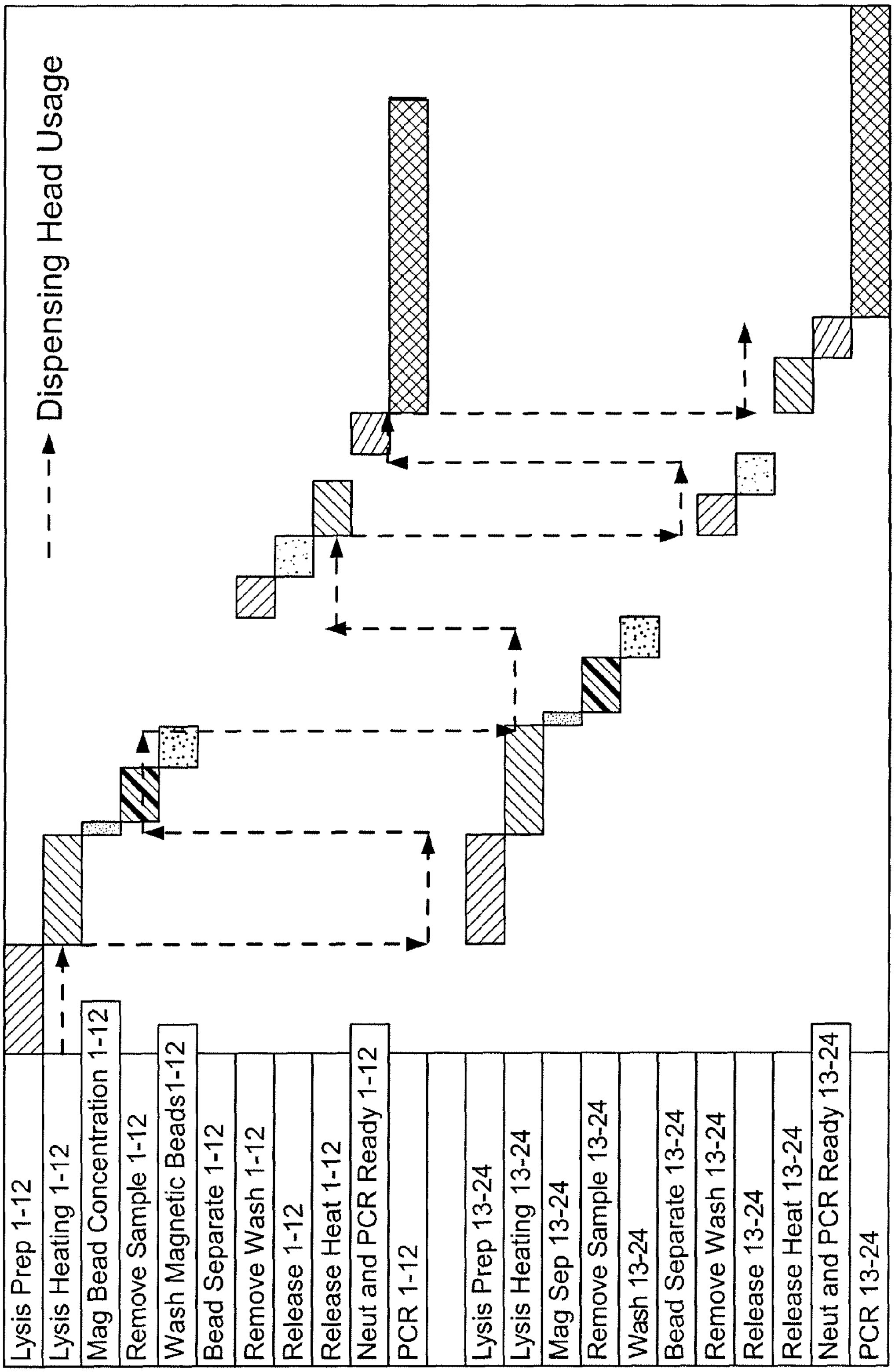
FIGS. 22A-22C show, schematically, pipette head usage during various preparatory processes.
Figure 22B:
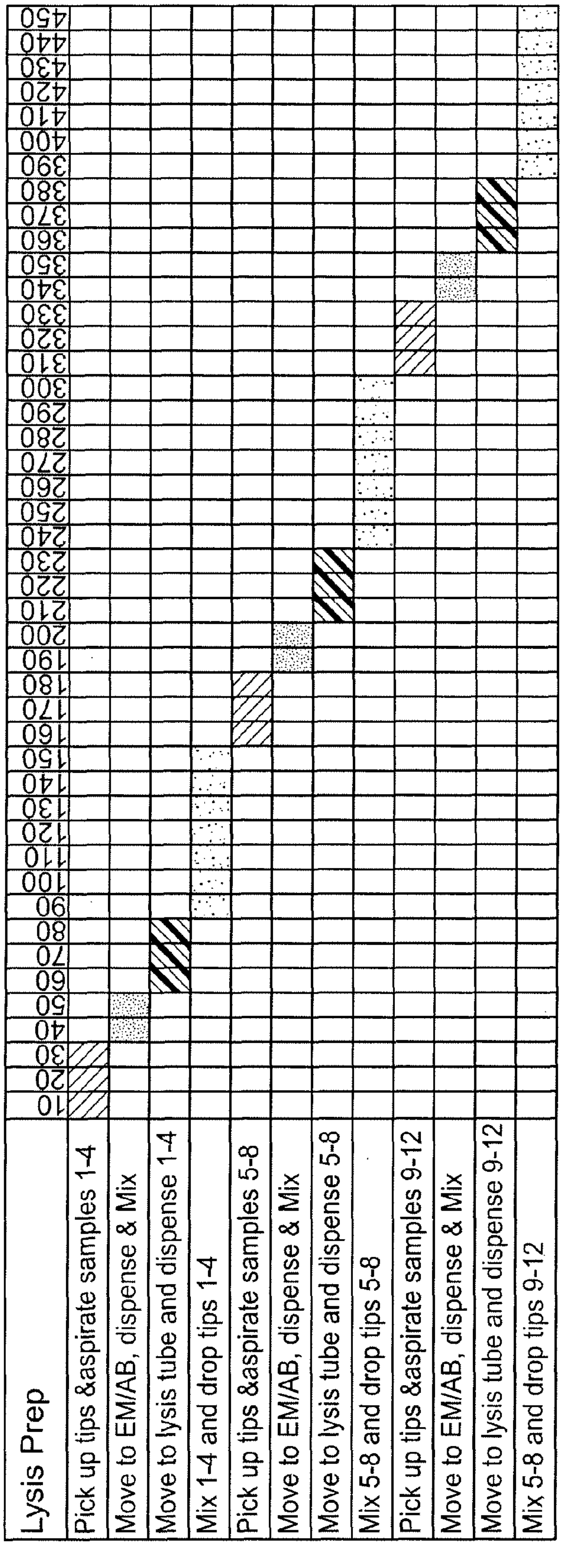
Figure 22C:
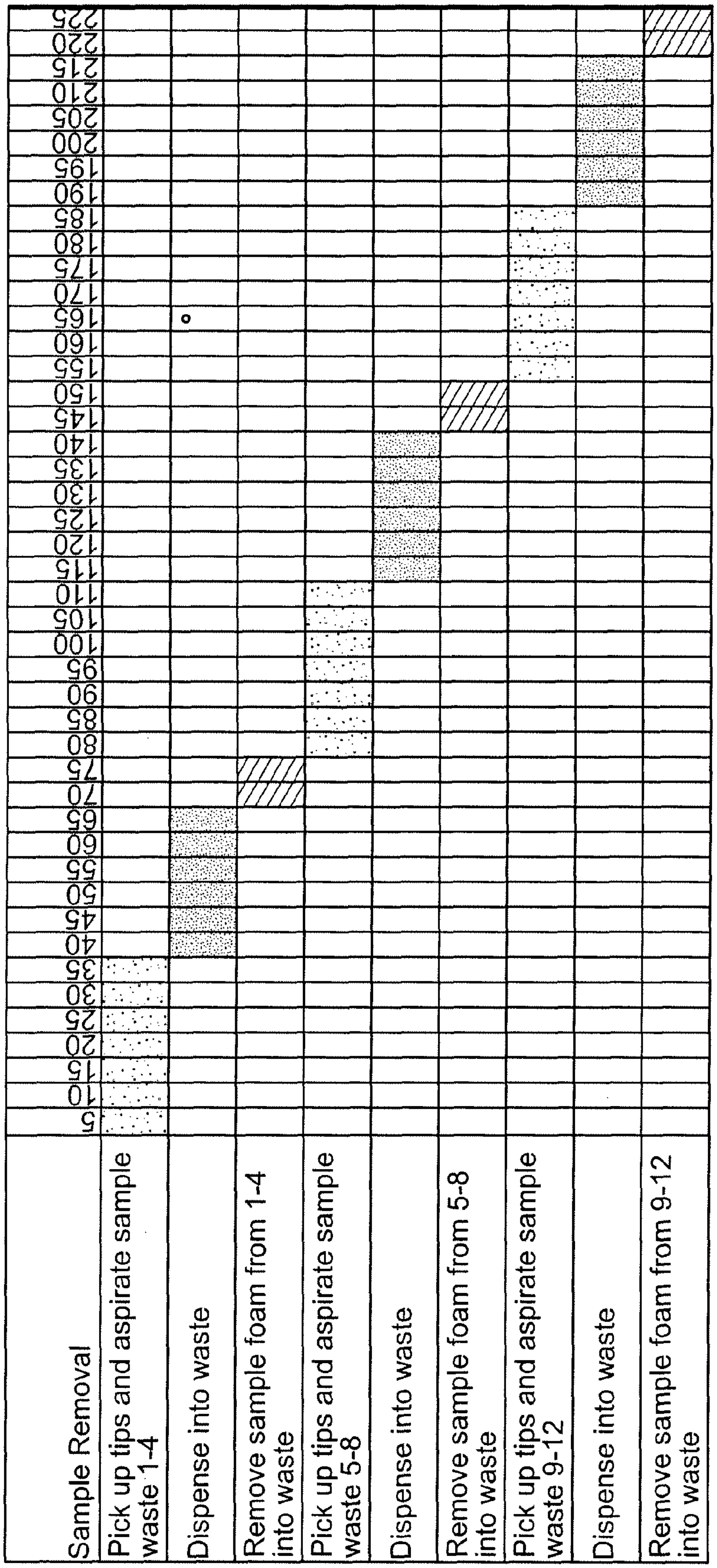

FIGS. 22A-22C show dispense head usage for pipetting operations on banks of 12 samples.

In FIG. 22A, operations on two racks, each containing 12 samples and corresponding reagent holders (labeled 1-12, and 13-24), are shown. The left hand side of the diagram itemizes the set of operations performed. Thus, e.g., "Lysis Prep 1-12" means perform lysis on samples 1-12. In this case, it is the same set of operations on each bank of 12 samples. The dashed line (with arrowheads) shows where liquid dispensing head is. Reading the diagram from left to right shows the order of operations. The dispense head can, e.g., alternate between performing operations on the two racks; the length of a shaded block indicates how long a step takes. In general, the sequence of operations is set up so that, while, e.g., an processing operation such as heating (that does not require the dispense head) is being carried out on one rack, the dispense head can be positioned over the other rack and carry out various liquid transfer operations.

FIG. 22B shows details of how one of the steps in FIG. 22A (Lysis prep.) is carried out on 12 samples, as positioned in a single rack. Numbers at the top of the chart represent time in seconds. The shaded blocks in the grid indicate the location of the dispense head. The operations are applied to the samples in batches of 4. Thus, there are 4 distinct operations to be performed on each sample. In the example shown, a complete sequence of operations on the first batch of 4 is carried out before starting the second batch. It would be understood by one of ordinary skill in the art, that such an approach is exemplary, and that other sequences of steps, or strategy, could be carried out, consistent with the overall goal.

FIG. 22C, laid out similarly to FIG. 22B, shows details of sample removal, expressed in terms of pipette tip aspiration and dispense operations.

The foregoing description is intended to illustrate various aspects of the present inventions. It is not intended that the examples presented herein limit the scope of the present inventions. The technology now being fully described, it will be apparent to one of ordinary skill in the art that many changes and modifications can be made thereto without departing from the spirit or scope of the appended claims.

What is claimed is:

1. An automated pipetting apparatus comprising:

a controller;

a gantry comprising a horizontal rail; and a liquid dispenser moveable vertically within a container to make contact with the liquid therein and configured to carry out suck and dispense operations therein, the liquid dispenser comprising a mechanical connection to the horizontal rail of the gantry and moveable along the gantry, the liquid dispenser comprising:

a plurality of pumps;

a plurality of dispense heads, each dispense head configured to receive gas from a respective one of the plurality of pumps; and electrical connections configured to transmit control signals from the controller to the plurality of pumps, the control signals controlling operation of each dispense head by controlling when to reduce gas pressure in one of the plurality of dispense heads, thereby causing a sucking operation, and controlling when to increase gas pressure in one of the plurality of dispense heads, thereby causing a dispense operation, the controller programmed to simultaneously actuate individual pumps of the plurality of pumps to dispense individual fluid volumes, at least one of the plurality of dispense heads configured to dispense a different fluid volume than the fluid volume simultaneously dispensed by at least one other dispense head, wherein the mechanical connection to the horizontal rail and the electrical connections to the controller are the only external connections to the liquid dispenser.

2. The automated pipetting apparatus of claim 1, wherein no gas lines connect the plurality of pumps to the gantry.

3. The automated pipetting apparatus of claim 1, wherein every dispense head of the plurality of dispense heads receives gas from its respective pump and dispenses fluid without gas being directed to any other pump or its respective dispense head.

4. The automated pipetting apparatus of claim 1, wherein the liquid dispenser comprises four pumps and four dispense heads, and wherein each head is configured to accept a pipette tip.

5. The automated pipetting apparatus of claim 4, wherein the liquid dispenser comprises a sensor configured to detect when a pipette tip is positioned on a dispense head, and wherein the automated pipetting apparatus further comprises one or more sensors configured to sense when vertical motion of the liquid dispenser is obstructed.

6. The automated pipetting apparatus of claim 1, configured to aspirate and dispense fluid in connection with analysis or preparation of solutions of two or more samples.

7. The automated pipetting apparatus of claim 1, wherein the liquid dispenser is configured to move in three dimensions.

8. The automated pipetting apparatus of claim 1, wherein the plurality of dispense heads are individually sprung.

9. The automated pipetting apparatus of claim 1, wherein no solution of a sample enters the plurality of dispense heads during normal operation of the dispenser.

10. The automated pipetting apparatus of claim 1, configured to aspirate, in a single operation, an amount of 1.0 ml of fluid or less, the automated pipetting apparatus further configured to dispense, in a single operation, an amount of 1.0 ml of fluid or less.

11. The automated pipetting apparatus of claim 1, configured to aspirate, in a single operation, an amount of fluid in the range 10 nl-1 ml, the automated pipetting apparatus further configured to dispense, in a single operation, an amount of 10 nl-1 ml of fluid or less.

12. The automated pipetting apparatus of claim 1, further comprising at least one of an individual pipette tip sensor, an encoder for the one or more pumps, a force sensor, a barcode sensor, and an image sensor.

13. The automated pipetting apparatus of claim 1, wherein the one or more pumps each comprise a plunger configured to compress or uncompress a volume of gas.

14. The automated pipetting apparatus of claim 13, wherein the controller is configured to independently control movement of each plunger to regulate gas flow to each of the plurality of dispense heads independent of gas flow to any other dispense head.

15. The automated pipetting apparatus of claim 1, wherein the liquid dispenser further comprises a printed circuit board configured to control operation of the plurality of pumps.

16. The automated pipetting apparatus of claim 1, wherein the controller is programmed to simultaneously actuate individual pumps of the plurality of pumps to aspirate individual fluid volumes, the fluid volume aspirated by at least one dispense head different from the fluid volume simultaneously aspirated by at least one other dispense head.

17. The automated pipetting apparatus of claim 1, wherein the controller is programmed to simultaneously vent individual pumps of the plurality of the pumps.

18. A method of dispensing a liquid using the automated pipetting apparatus of claim 1, the method comprising:

moving the liquid dispenser from a first position to a second position through the mechanical connection to the horizontal rail of the gantry;

transmitting a control signal from the controller to the plurality of pumps via the electrical connections; and independently regulating the flow of gas from each of the plurality of pumps to a respective one of the plurality of dispense heads.

19. The method of claim 18, wherein independently regulating the flow of gas comprises independently moving a plunger in each of the plurality of pumps to compress or uncompress a volume of gas.

20. The method of claim 19, wherein independently controlling a plunger comprises transmitting a control signal from the controller to a motor in each of the plurality of pumps.

21. The method of claim 18, wherein regulating gas flow to a dispense head corresponds to sucking a solution of a sample out of a container.

* * * * *